US012570606B2

(12) United States Patent
Chen et al.

(10) Patent No.: US 12,570,606 B2
(45) Date of Patent: Mar. 10, 2026

(54) MYELOPEROXIDASE IMAGING AGENTS

(71) Applicant: The General Hospital Corporation, Boston, MA (US)

(72) Inventors: John W. Chen, Newton, MA (US); Cuihua Wang, Cambridge, MA (US); Edmund J. Keliher, Topsfield, MA (US)

(73) Assignee: The General Hospital Corporation, Boston, MA (US)

( * ) Notice: Subject to any disclaimer, the term of this patent is extended or adjusted under 35 U.S.C. 154(b) by 667 days.

(21) Appl. No.: 17/733,891

(22) Filed: Apr. 29, 2022

(65) Prior Publication Data

US 2022/0340524 A1 Oct. 27, 2022

Related U.S. Application Data

(62) Division of application No. 16/461,255, filed as application No. PCT/US2017/061955 on Nov. 16, 2017, now Pat. No. 11,352,326.

(60) Provisional application No. 62/422,912, filed on Nov. 16, 2016.

(51) Int. Cl.

| | |
|---|---|
| ***C07D 209/20*** | (2006.01) |
| ***A61K 49/00*** | (2006.01) |
| ***A61K 51/04*** | (2006.01) |
| ***C07D 209/14*** | (2006.01) |
| ***C07D 495/04*** | (2006.01) |

(52) U.S. Cl.

CPC ........ *C07D 209/20* (2013.01); *A61K 49/0021* (2013.01); *A61K 51/0446* (2013.01); *C07D 209/14* (2013.01); *C07D 495/04* (2013.01)

(58) Field of Classification Search

CPC .. C07D 209/14; C07D 209/20; C07D 495/04; A61K 49/0021; A61K 51/0446

See application file for complete search history.

(56) References Cited

U.S. PATENT DOCUMENTS

| | | | |
|---|---|---|---|
| 2005/0090529 | A1 | 4/2005 | McAlpine et al. |
| 2009/0137595 | A1 | 5/2009 | Nozomu et al. |
| 2010/0284913 | A1 | 11/2010 | Bois et al. |
| 2011/0250145 | A1 | 10/2011 | Sharma et al. |
| 2015/0306077 | A1 | 10/2015 | Bulent et al. |

FOREIGN PATENT DOCUMENTS

| | | |
|---|---|---|
| CN | 1365971 | 8/2002 |
| CN | 101678118 | 3/2010 |
| EP | 0106281 | 4/1984 |
| EP | 0146787 | 7/1985 |
| EP | 1911744 | 4/2008 |
| EP | 1995240 | 11/2008 |
| WO | WO 2001/054681 | 8/2001 |
| WO | WO 2003/051366 | 6/2003 |
| WO | WO 2004/091480 | 10/2004 |
| WO | WO 2006/061638 | 6/2006 |
| WO | WO 2010/033640 | 3/2010 |
| WO | WO 2010/138421 | 12/2010 |
| WO | WO 2015/048306 | 4/2015 |
| WO | WO 2015/162216 | 10/2015 |
| WO | WO 2018/094005 | 5/2018 |

OTHER PUBLICATIONS

Dafik et al., Chemistry & Biology 18, 58-66, Jan. 28, 2011.*

Brennan et al, "Increased atherosclerosis in myeloperoxidase-deficient mice," The Journal of Clinical Investigation, Feb. 2001, 107(4):419-430.

Brennan et al, "Prognostic value of myeloperoxidase in patients with chest pain," N. Engl. J. Med. Oct. 2003, 349(17)1595-1604.

Chen et al, "A Fluorescent Probe for the Detection of Myeloperoxidase Activity in Atherosclerosis-Associated Macrophages," Brain: A Journal of Neurology, Apr. 2008, 131(4):1123-1133.

CN Office Action in Chinese Appln. No. 201780083487.6, dated Jun. 2, 2021, 16 pages (with English translation).

EP Extended European Search Report in EP Appln. No. EP 17871464, dated Jun. 25, 2020, 14 pages.

EP Supplementary Partial European Search Report in EP Appln. No. EP 17871464, dated Apr. 1, 2020, 10 pages.

First Search in Chinese Appln. No. 201780083487.6, dated May 25, 2021, 2 pages.

Forghani et al, "Myeloperoxidase propagates damage and is a potential therapeutic target for subacute stroke," Journal of Cerebral Blood Flow and Metabolism, Mar. 2015, 35(3):485-493.

Gray et al, "Elevated activity and microglial expression of myeloperoxidase in demyelinated cerebral cortex in multiple sclerosis," Brain Pathology, 2008, 18(1):86-95.

Gray et al, "Elevated myeloperoxidase activity in white matter in multiple sclerosis," Neuroscience Letters, Aug. 2008, 444(2):195-198.

Gross et al, "Bioluminescence imaging of myeloperoxidase activity in vivo," Nature Medicine, 2009, 15(4):455-461.

Julia et al., "N° 350.—Tetrahydro-et dihydro-:3-carbolines derive esdu tryptophane et du methoxy-5 tryptophane," Bulletin De La Societe Chimique De France, Societe Francaise De Chimie, Jan. 1973, 6:2058-2064.

Maki et al, "Aberrant Expression of Myeloperoxidase in Astrocytes Promotes Phospholipid Oxidation and Memory Deficits in a Mouse Model of Alzheimer Disease," The Journal of Biological Chemistry, Jan. 2009, 284(5):3158-3169.

Nahrendorf et al, "Activatable Magnetic Resonance Imaging Agent Reports Myeloperoxidase Activity in Healing Infarcts and Noninvasively Detects the Antiinflammatory Effects of Atorvastatin on Ischemia-Reperfusion Injury," Circulation, Feb. 2008, 117(9):1153-1160.

Nicholls et al, "Myeloperoxidase and Cardiovascular Disease," Arteriosclerosis, Thrombosis, and Vascular Biology, Mar. 2005, 25(6):1102-1111.

(Continued)

*Primary Examiner* — Alicia L Otton

(74) *Attorney, Agent, or Firm* — Fish & Richardson P.C.

(57) ABSTRACT

Provided herein are compounds useful as imaging agents. Exemplary compounds provided herein are useful as myeloperoxidase imaging agents using positron emission tomography or fluorescence imaging techniques. Methods for preparing the compounds provided herein and diagnostic methods using radiolabeled arid unlabeled compounds are also provided.

37 Claims, 17 Drawing Sheets

(56) References Cited

OTHER PUBLICATIONS

Office Action in Chinese Appln. No. 201780083487.6, dated Dec. 13, 2021, 15 pages (with English translation).
Office Action in European Appln. No. 17871464.8, dated Jun. 7, 2022, 6 pages.
Panizzi et al, "Oxazine conjugated nanoparticle detects in vivo hypochlorous acid and peroxynitrite generation," Journal of the American Chemical Society, Nov. 2009, 131(43):15739-15744.
PCT International Preliminary Report on Patentability in International Appln. No. PCT/US2017/061955, dated May 21, 2019, 8 pages.
PCT International Search Report and Written Opinion in International Appln. No. PCT/US2017/061955, dated Mar. 23, 2018, 14 pages.
Perez et al., "Viral detection using DNA functionalized gold filaments," Analyst, May 2009, 134(8):1548-1553.
PUBCHEM CID 67231449 Create Date: Nov. 30, 2012 (Nov. 30, 2012) pp. 1-12; p. 4, Fig.
PUBCHEM-CID 42696014 Create Date: Jul. 20, 2009 (Jul. 20, 2009) pp. 1-10; p. 3, Fig.
PUBCHEM-CID 56942494 Create Date: Apr. 23, 2012 (Apr. 23, 2012) pp. 1-12; p. 4, Fig.
Reynolds et al, "Myeloperoxidase polymorphism is associated with gender specific risk for Alzheimer's disease," Experimental Neurology, Jan. 1999, 155(1):31-41.
Rodriguez et al., "Activatable magnetic resonance imaging agents for myeloperoxidase sensing: mechanism of activation, stability, and toxicity," Journal of the American Chemical Society, Jan. 2010, 132(1):168-177.
Shepherd et al, "A Fluorescent Probe for the Detection of Myeloperoxidase Activity in Atherosclerosis-Associated Macrophages," Chemistry & Biology, 2007, 14(11):1221-1231.
STN Registry Database Entry for CAS RN 1032997-79-7, Entered STN Jul. 8, 2008, Accessed Apr. 22, 2021, 5 pages.
STN Registry Database Entry for CAS RN 1820968-73-7, Entered STN Nov. 19, 2015, Accessed Apr. 22, 2021, 5 pages.
STN Registry entry for CAS RN 1989424-94-3, Entered STN Sep. 8, 2016, Accessed Mar. 1, 2020, 1 page.
STN Search Report, NIST Mass Spectral Library (National Institute of Standards and Technology, STN Registry, 1 page.
Swirski et al, "Myeloperoxidase-rich Ly-6C+ myeloid cells infiltrate allografts and contribute to an imaging signature of organ rejection in mice," The Journal of Clinical Investigation, Jul. 2010, 120(7):2627-2634.
Volker et al, "Myeloperoxidase acts as a profibrotic mediator of atrial fibrillation," Nature Medicine, Mar. 2010, 16(4):470-474.
Xie et al., "Design, synthesis of novel tryptophan derivatives for antiplatelet aggregation activity based on tripeptide pENW (pGlu-Asn-Trp)," European journal of medicinal chemistry, Sep. 2015, 102:363-374.
Zhang et al, "Enhanced detection of myeloperoxidase activity in deep tissues through luminescent excitation of near-infrared nanoparticles," Nature Medicine, Mar. 2013, 19(4):500-505.

* cited by examiner

| Sensor | 5-HT | 5-HT | 5-HT | 5-HT | 5-HT | 5-HT | tyrosine | tyrosine |
|---|---|---|---|---|---|---|---|---|
| MPO | + | + | + | + | - | - | - | + |
| GOX | + | + | - | + | - | - | - | + |
| ABAH | - | + (gel) | - | - | + | + (i.p.) | + | - |

Irritant Contact Dermatitis

MYELOPEROXIDASE IMAGING AGENTS

CROSS-REFERENCE TO RELATED APPLICATIONS

This application is a divisional of U.S. patent application Ser. No. 16/461,255, filed May 15, 2019, which is a national stage application under 35 U.S.C. § 371 of International Application No. PCT/US2017/061955 filed on Nov. 16, 2017, which claims the benefit of U.S. Provisional Application Ser. No. 62/422,912, filed Nov. 16, 2016 the disclosure of which is incorporated herein by reference in its entirety.

This invention was made with government support under Grant No. NS070835 awarded by the National Institutes of Health. The government has certain rights in the invention.

TECHNICAL FIELD

This invention relates to compounds useful as imaging agents and more particularly to compounds useful as myeloperoxidase imaging agents.

BACKGROUND

Myeloperoxidase (MPO) is a heme-containing oxidizing enzyme mainly produced by neutrophil granulocytes and monocytes and plays a crucial role in host defense against pathogen by generating reactive oxygen species (ROS) and other oxidants. However, ill-regulated MPO activity also contributes to tissue damage.

SUMMARY

The present application provides, inter alia, a compound of Formula I:

I

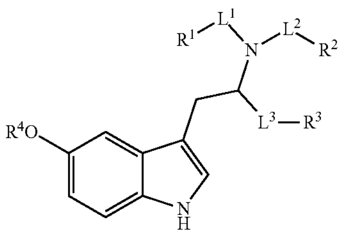

or a pharmaceutically acceptable salt thereof wherein:

- $L^1$ is selected from the group consisting of a bond, —C(O)—, —C(O)O—, —C(O)NR$^{a1}$—, —C(O)($C_{1-6}$ alkylene)-, and —C(O)($C_{1-6}$ alkyleneoxy)-;
- $R^1$ is selected from the group consisting of H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;
- $L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterorycloalkylene)-, —($C_{1-6}$ alkylene)-(5-10 membered heteroarylene)-, —C(O)O—, —C(O)O—, —C(O)NR$^{a2}$—, —C(O)($C_{1-6}$ alkylene)-, and —C(O)($C_{1-6}$ alkyleneoxy)-;
- $R^2$ is selected from the group consisting of $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkoxy, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;
- $L^3$ is selected from the group consisting of a bond, —C(O)—, —C(O)O—, —C(O)NR$^{a3}$—, —C(O)($C_{1-6}$ alkylene)-, —C(O)($C_{1-6}$ alkyleneoxy)-, —C(O)N(R$^{a3}$)($C_{1-6}$alkylene)-, and —C(O)N(R$^{a3}$)($C_{1-6}$ alkyleneoxy)-;
- $R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, and 5-10 membered heteroaryl, is optionally substituted by 1, 2, 3, or 4 substituents independently selected from OH, halo, $C_{1-6}$ alkoxy, and $C_{1-6}$ haloalkyl;
- or alternatively, -$L^3$-$R^3$ forms an oxo group;
- $R^4$ is selected from the group consisting of H, $C_{1-6}$ alkyl, $C_{2-6}$ alkenyl, $C_{2-6}$ alkynyl, and $C_{1-6}$ haloalkyl;
- and each R$^{a1}$, R$^{a2}$, and R$^{a3}$ is independently selected from the group consisting of H, $C_{1-6}$ alkyl, $C_{2-6}$ alkenyl, $C_{2-6}$ alkynyl, and $C_{1-6}$ haloalkyl.

In some embodiments, $L^1$ is selected from the group consisting of a bond, —C(O)—, —C(O)($C_{1-6}$ alkylene)-, and —C(O)($C_{1-6}$ alkyleneoxy)-. In some embodiments, $L^1$ is selected from the group consisting of a bond and —C(O)($C_{1-6}$ alkylene)-. In some embodiments, $L^1$ is a bond. In some embodiments, $L^1$ is —C(O)($C_{1-6}$ alkylene)-.

In some embodiments, $R^1$ is selected from the group consisting of H, $C_{3-10}$ cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl. In some embodiments, $R^1$ is selected from the group consisting of H and 4-10 membered heterocycloalkyl, wherein the 4-10 membered heterocycloalkyl is optionally substituted by 1, 2, 3, or 4 substituents independently selected from OH, halo, and $C_{1-6}$ haloalkyl. In some embodiments, $R^1$ is H. In some embodiments, $R^1$ is a 4-10 membered heterocycloalkyl, wherein the 4-10 membered heterocycloalkyl is optionally substituted by 1, 2, 3, or 4 substituents independently selected from OH, halo, and $C_{1-6}$ haloalkyl. In some embodiments, $R^1$ is a 4-10 membered heterocycloalkyl, wherein the 4-10 membered heterocycloalkyl is unsubstituted.

In some embodiments, $L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, and —C(O)($C_{1-6}$ alkylene)-. In some embodiments, $L^2$ is selected from the group consisting of —($C_{1-6}$ alkylene)-(5-10 membered heteroarylene)-, —C(O)—, and —C(O)($C_{1-6}$ alkylene)-.

In some embodiments, $R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl. In some embodiments, $R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, and 4-10 membered heterocycloalkyl, 5-10 membered heteroaryl is optionally substituted by one substituent independently selected from OH, halo, and $C_{1-6}$ haloalkyl.

In some embodiments, $L^3$ is selected from the group consisting of a bond, —C(O)NR$^{a3}$—, —C(O)N(R$^{a3}$)($C_{1-6}$ alkylene)-, and —C(O)N(R$^{a3}$)($C_{1-6}$ alkyleneoxy)-. In some embodiments, $L^3$ is selected from the group consisting of a bond, —C(O)N(R$^{a3}$)($C_{1-6}$ alkylene)-, and —C(O)N(R$^{a3}$)($C_{1-6}$ alkyleneoxy)-.

In some embodiments, $R^3$ is selected from the group consisting of H, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl. In some embodiments, $R^3$ is selected from the group consisting of H, $C_{1-6}$ haloalkyl, and 5-10 membered heteroaryl, wherein each $C_{1-6}$ haloalkyl, and 5-10 membered heteroaryl is optionally substituted by 1, 2, 3, or 4 substituents independently selected from OH, halo, and $C_{1-6}$ haloalkyl. In some embodiments, $R^3$ is selected from the group consisting of H, $C_{1-6}$ haloalkyl, and 5-10 membered heteroaryl, wherein each $C_{1-6}$ haloalkyl, and 5-10 membered heteroaryl is optionally substituted by one substituent independently selected from OH, halo, and $C_{1-6}$ haloalkyl.

In some embodiments, -$L^3$-$R^3$ forms an oxo group.

In some embodiments, $R^4$ is H.

In some embodiments, each $R^{a1}$, $R^{a2}$ and $R^{a3}$ is H.

In some embodiments:

$L^1$ is selected from the group consisting of a bond, —C(O)—, —C(O)($C_{1-6}$ alkylene)-, and —C(O)($C_{1-6}$ alkyleneoxy)-;

$R^1$ is selected from the group consisting of H, cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$-alkylene)-(4-10 membered heterocycloalkylene)-, —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)NR$^{a3}$, —C(O)N(R$^{a3}$)($C_{1-6}$ alkylene)-, and —C(O)N(R$^{a3}$)($C_{1-6}$ alkyleneoxy)-; and $R^3$ is selected from the group consisting of H, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

or alternatively, -$L^3$-$R^3$ forms an oxo group.

In some embodiments:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by 1, 2, 3, or 4 substituents independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N(R$^{a3}$)($C_{1-6}$ alkylene)-, and —C(O)N(R$^{a3}$)($C_{1-6}$ alkyleneoxy)-; and $R^3$ is selected from the group consisting of H, $C_{1-6}$ haloalkyl, and 5-10 membered heteroaryl, wherein each $C_{1-6}$ haloalkyl, and 5-10 membered heteroaryl is optionally substituted by 1, 2, 3, or 4 substituents independently selected from OH, halo, and $C_{1-6}$ haloalkyl;

or alternatively, -$L^3$-$R^3$ forms an oxo group.

In some embodiments:

$L^1$ is selected from the group consisting of a bond and —C(O)($C_{1-6}$ alkylene)-;

$R^1$ is, selected from the group consisting of H and 4-10 membered heterocycloalkyl, wherein the 4-10 membered heterocycloalkyl is optionally substituted by one substituent independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by one substituent independently selected from OH, halo, and $C_{1-6}$ haloalkyl;

$L^3$ is selected from the group consisting of a bond, —C(O)N(R$^{a3}$)($C_{1-6}$alkylene)-, and —C(O)N(R$^{a3}$)($C_{1-6}$ alkyleneoxy)-; and $R^3$ is selected from the group consisting of H, $C_{1-6}$ haloalkyl, and 5-10 membered heteroaryl, wherein each $C_{1-6}$ haloalkyl, and 5-10 membered heteroaryl is optionally substituted by one substituent independently selected from OH, halo, and $C_{1-6}$ haloalkyl;

or alternatively, -$L^3$-$R^3$ forms an oxo group.

In some embodiments, $R^4$ is H. In some embodiments, $R^{a3}$ is H.

In some embodiments, the compound of Formula I is a compound of Formula II:

(II)

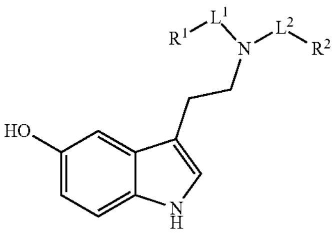

or a pharmaceutically acceptable salt thereof.

In some embodiments, the compound of Formula I is a compound of Formula III:

(III)

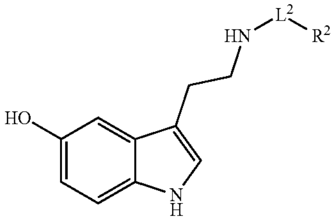

or a pharmaceutically acceptable salt thereof.

In some embodiments, the compound of Formula I is a compound of Formula IV:

(IV)

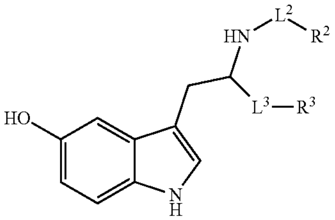

or a pharmaceutically acceptable salt thereof.

In some embodiments, the compound of Formula I is a compound of Formula V:

(V)

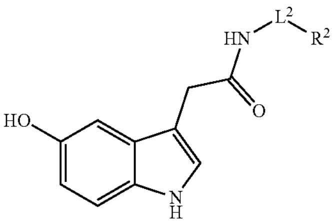

or a pharmaceutically acceptable salt thereof.

In some embodiments, the compound is selected from the group consisting of:

(3)

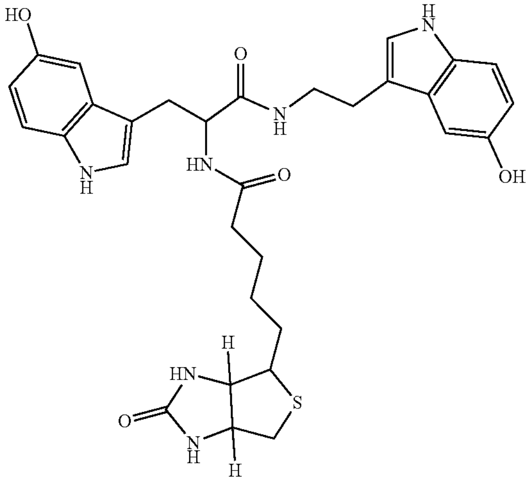

(4)

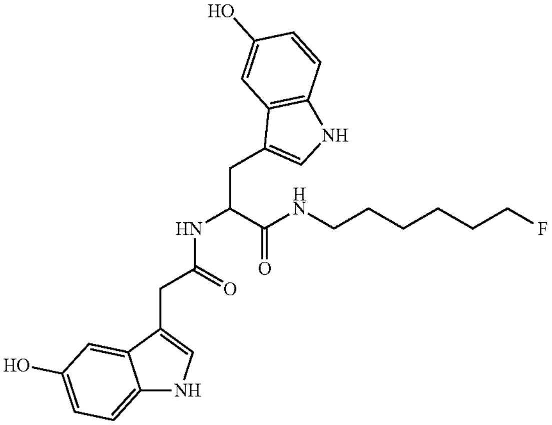

(5)

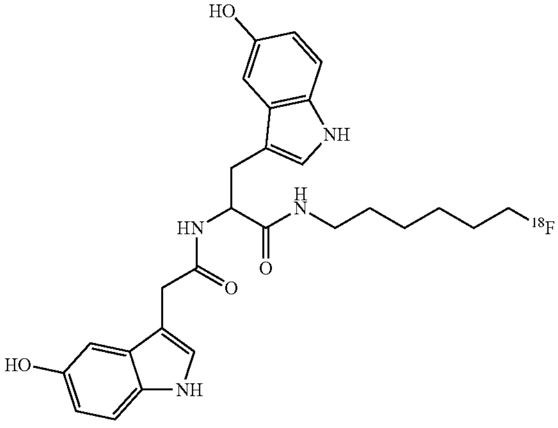

-continued
(6)
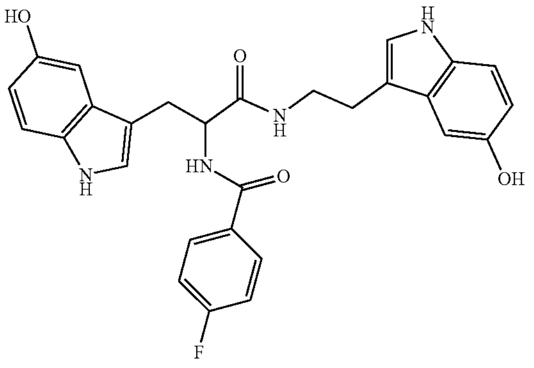
(7)
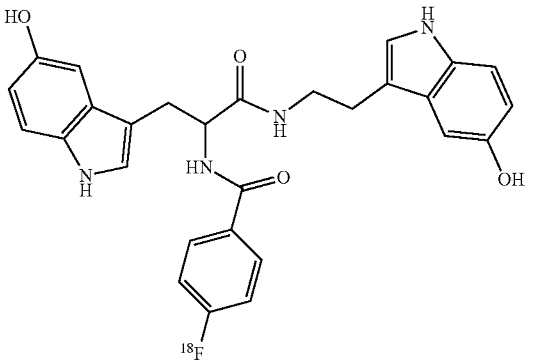
(8)
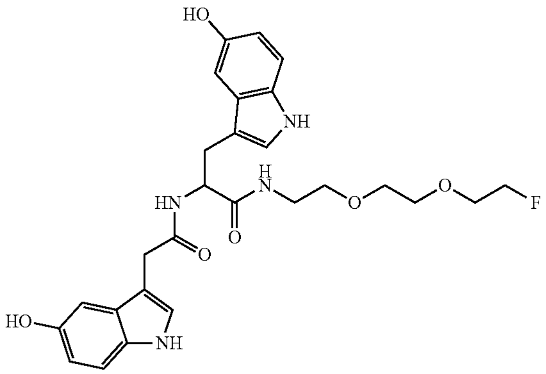
(9)
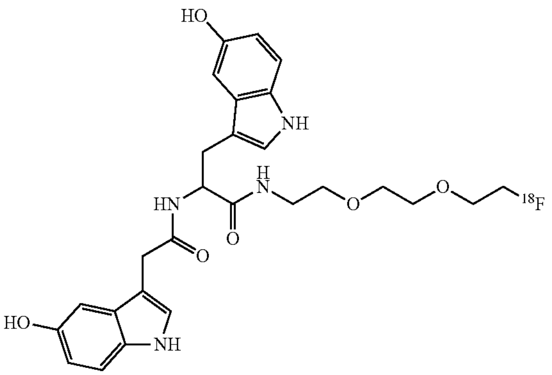
-continued
(12)
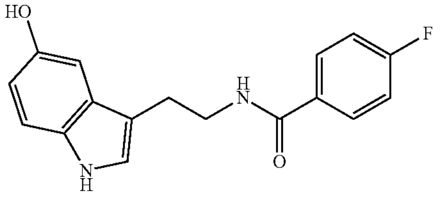
(13)
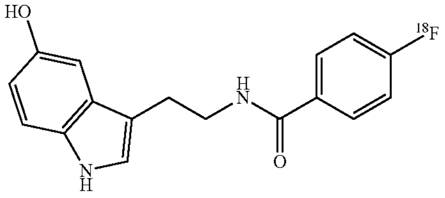
(14)
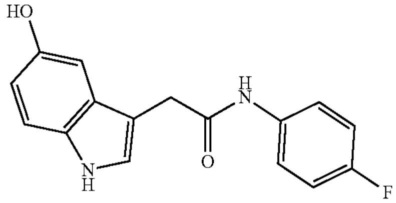
(15)
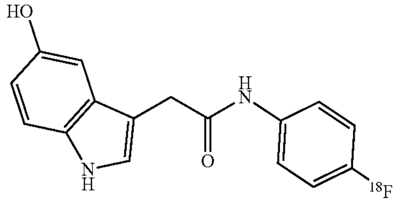
(16)
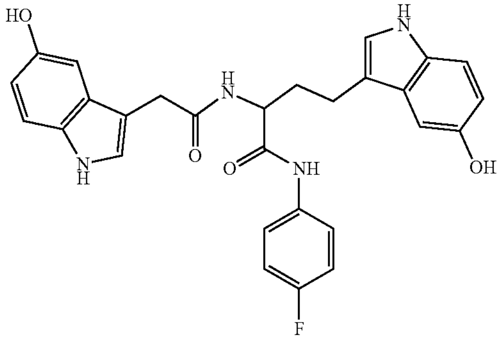
and
(17)
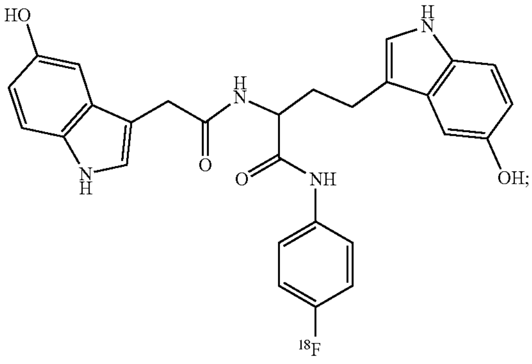
or a pharmaceutically acceptable salt thereof.

The present application further provides a pharmaceutical composition comprising a compound provided herein, or a pharmaceutically acceptable salt thereof, and at least one pharmaceutically acceptable carrier.

The present application further provides a method of imaging a cell or tissue sample, the method comprising:

i) administering to the subject a compound provided herein;

ii) waiting a time sufficient to allow the compound to accumulate at the cell or tissue sample; and iii) imaging the cell or tissue sample with an imaging technique.

The present application further provides a method of diagnosing a disease or disorder associated with abnormal myeloperoxidase activity in a subject, comprising:

i) administering to the subject a compound provided herein;

ii) waiting a time sufficient to allow the compound to accumulate at a cell or tissue site associated with the disease; and iii) imaging the cell or tissue with an imaging technique In some embodiments, the method further comprises imaging the subject prior to step i).

The present application further provides a method of imaging myeloperoxidase activity in a cell, the method comprising:

i) contacting the cell with a compound provided herein, or a pharmaceutically acceptable salt thereof; and iii) imaging the cell with an imaging technique.

The present application further provides a method of detecting myeloperoxidase activity in a cell or tissue sample, the method comprising:

i) contacting the cell or tissue sample with a compound provided herein, or a pharmaceutically acceptable salt thereof; and iii) imaging the cell or tissue sample with an imaging technique.

The present application further provides a method of detecting myeloperoxidase activity in a subject, the method comprising:

i) administering to the subject a compound provided herein, or a pharmaceutically acceptable salt thereof; and iii) imaging the subject with an imaging technique.

The present application further provides a method of monitoring treatment of a disease or disorder associated with abnormal myeloperoxidase activity in a subject, the method comprising:

i) administering to the subject a compound provided herein, or a pharmaceutically acceptable salt thereof;

ii) imaging the subject with an imaging technique;

iii) administering to the subject a therapeutically effective amount of a therapeutic compound to treat the disease or disorder;

iv) imaging the cell or tissue in the subject with an imaging technique; and v) comparing the image of step i) and the image of step iv).

In some embodiments, the method further comprises administering to the subject a compound provided herein, or a pharmaceutically acceptable salt thereof, after the administering of step iii) and prior to the imaging of step iv).

In some embodiments, the imaging technique is selected from the group consisting of fluorescence imaging and positron emission tomography.

In some embodiments, the compound is:

(3)

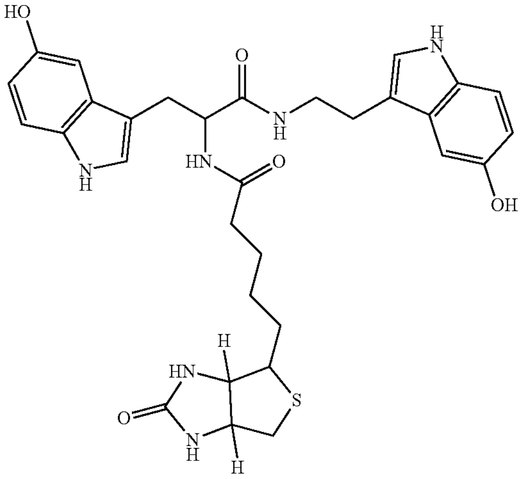

and the imaging technique is fluorescence imaging.

In some embodiments, the compound is selected from the group consisting of:

(5)

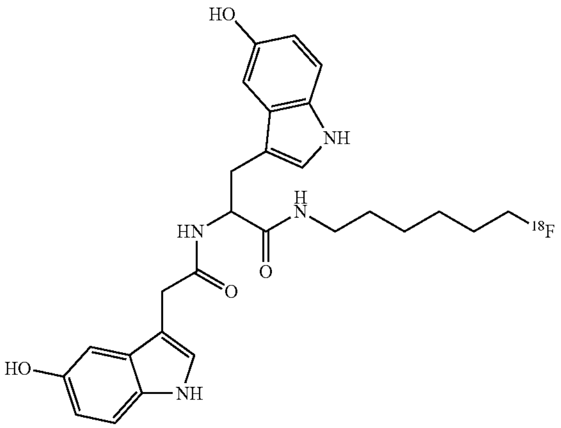

(7)

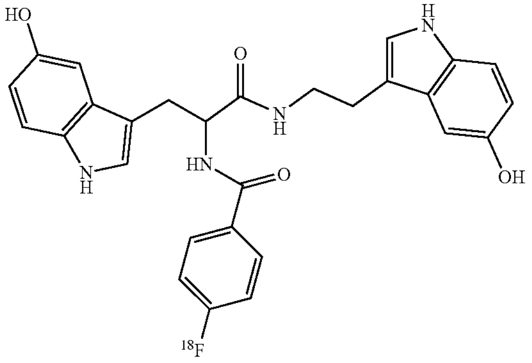

-continued (9)

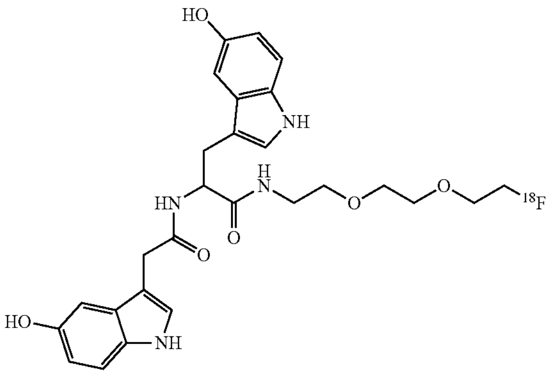

(13)

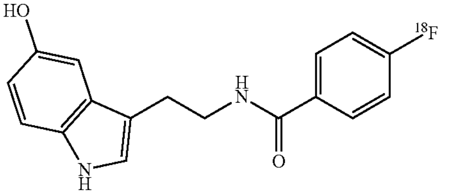

(15)

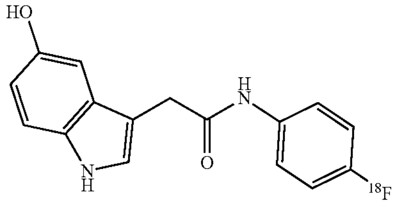

and (17)

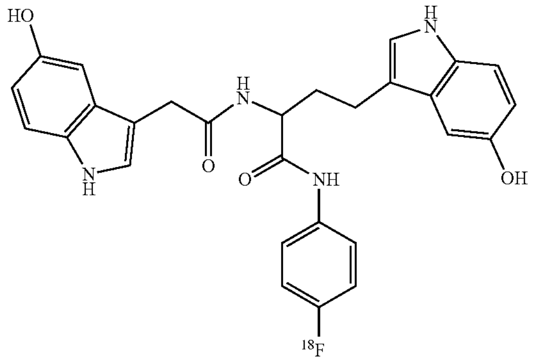

and the imaging technique is positron emission tomography.

In some embodiments, the disease or disorder associated with abnormal myeloperoxidase activity is selected from the group consisting of a cancer, a rheumatic disease, an infectious disease, a disease of the central nervous system a cardiovascular disorder, an autoimmune disorder, and inflammation associated with one or more of a cancer, a rheumatic disease, an infectious disease, disease of the central nervous system, cardiovascular disorder and autoimmune disorder.

In some embodiments, the disease of the central nervous system is selected from the group consisting of Alzheimer's disease, stroke, epilepsy, Parkinson's disease, a neurodegenerative disease, and inflammation associated with one or more of Alzheimer's disease, stroke, epilepsy, Parkinson's disease, and neurodegenerative disease.

In some embodiments, the cardiovascular disorder is selected from the group consisting of atherosclerosis, myocardial infarction, atrial fibrillation, vasculitis, and inflammation associated with one or more of atherosclerosis, myocardial infarction, atrial fibrillation, and vasculitis.

In some embodiments, the autoimmune disorder is selected from the group consisting of multiple sclerosis, meningitis, encephalitis, and inflammation associated with one or more of multiple sclerosis, meningitis, and encephalitis.

In some embodiments, the cancer is selected from the group consisting of bladder cancer, breast cancer, carcinoma, cervical cancer, colorectal cancer, endometrial cancer, glioma, cancer of the head and neck, liver cancer, lung cancer, melanoma, ovarian cancer, pancreatic cancer, prostate cancer, renal cancer, skin cancer, stomach cancer, testicular cancer, leukemia, and thyroid cancer. In some embodiments, the cancer is a solid tumor.

In some embodiments, the rheumatic disease is selected from the group consisting of rheumatoid arthritis, osteoarthritis, and inflammatory arthritis. In some embodiments, the inflammatory arthritis is selected from the group consisting of gout and calcium pyrophosphate deposition disease (CPPD).

In some embodiments, the infectious disease is selected from the group consisting of a fungal disease and a bacterial disease.

Unless otherwise defined, all technical and scientific terms used herein have the same meaning as commonly understood by one of ordinary skill in the art to which this invention belongs. Methods and materials are described herein for use in the present invention: other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Figure 5A:
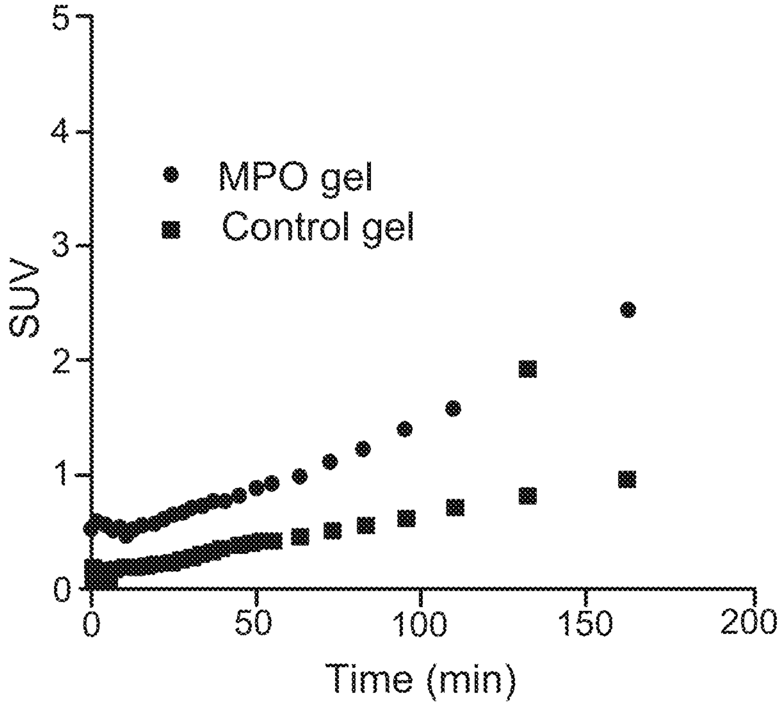
FIGS. 5A-5B shows representative results of a dynamic study of MPO Compound 9 over 3 hours: MPO gel vs.
Figure 5B:
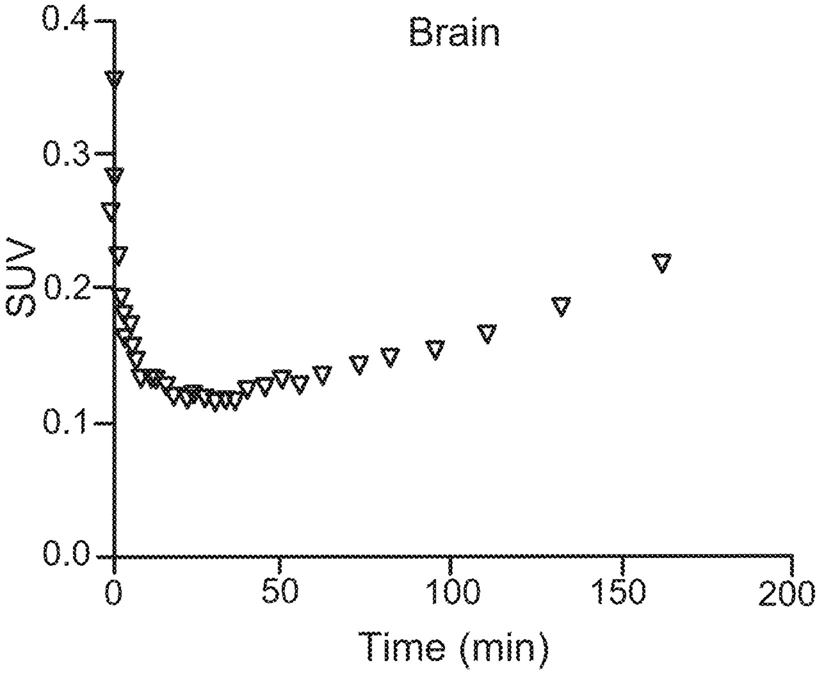
Figure 5C:
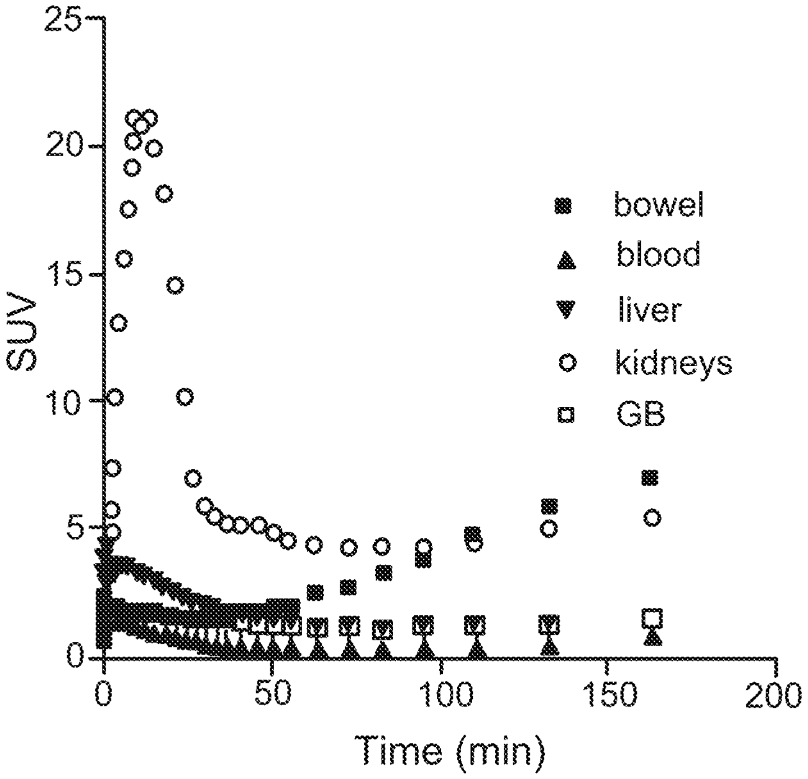
Figure 5D:
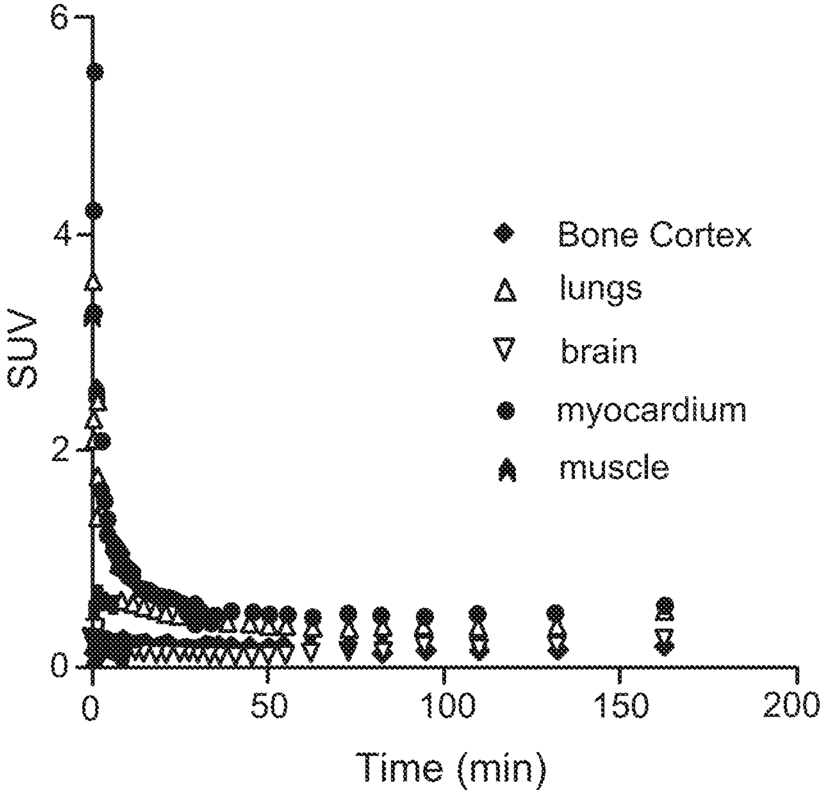

control gel (FIG. 5A); Brain data showing that Compound 9 can cross the blood-brain barrier (FIG. 5B); Dynamic data in organs (FIGS. 5C-5D).

Figure 6A:
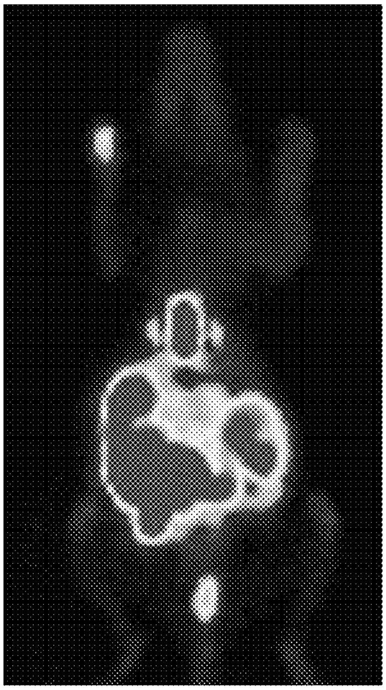
Figure 6B:
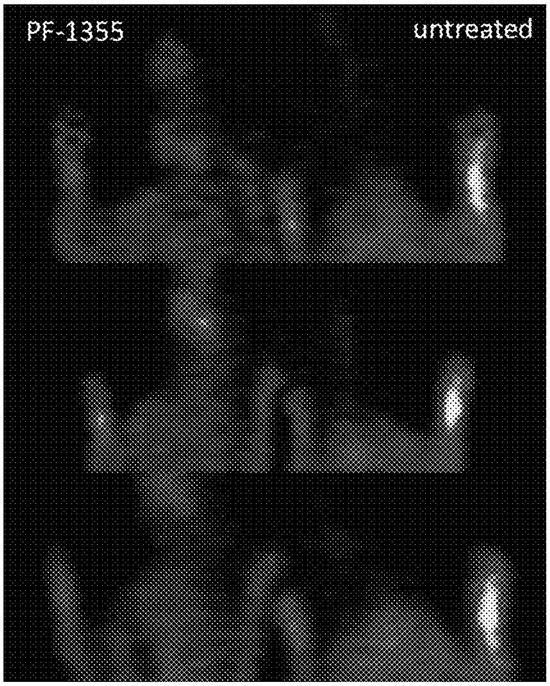

FIGS. 6A-6B shows representative data from a CFA paw inflammation model. (FIG. 6A) Right Paw: PBS; Left Paw: CFA emulsion (1/1 of CFA/PBS); (FIG. 6B) Left Paw: PF-1355 treated; Right Paw: untreated.

Figure 6C:
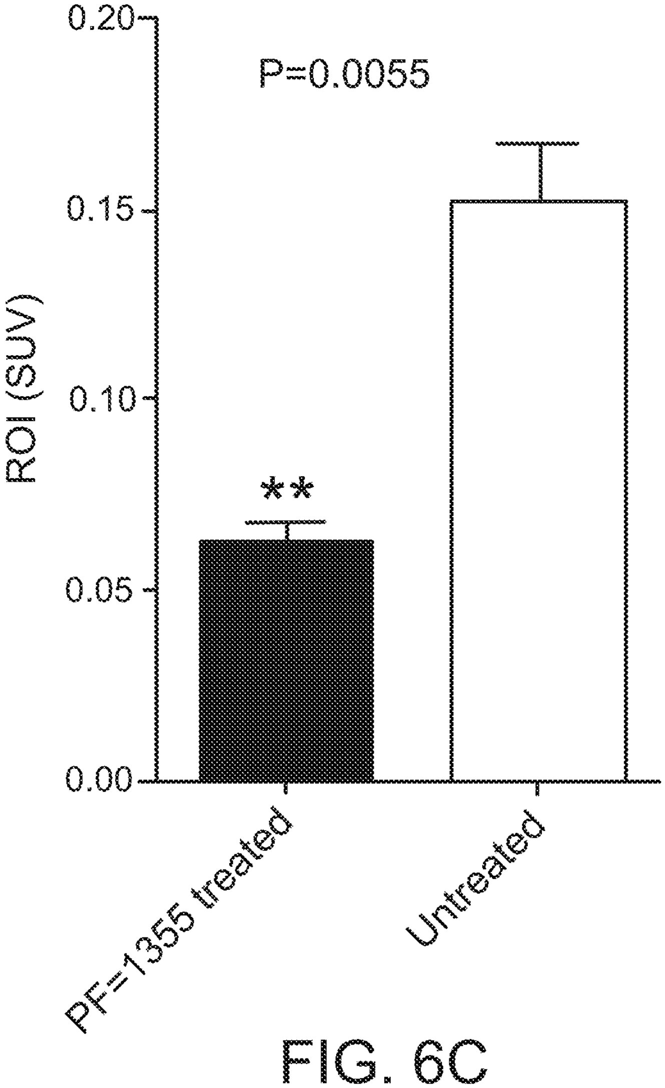

FIG. 6C shows quantitative analysis demonstrating that an MPO inhibitor decreased MPO-sensitive radiotracer uptake in the inflamed paw.

Figure 7A:
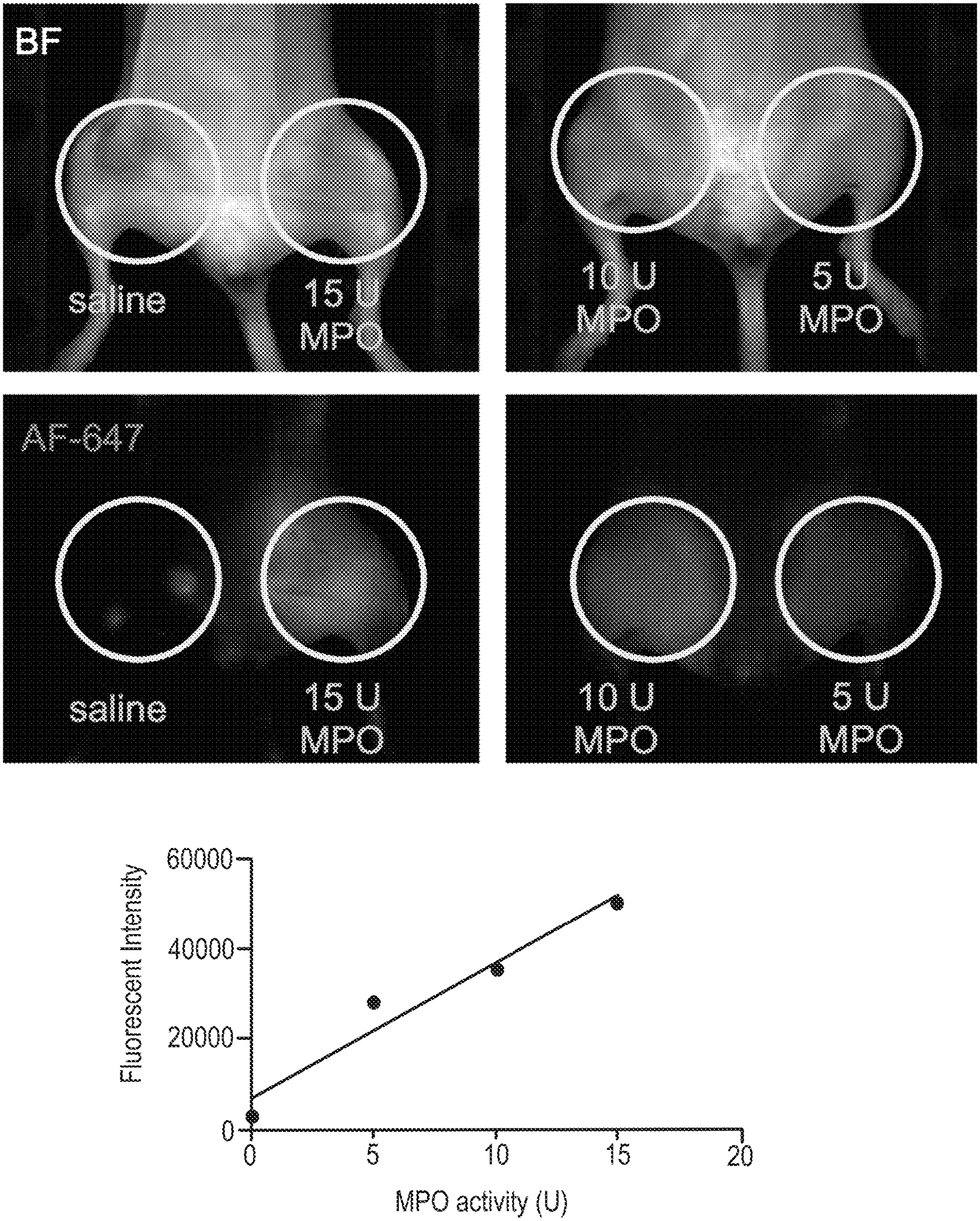

FIG. 7A shows fluorescence molecular tomography (FMT) at 15, 30, 45, and 60 minutes after injection of Compound 3 and AF-647, as well as different concentrations of MPO embedded in matrigel into mouse thighs. A schematic on injection sites and quantities of MPO is seen in the left panel. Image quantification revealed a linear increase with increasing quantities of MPO, with increase of fluorescence signal over time.

Figure 7B:
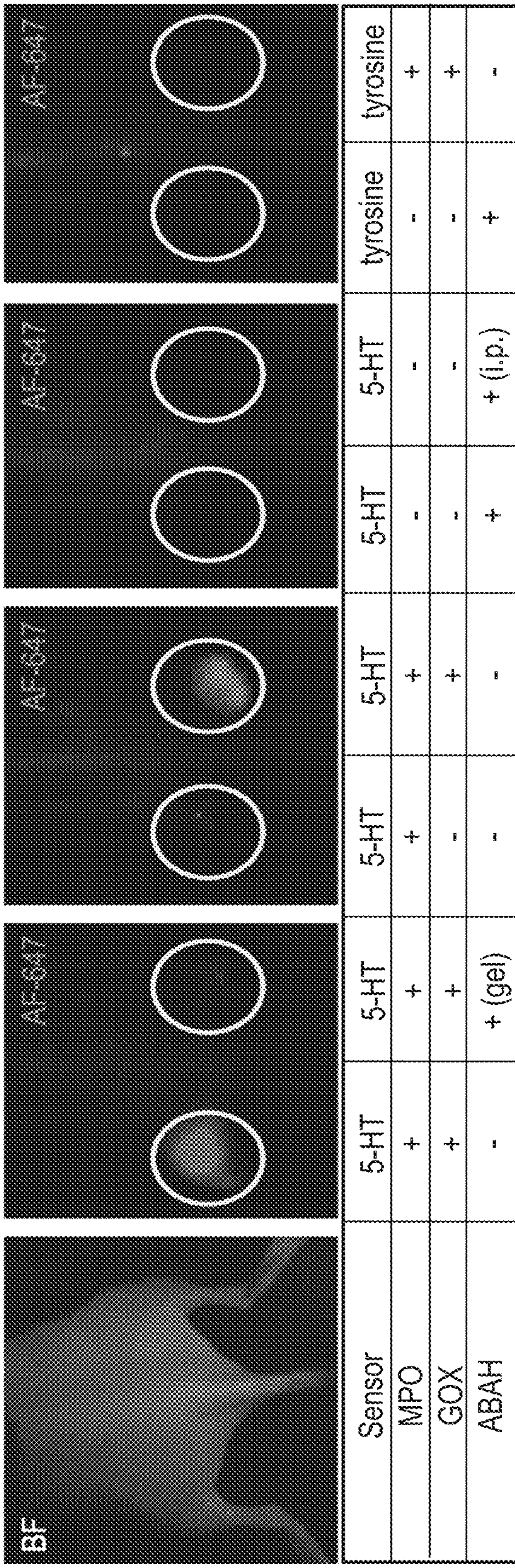

FIG. 7B shows fluorescence reflectance imaging (FRI) of different combinations of glucose oxidase (GOX), MPO, and the irreversible MPO inhibitor ABAH embedded in matrigel into mouse thighs and injected with Compound 3 and AF-647 (panels ii-vi). Circles outline the sites matrigel injection. ABAH was either embedded in matrigel together with MPO and GOX, or administered intraperitoneally (i.p.). A nonspecific analogue containing a tyrosine group was also injected into some mice (panel v). Brightfield image indicating mouse positioning is shown in panel i.

Figures 8A, 8B, 8C:
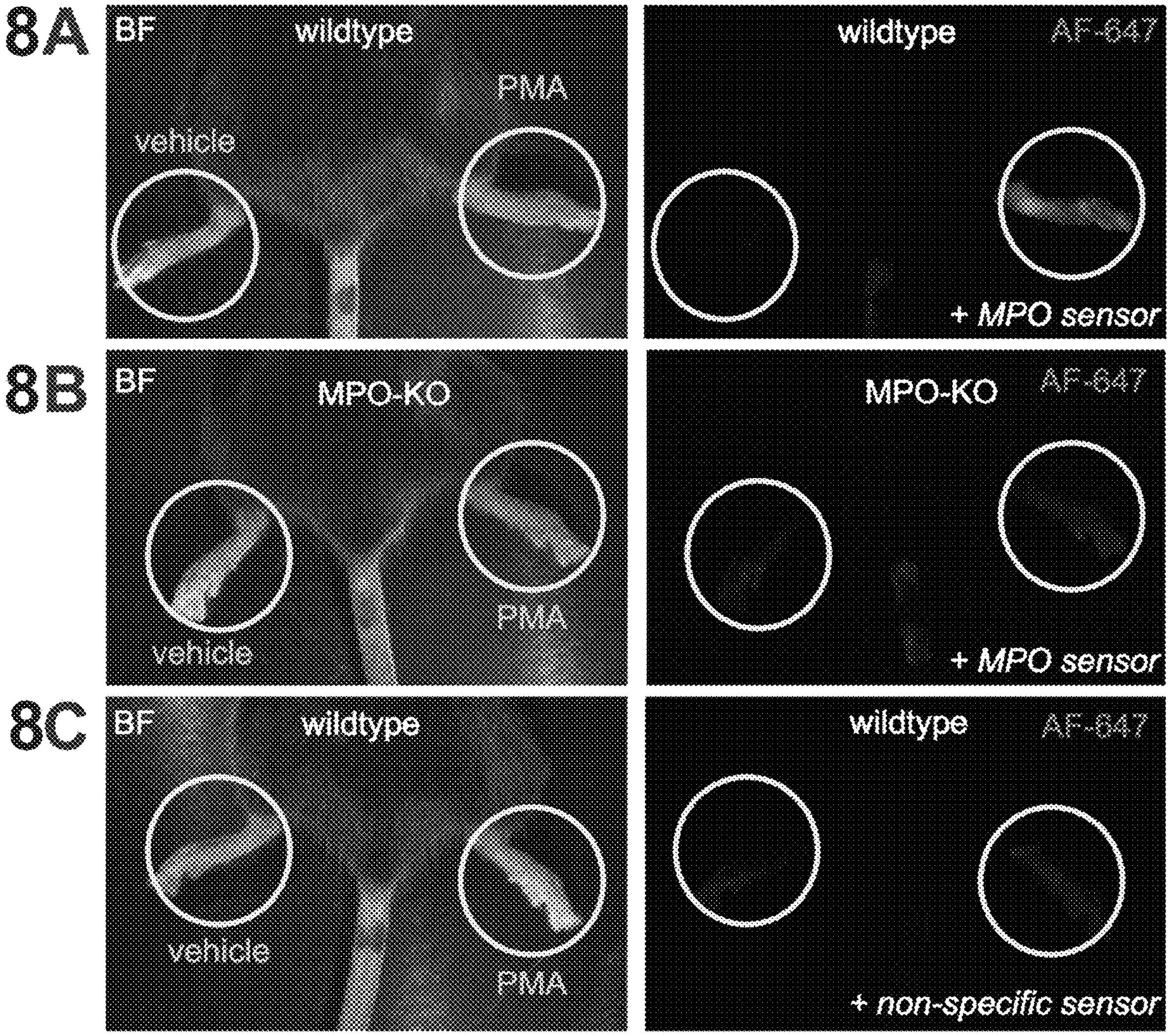

FIGS. 8A-8C shows representative images of mice treated with PMA to induce irritant contact dermatitis on the right hindpaw, and vehicle as negative control on the left hindpaw. Circles outline sites of topical administration of PMA or vehicle. In the left column, brightfield images are presented to outline anatomy. In the right column, fluorescence images of MPO activity are presented. A wildtype mouse injected with Compound 3 demonstrates increased fluorescence in the right (PMA treated) hindpaw (top row). In a MPO-KO mouse injected with Compound 3 (middle row) and a wildtype mouse injected with non-specific control sensor (bottom row), no fluorescence signal over background was detected.

Figure 8D:
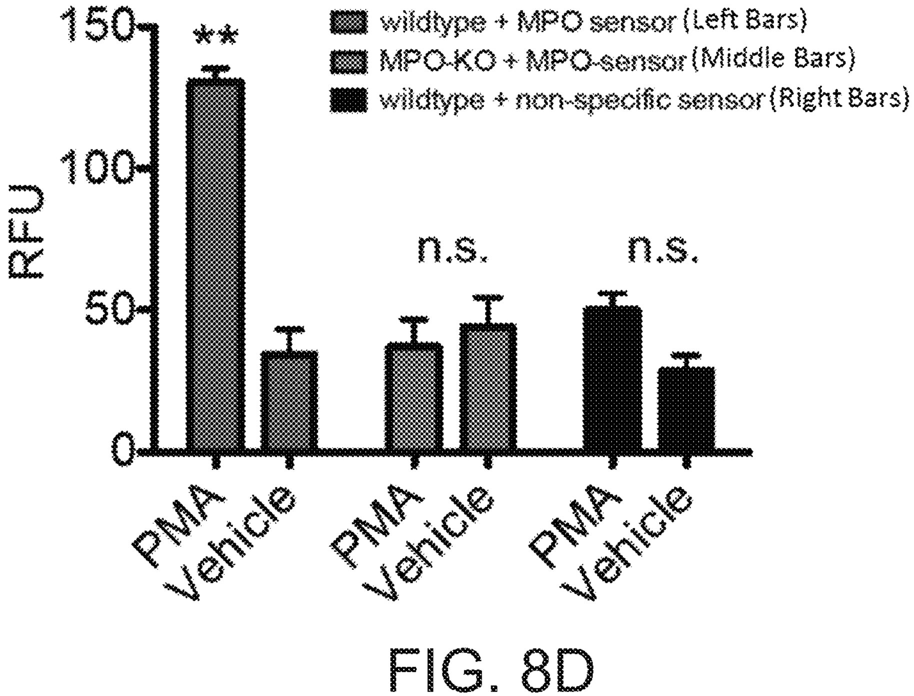

FIG. 8D shows quantification of fluorescence signal in the hindpaws of PMA and vehicle-treated mice. (**$p<0.01$, n.s. not significant).

Figures 9A, 9B, 9C:
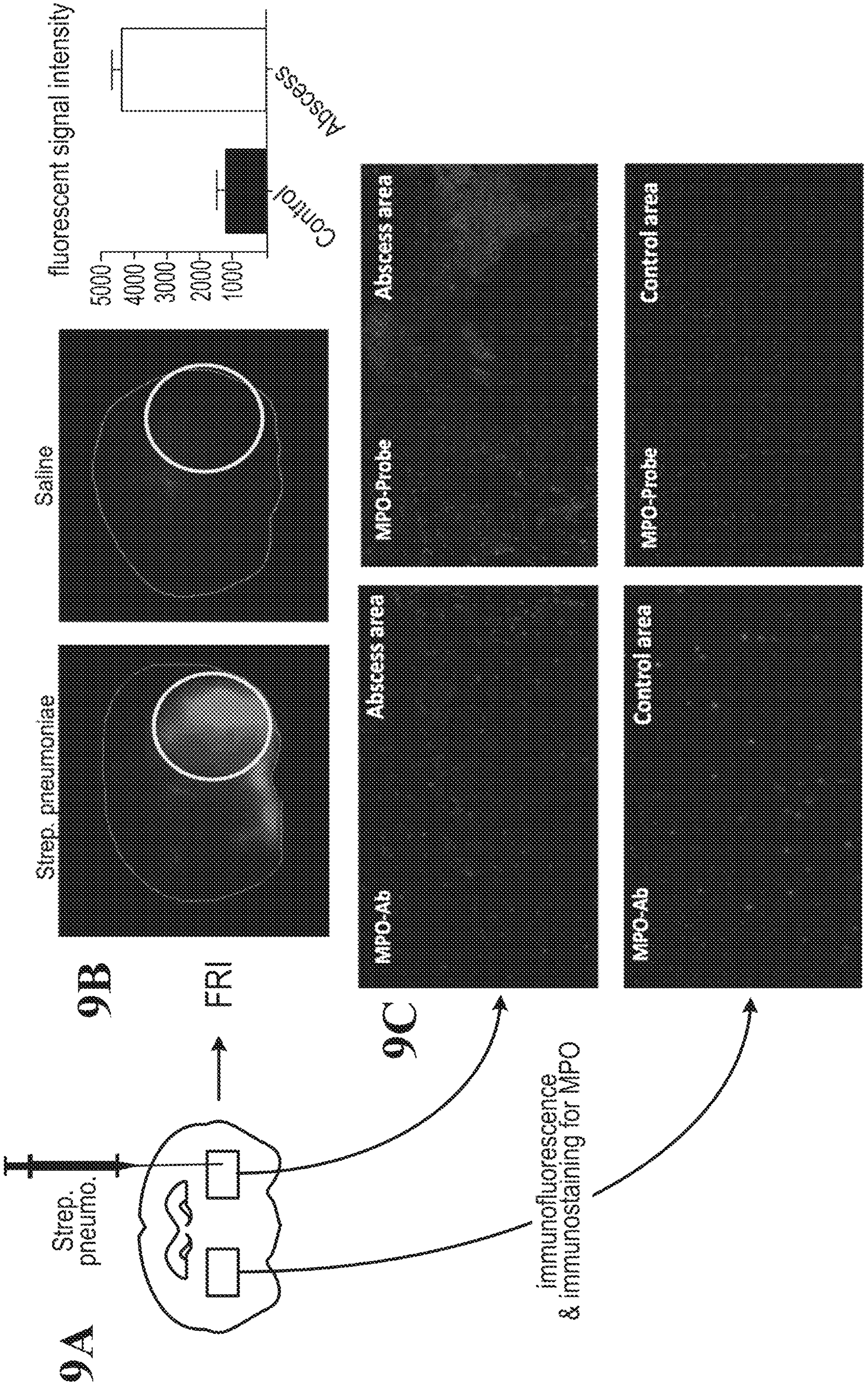

FIGS. 9A-9C Mice were injected with salmonella intracerebrally to induce abscess formation (FIG. 9A). Fluorescence reflectance imaging of coronal brain slices was performed (FIG. 9B), indicating fluorescence signal consistent with MPO activity in the ipsilateral but not contralateral hemisphere. Saline injection did not trigger significant MPO activity. Correlation between MPO activity from Compound 3 and MPO protein as detected with an MPO-antibody revealed increased MPO protein in both ipsi- and contralateral hemispheres (FIG. 9C). MPO activity was only detected in the ipsilateral hemisphere. Also, areas of MPO protein but no activity were seen in the ipsilateral hemisphere.

Figure 10A:
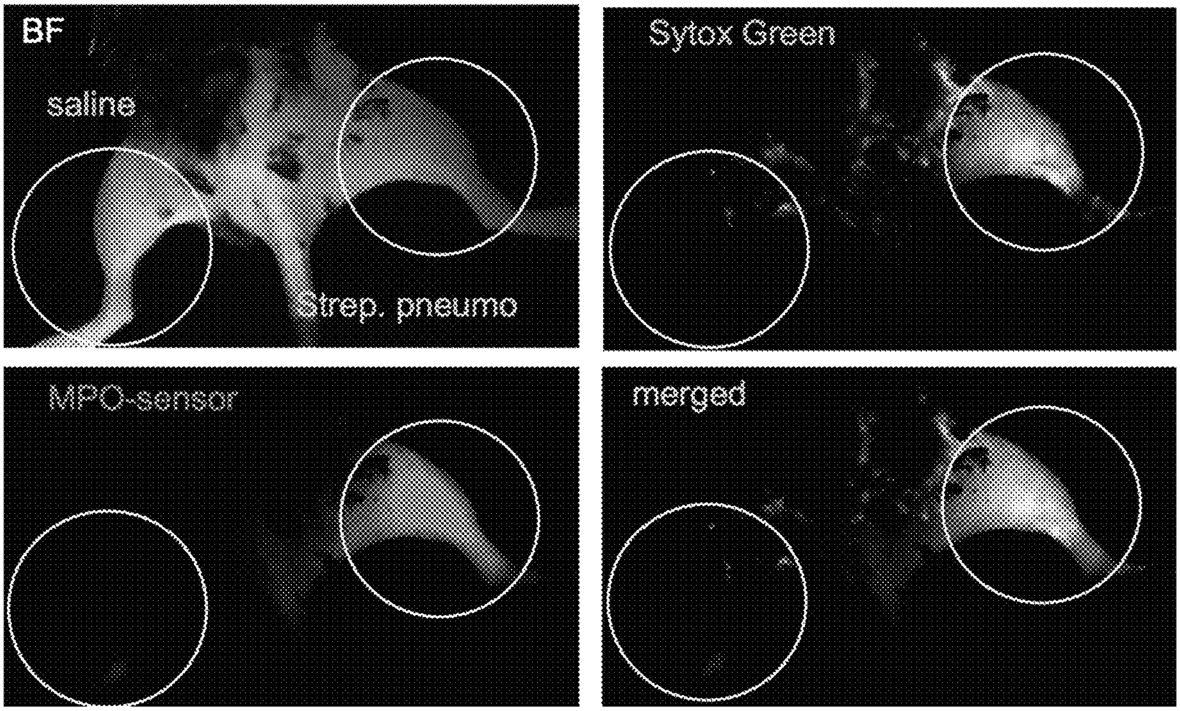

FIG. 10A shows representative fluorescent images of mice were injected subcutaneously with *Streptococcus pneumoniae* (SPn) to induce bacterial cellulitis with formation of NETs, or with saline as a negative control. Circles outline sites of SPn or vehicle injections. A brightfield image (for anatomical reference) and fluorescence images of MPO-sensor (MPO activity) and Sytox Green (extracellular DNA) as well as a merged fluorescence image (MPO-sensor plus Sytox Green) are presented. Colocalization of MPO activity with extracellular DNA is consistent with NET formation at the site of infection.

Figure 10B:
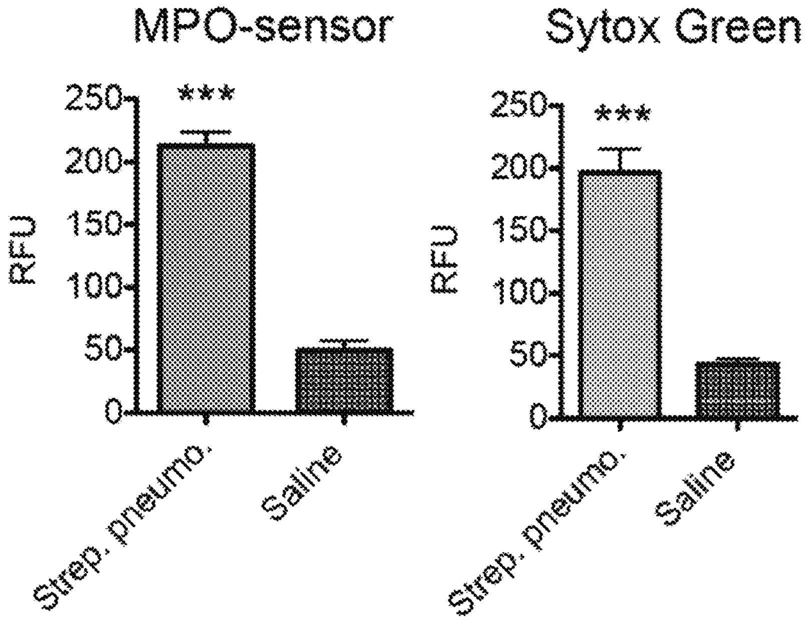

FIG. 10B shows increased levels of MPO activity and extracellular DNA seen in the SPn injected thigh but not the saline injected thigh (***$p<0.001$).

Figure 11:
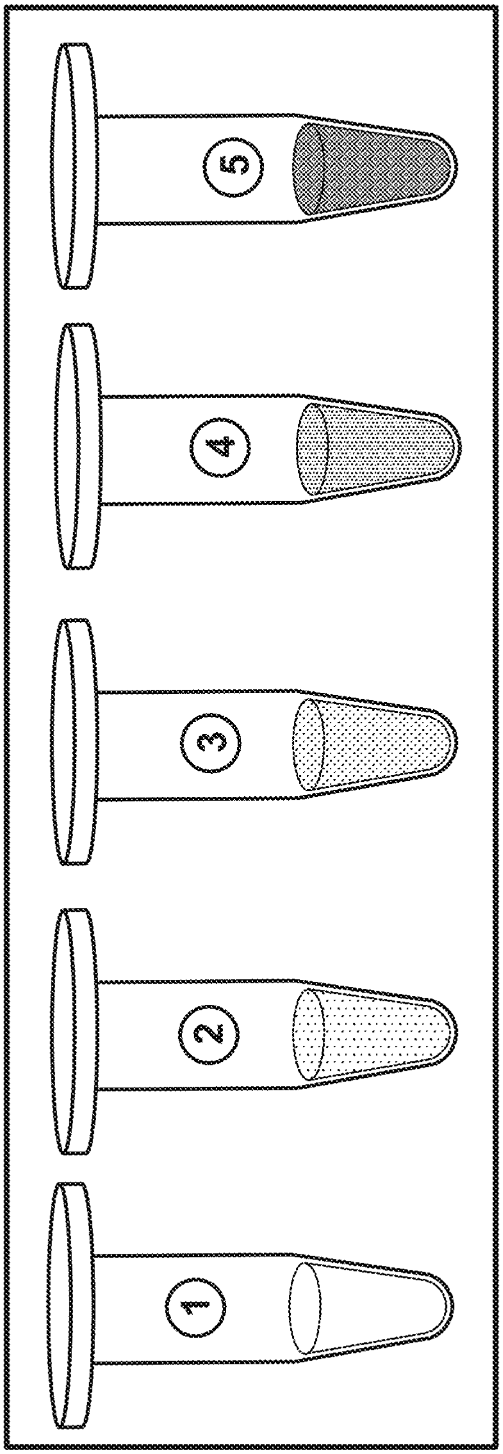

FIG. 11 shows representative results of the in vitro color change experiment described in Example 15. No color change was observed when no MPO was added (Vial No. 2). Horseradish peroxidase (HRP) and MPO can oxidize the PET agent, which underwent oligomerization to cause color change when combined with $H_2O_2$ or glucose/GOX (equivalent of $H_2O_2$) (Vial Nos. 3, 4, 5).

Figure 12:
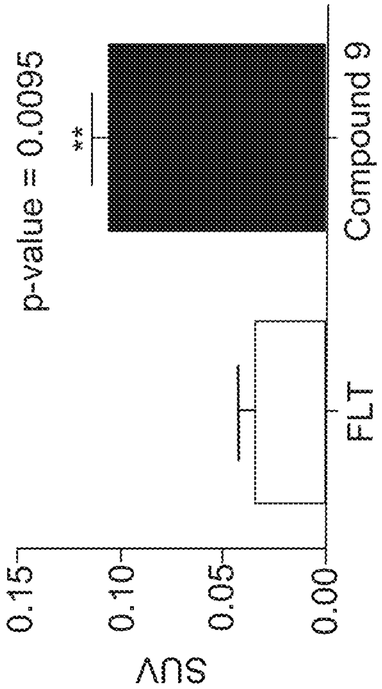

FIG. 12 shows standardized uptake value (SUV) of 3'-deoxy-3'-18F-fluorothymidine (18F-FLT) and Compound 9 in the brain.

DETAILED DESCRIPTION

MPO has been detected in a variety of acute and chronic inflammatory diseases including atherosclerosis (see e.g., Brennan et al, 2001, *The Journal of Clinical Investigation,* 107(4):419:430; and Nicholls et al, 2005, *Arteriosclerosis, Thrombosis, and Vascular Biology,* 25(6):1102-1111), Alzheimer' disease (see e.g., Maki et al, *The Journal of Biological Chemistry,* 2009, 284(5):3158-3169; and Reynolds et al, *Experimental Neurology,* 1999, 155(1);31-41), stroke (see e.g., Forghani et al, *Journal of cerebral blood flow and metabolism: Official Journal of the International Society of Cerebral Blood Flow and Metabolism,* 2015, 35(3):485-493), multiple sclerosis (see e.g. Gray et al, *Neuroscience Letters,* 2008, 444(2):195-198; and Gray et al, *Brain Pathology,* 2008, 18(1):86-95), myocardial infarction (see e.g., Brennan et al, *N. Engl. J. Med.* 2003, 349, 1595-1604), atrial fibrillation (see e.g., Rudolph et al, *Nature Medicine,* 2009, 16(4):470-474), among others and has been recognized as an important biomarker for inflammation. Given its functions in inflammatory processes, several imaging methods to detect MPO activity have been developed, such as luminol (see e.g., Gross et al, *Nature Medicine,* 2009, 15(4)455-461; and Zhang et al, *Nature Medicine,* 2013, 19(4):500-505), oxazine conjugated nanoparticles (see e.g., Panizzi et al, Journal of the American Chemical Society, 2009, 131(43):15739-15744), or SNAPF (sulfonaphthoaminophenyl fluorescein') (see e.g., Shepherd et al, *Chemistry & Biology,* 2007, 14(11):1221-1231). However, inadequate tissue penetration and/or lack of specificity have so far limited the use of these agents in research and translational studies in humans are pending. Previous studies have provided activatable bis-5-HT-DTPA for magnetic resonance imaging (MRI), which have been validated in animal inflammatory disease (see e.g., Chen et al, *Brain: A Journal of Neurology,* 2008, 131(Pt 4):1123-1133; Nahrendorf et al, *Circulation,* 2008, 117(9):1153-1160; and Swirski et al, *The Journal of Clinical Investigation,* 2010, 120(7): 2627-2634). To detect the early inflammatory events and neurological inflammation where the capability of crossing blood-brain barrier is essential, more sensitive imaging modalities are highly desirable.

Herein is provided novel positron emission tomography (PET) and fluorescent imaging probes targeting MPO and their uses in applications related to animal inflammation diseases.

Compounds

The present application provides, infer alia, a compound of Formula VI:

VI

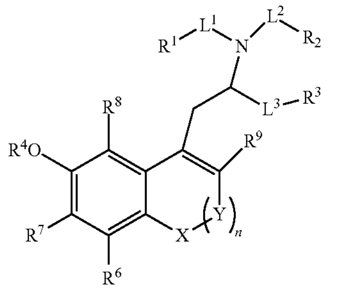

or a pharmaceutically acceptable salt thereof, wherein:

- X is selected from the group consisting of $CH_2$, NH, O, and S;
- Y is selected from the group consisting of $CH_2$, NH, O, and S;
- $L^1$ is selected from the group consisting of a bond, —C(O)—, —C(O)O—, —C(O)N$R^{a1}$—, —(C(O)($C_{1-6}$ alkylene)-, and —C(O)($C_{1-6}$ alkyleneoxy)-;
- $R^1$ is selected from the group consisting of $R^5$, H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;
- $L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, —C(O)O—, —C(O)N$R^{a2}$—, —C(O)($C_{1-6}$ alkylene)-, and —C(O)($C_{1-6}$ alkyleneoxy)-;
- $R^2$ is selected from the group consisting of $R^5$, $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkoxy, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;
- $L^3$ is selected from the group consisting of a bond, —C(O)—, —C(O)O—, —C(O)N$R^{a3}$, —C(O)($C_{1-6}$ alkylene)-, —C(O)($C_{1-6}$ alkyleneoxy)-, —C(O)N($R^{a3}$)($C_{1-6}$ alkylene)-, —C(O)N($R^{a3}$)($C_{1-6}$ alkylene)-di($C_{1-6}$ alkyl)amino, and —C(O)N($R^{a3}$)($C_{1-6}$ alkyleneoxy)-;
- $R^3$ is selected from the group consisting of $R^5$, H, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, 5-10 membered heteroaryl, and —C(O)N($R^{a3}$)($C_{1-6}$ haloalkoxy), wherein each $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, 5-10 membered heteroaryl, is optionally substituted by 1, 2, 3, or 4 substituents independently selected from OH, halo, $C_{1-6}$ alkoxy, and $C_{1-6}$ haloalkyl;
- or alternatively, -$L^3$-$R^3$ forms an oxo group;
- $R^4$ is selected from the group consisting of H, $C_{1-6}$ alkyl, $C_{2-6}$ alkenyl, $C_{2-6}$ alkynyl, and $C_{1-6}$ haloalkyl;
- each $R^5$ is independently selected from the group consisting of a nanoparticle (e.g., dextran, a dendrimer, cross-linked iron oxide (CLIO), nanogold, a quantum dot, and the like), and a biological molecule (e.g., a protein, a polypeptide, a recombinant functional biological molecule, and the like);
- $R^6$, $R^7$, $R^8$, and $R^9$ are each independently selected from the group consisting of H, $C_{1-40}$ alkyl, $C_{2-40}$ alkenyl, $C_{2-40}$ alkynyl, $C_{1-40}$ alkoxy, $C_{1-40}$ haloalkyl, and $C_{1-40}$ haloalkoxy, —NH($C_{1-40}$ alkyl), and —N($C_{1-40}$ alkyl)$_2$;
- each $R^{a1}$; $R^{a2}$, and $R^{a3}$ is independently selected from the group consisting of H, $C_{1-6}$ alkyl, $C_{2-6}$ alkenyl, $C_{2-6}$ alkynyl, and $C_{1-6}$ haloalkyl; and
- n is 0, 1, or 2.

In some embodiments, n is 0. In some embodiments, n is 1. In some embodiments, n is 2.

In some embodiments, X is NH.

In some embodiments, $R^6$, $R^7$, $R^8$, and $R^9$ are each independently selected from the group consisting of $C_{1-20}$ alkyl, $C_{2-20}$ alkenyl, $C_{2-20}$ alkynyl, $C_{1-20}$ alkoxy, $C_{1-20}$ haloalkyl, $C_{1-20}$ haloalkoxy, —NH($C_{1-20}$ alkyl), and —N($C_{1-20}$ alkyl)$_2$. In some embodiments, $R^6$, $R^7$, $R^8$, and $R^9$ are each independently selected from the group consisting of H, $C_{1-10}$ alkyl, $C_{2-10}$ alkenyl, $C_{2-10}$ alkynyl, $C_{1-10}$ alkoxy, $C_{1-10}$ haloalkyl, $C_{1-10}$ haloalkoxy, —NH($C_{1-10}$ alkyl), and —N($C_{1-10}$ alkyl)$_2$. In some embodiments, $R^6$, $R^7$, $R^8$, and $R^9$ are each independently selected from the group consisting of H, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, —NH($C_{1-6}$ alkyl), and —N($C_{1-6}$ alkyl)$_2$. In some embodiments, $R^6$, $R^7$, $R^8$, and $R^9$ are each independently selected from the group consisting of H, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, —NH($C_{1-6}$ alkyl), and —N($CH_3$)($C_{1-6}$ alkyl).

In some embodiments, $R^6$ is H.

In some embodiments, $R^7$ is H.

In some embodiments, $R^8$ is H.

In some embodiments, $R^9$ is H.

In some embodiments, $R^6$, $R^7$, $R^8$ and $R^9$ are each H.

In some embodiments, the compound of Formula VI, or a pharmaceutically acceptable salt thereof, is a compound of Formula I:

I

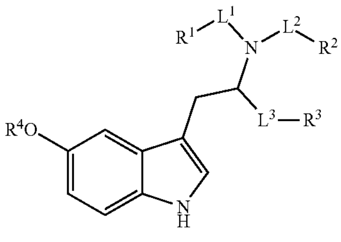

or a pharmaceutically acceptable salt thereof, wherein:

- $L^1$ is selected from the group consisting of a bond, —C(O)—, —C(O)O—, —C(O)N$R^{a1}$—, —C(O)($C_{1-6}$ alkylene)-, and —C(O)($C_{1-6}$ alkyleneoxy)-;
- $R^1$ is selected from the group consisting of $R^5$, H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl wherein each $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterorycloalkylene)-, —($C_{1-6}$ alkylene)-(5-10 membered heteroarylene)-, —C(O)—, —C(O)O—, —C(O)$NR^{a2}$—, —C(O)($C_{1-6}$ alkylene)-, and —C(O)($C_{1-6}$ alkyleneoxy)-;

$R^2$ is selected from the group consisting of $R^5$, $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkoxy, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^3$ is selected from the group consisting of a bond, —C(O)—, —C(O)O—, —C(O)$NR^{a3}$—, —C(O)($C_{1-6}$ alkylene)-, —C(O)($C_{1-6}$ alkyleneoxy)-, —C(O)N($R^{a3}$)($C_{1-6}$ alkylene)-, —C(O)N($R^{a3}$)($C_{1-6}$ alkylene)-di($C_{1-6}$ alkyl)amino, and —C(O)N($R^{a3}$)($C_{1-6}$ alkyleneoxy)-;

$R^3$ is selected from the group consisting of $R^5$, H, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, 5-10 membered heteroaryl, and —C(O)N($R^{a3}$)($C_{1-6}$ haloalkoxy), wherein each $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, 5-10 membered heteroaryl, is optionally substituted by 1, 2, 3, or 4 substituents independently selected from OH, halo, $C_{1-6}$ alkoxy, and $C_{1-6}$ haloalkyl;

or alternatively, -$L^3$-$R^3$ forms an oxo group;

$R^4$ is selected from the group consisting of H, $C_{1-6}$ alkyl, $C_{2-6}$ alkenyl $C_{2-6}$ alkynyl, and $C_{1-6}$ haloalkyl;

each $R^5$ is independently selected from the group consisting of a nanoparticle (e.g., dextran, a dendrimer, cross-linked iron oxide (CLIO), nanogold, a quantum dot, and the like), and a biological molecule (e.g., a protein, a polypeptide, a recombinant functional biological molecule, and the like); and each $R^{a1}$, $R^{a2}$, and $R^{a3}$ is independently selected from the group consisting of H, $C_{1-6}$ alkyl, $C_{2-6}$ alkenyl, $C_{2-6}$ alkynyl, and $C_{1-6}$ haloalkyl.

In some embodiments:

$L^1$ is selected from the group consisting of a bond, —C(O)—, —C(O)O—, —C(O)$NR^{a1}$—, —C(O)($C_{1-6}$ alkylene)-, and —C(O)($C_{1-6}$ alkyleneoxy)-;

$R^1$ is selected from the group consisting of H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, —C(O)O—, —C(O)$NR^{a2}$—, —C(O)($C_{1-6}$ alkylene)-, and —C(O)($C_{1-6}$ alkyleneoxy)-;

$R^2$ is selected from the group consisting of $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkoxy, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^3$ is selected from the group consisting of a bond, —C(O)—, —C(O)O—, —C(O)$NR^{a3}$—, —C(O)($C_{1-6}$ alkylene)-, —C(O)($C_{1-6}$ alkyleneoxy)-, —C(O)N($R^{a3}$)($C_{1-6}$ alkylene)-, —C(O)N($R^{a3}$)($C_{1-6}$ alkylene)-di($C_{1-6}$ alkyl)amino, and —C(O)N($R^{a3}$)($C_{1-6}$ alkyleneoxy)-;

$R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, 5-10 membered heteroaryl, and —C(O)N($R^{a3}$)($C_{1-6}$ haloalkoxy), wherein each $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl 5-10 membered heteroaryl, is optionally substituted by 1, 2, 3, or 4 substituents independently selected from OH, halo, $C_{1-6}$ alkoxy, and $C_{1-6}$ haloalkyl;

or alternatively, -$L^3$-$R^3$ forms an oxo group;

$R^4$ is selected from the group consisting of H, $C_{1-6}$ alkyl, $C_{2-6}$ alkenyl, $C_{2-6}$ alkynyl, and $C_{1-6}$ haloalkyl;

and each $R^{a1}$, $R^{a2}$, and $R^{a3}$ is independently selected from the group consisting of H, $C_{1-6}$ alkyl, $C_{2-6}$ alkenyl, $C_{2-6}$ alkynyl, and $C_{1-6}$ haloalkyl.

In some embodiments:

$L^1$ is selected from the group consisting of a bond, —C(O)—, —C(O)O—, —C(O)$NR^{a1}$—, —C(O)($C_{1-6}$ alkylene)-, and —C(O)($C_{1-6}$ alkyleneoxy)-;

$R^1$ is selected from the group consisting of H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{3-0}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, —C(O)O—, —C(O)$NR^{a2}$—, —C(O)($C_{1-6}$ alkylene)-, and —C(O)($C_{1-6}$ alkyleneoxy)-;

$R^2$ is selected from the group consisting of $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkoxy, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^3$ is selected from the group consisting of a bond, —C(O)—, —C(O)O—, —C(O)$NR^{a3}$—, —C(O)($C_{1-6}$ alkylene)-, —C(O)($C_{1-6}$ alkyleneoxy)-, —C(O)N($R^{a3}$)($C_{1-6}$ alkylene)-, and —C(O)N($R^{a3}$)($C_{1-6}$ alkyleneoxy)-;

$R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{1-6}$ alkoxy, $C_{3-10}$ cycloalkyl, $C_{6-10}$ aryl, 4-10 membered heterocycloalkyl, and 5-10 membered heteroaryl, is optionally substituted by 1, 2, 3, or 4 substituents independently selected from OH, halo, $C_{1-6}$ alkoxy, and $C_{1-6}$ haloalkyl;

or alternatively, $-L^3-R^3$ forms an oxo group;

$R^4$ is selected from the group consisting of H, $C_{1-6}$ alkyl, $C_{2-6}$ alkenyl, $C_{2-6}$ alkenyl, and $C_{1-6}$ haloalkyl;

and each $R^{a1}$, $R^{a2}$, and $R^{a3}$ is independently selected from the group consisting of H, $C_{1-6}$ alkyl, $C_{2-6}$ alkenyl, $C_{2-6}$ alkynyl, and $C_{1-6}$ haloalkyl.

In some embodiments, $L^1$ is selected from the group consisting of a bond, —C(O)—, —C(O)($C_{1-6}$ alkylene)-, and —C(O)($C_{1-6}$ alkyleneoxy)-. In some embodiments, $L^1$ is selected from the group consisting of a bond and —C(O)($C_{1-6}$ alkylene)-. In some embodiments, $L^1$ is a bond. In some embodiments, $L^1$ is —C(O)($C_{1-6}$ alkylene)-. In some embodiments, $L^1$ is —C(O)(n-butylene)-.

In some embodiments, $R^1$ is selected from the group consisting of H, $C_{3-10}$ cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^1$ is selected from the group consisting of H and 4-10 membered heterocycloalkyl, wherein the 4-10 membered heterocycloalkyl is optionally substituted by 1, 2, 3, or 4 substituents independently selected from OH, halo, $C_{1-6}$ alkoxy, and $C_{1-6}$ haloalkyl. In some embodiments, $R^1$ is selected from the group consisting of H and a bicyclic 8-10 membered heterocycloalkyl, wherein the bicyclic 8-10 membered heterocycloalkyl is optionally substituted by 2, 3, or 4 substituents independently selected from OH, halo, $C_{1-6}$ alkoxy, and $C_{1-6}$ haloalkyl.

In some embodiments, $R^1$ is a 4-10 membered heterocycloalkyl, wherein the 4-10 membered heterocycloalkyl is optionally substituted by 1, 2, 3, or 4 substituents independently selected from OH, halo, $C_{1-6}$ alkoxy, and $C_{1-6}$ haloalkyl. In some embodiments, $R^1$ is a 4-10 membered heterocycloalkyl, wherein the 4-10 membered heterocycloalkyl is unsubstituted. In some embodiments, $R^1$ is a bicyclic 8-10 membered heterocycloalkyl, wherein the bicyclic 8-10 membered heterocycloalkyl is unsubstituted. In some embodiments, $R^1$ is selected from H and

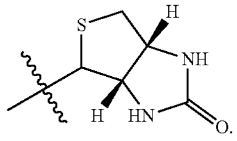 [SMILES: *C1SC[C@@H]2NC(=O)N[C@H]12]

In some embodiments, $R^1$ is H. In some embodiments, $R^1$ is:

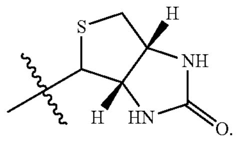 [SMILES: *C1SC[C@@H]2NC(=O)N[C@H]12]

In some embodiments, $R^1$ is $R^5$.

In some embodiments, $L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, and —C(O)($C_{1-6}$ alkylene)-.

In some embodiments, $L^2$ is selected from the group consisting of —($C_{1-6}$ alkylene)-(5-10 membered heteroarylene)-; —C(O)—, and —C(O)($C_{1-6}$ alkylene)-. In some embodiments, $L^2$ is selected from the group consisting of —$CH_2$-(5-10 membered heteroarylene)-, —C(O)—, —C(O)$CH_2$—, and —C(O)$CH_2CH_2CH_2CH_2$—. In some embodiments, $L^2$ is selected from the group consisting of —$CH_2$-(5-6 membered heteroarylene)-, —C(O)—, —C(O)$CH_2$—, and —C(O)$CH_2CH_2CH_2CH_2$—. In some embodiments, $L^2$ is selected from the group consisting of —($C_{1-6}$ alkylene)-(triazolyl)-, —C(O)—, and —C(O)($C_{1-6}$ alkylene)-. In some embodiments, $L^2$ is selected from the group consisting of —$CH_2$-(triazolyl)-, —C(O)—, and —C(O)$CH_2$—, and —C(O)(n-butylene)-.

In some embodiments, $R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by one substituent independently selected from OH, halo, $C_{1-6}$ alkoxy, and $C_{1-6}$ haloalkyl.

In some embodiments, $R^2$ is selected from the group consisting of $C_{1-6}$ alkoxy, phenyl, bicyclic 8-10 membered heterocycloalkyl, and bicyclic 8-10 membered heteroaryl, wherein each $C_{1-6}$ alkoxy, phenyl, bicyclic 8-10 membered heterocycloalkyl, and 8-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^2$ is selected from the group consisting of $C_{1-6}$ alkoxy, phenyl, bicyclic 8-10 membered heterocycloalkyl, and bicyclic 8-10 membered heteroaryl, wherein each $C_{1-6}$ alkoxy, phenyl, bicyclic 8-10 membered heterocycloalkyl, and 8-10 membered heteroaryl is optionally substituted by one substituent independently selected from OH, halo, $C_{1-6}$ alkoxy, and $C_{1-6}$ haloalkyl.

In some embodiments, $R^2$ is $C_{1-6}$ alkoxy, wherein the $C_{1-6}$ alkoxy is substituted by $C_{1-6}$ haloalkyl. In some embodiments, $R^2$ is $C_{1-6}$ alkoxy, wherein the $C_{1-6}$ alkoxy is substituted by —$CH_2CH_2F$. In some embodiments, the $C_{1-6}$ alkoxy is —$CH_2CH_2O$—$CH_2CH_2O$—. In some embodiments, $R^2$ is —$CH_2CH_2OCH_2CH_2OCH_2CH_2F$.

In some embodiments, R is $C_{6-10}$ aryl, wherein the $C_{6-10}$ aryl is substituted by one halo group. In some embodiments, $R^2$ is phenyl, wherein the phenyl is substituted by one halo, group. In some embodiments, $R^2$ is phenyl, wherein the phenyl is substituted by fluoro. In some embodiments, the fluoro is [$^{18}$F]. In some embodiments, $R^2$ is 4-fluorophenyl. In some embodiments, $R^2$ is 4-[$^{18}$F]phenyl.

In some embodiments, $R^2$ is a 4-10 membered heterocycloalkyl, wherein the 4-10 membered heterocycloalkyl is optionally substituted by 1, 2, 3, or 4 substituents independently selected from OH, halo, and $C_{1-6}$ haloalkyl. In some embodiments, $R^2$ is a 4-10 membered heterocycloalkyl, wherein the 4-10 membered heterocycloalkyl is unsubstituted. In some embodiments, $R^2$ is a bicyclic 8-10 membered heterocycloalkyl, wherein the bicyclic 8-10 membered heterocycloalkyl is unsubstituted. In some embodiments, $R^2$ is:

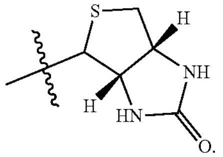 [SMILES: *C1SC[C@@H]2NC(=O)N[C@H]12]

In some embodiments, $R^2$ is a 5-10 membered heteroaryl group, wherein the 5-10 membered heteroaryl is optionally substituted by one OH group. In some embodiments, $R^2$ is an 8-10 membered heteroaryl group, wherein the 8-10 membered heteroaryl is optionally substituted by one OH group. In some embodiments, $R^2$ is a bicyclic 8-10 membered heteroaryl group, wherein the bicyclic 8-10 membered heteroaryl is optionally substituted by one OH group. In some embodiments, $R^2$ is an indole group, wherein the indole is optionally substituted by one OH group. In some embodiments, $R^2$ is 5-hydroxyindole. In some embodiments, $R^2$ is $R^5$.

In some embodiments, $L^3$ is selected from the group consisting of a bond, —C(O)$NR^{a3}$, —C(O)N($R^{a3}$)($C_{1-6}$ alkylene)-, —C(O)N($R^{a3}$)($C_{1-6}$ alkylene)-di($C_{1-6}$ alkyl)amino, and —C(O)N($R^{a3}$)($C_{1-6}$ alkyleneoxy)-. In some embodiments, $L^3$ is selected from the group consisting of a bond, —C(O)N($R^{a3}$)($C_{1-6}$ alkylene)-, —C(O)N($R^{a3}$)($C_{1-6}$ alkylene)-di($C_{1-6}$ alkyl)amino, and —CO)N($R^{a3}$)($C_{1-6}$ alkyleneoxy)-. In some embodiments, $L^3$ is selected from the group consisting of a bond, —C(O)NH($C_{1-6}$alkylene)-, —C(O)NH($C_{1-6}$ alkylene)-N($CH_3$)$_2$, and —C(O)NH($C_{1-6}$ alkyleneoxy)-.

In some embodiments, $L^3$ is selected from the group consisting of a bond, —C(O)$NR^{a3}$—, —C(O)N($R^{a3}$)($C_{1-6}$ alkylene)-, and —C(O)N($R^{a3}$)($C_{1-6}$ alkyleneoxy)-. In some embodiments, $L^3$ is selected from the group consisting of a bond, —C(O)N($R^{a3}$)($C_{1-6}$ alkylene)-, and —C(O)N($R^{a3}$)($C_{1-6}$ alkyleneoxy)-. In some embodiments, $L^3$ is selected from the group consisting of a bond, —C(O)NH($C_{1-6}$ alkylene)-, and —CO)NH($C_{1-6}$ alkyleneoxy)-. In some embodiments, $L^3$ is a bond. In some embodiments, $L^3$ is —C(O)NH($C_{1-6}$ alkylene)-. In some embodiments, $L^3$ is —C(O)NH(hexylene)-. In some embodiments, $L^3$ is —C(O)NH($C_{1-6}$ alkyleneoxy)-. In some embodiments, $L^3$ is —C(O)$NHCH_2CH_2OCH_2CH_2O$—. In some embodiments, $L^3$ is —C(O)N($R^{a3}$)($C_{1-6}$ alkylene)-di($C_{1-6}$ alkyl)amino. In some embodiments, $L^3$ is —C(O)NH($C_{1-6}$ alkylene)-N($CH_3$)$_2$.

In some embodiments, $R^3$ is selected from the group consisting of H, $C_{1-6}$ haloalkyl, $C_{3-10}$ cycloalkyl, $C_{6-10}$ aryl, 4-10 membered heterocycloalkyl, 5-10 membered heteroaryl, and —C(O)N($R^{a3}$)($C_{1-6}$ haloalkoxy), wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^3$ is selected from the group consisting of H, $C_{1-6}$ haloalkyl, 5-10 membered heteroaryl, and —C(O)N($R^{a3}$)($C_{1-6}$ haloalkoxy), wherein each $C_{1-6}$ haloalkyl and 5-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^3$ is selected from the group consisting of H, $C_{1-6}$ haloalkyl, 5-10 membered heteroaryl, and —C(O)N($R^{a3}$)($C_{1-6}$ haloalkoxy), wherein each $C_{1-6}$ haloalkyl, and 5-10 membered heteroaryl is optionally substituted by one substituent independently selected from OH, halo, $C_{1-6}$ alkoxy, and $C_{1-6}$ haloalkyl.

In some embodiments, $R^3$ is selected from the group consisting of H, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^3$ is selected from the group consisting of H, $C_{1-6}$ haloalkyl, and 5-10 membered heteroaryl, wherein each $C_{1-6}$ haloalkyl, and 5-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^3$ is selected from the group consisting of H, $C_{1-6}$ haloalkyl, and 5-10 membered heteroaryl, wherein each $C_{1-6}$ haloalkyl, and 5-10 membered heteroaryl is optionally substituted by one substituent independently selected from OH, halo, $C_{1-6}$ alkoxy, and $C_{1-6}$ haloalkyl.

In some embodiments, $R^3$ is selected from the group consisting of H, $C_{1-6}$ haloalkyl, a bicyclic 8-10 membered heteroaryl, and —C(O)N($R^{a3}$)($C_{1-6}$ haloalkoxy), wherein each $C_{1-6}$ haloalkyl, and bicyclic 8-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^3$ is selected from the group consisting of H, $C_{1-6}$ haloalkyl, bicyclic 8-10 membered heteroaryl, and —C(O)N($R^{a3}$)($C_{1-6}$ haloalkoxy), wherein each $C_{1-6}$ haloalkyl, and bicyclic 8-10 membered heteroaryl is optionally substituted by one substituent independently selected from OH, halo, $C_{1-6}$ alkoxy, and $C_{1-6}$ haloalkyl. In some embodiments, $R^3$ is selected from the group consisting of H, $C_{1-6}$ haloalkyl, bicyclic 8-10 membered heteroaryl, and —C(O)N($R^{a3}$)($C_{1-6}$ haloalkoxy), wherein the 8-10 membered heteroaryl is optionally substituted by one OH group.

In some embodiments, $R^3$ is selected from the group consisting of H, $C_{1-6}$ haloalkyl, and a bicyclic 8-10 membered heteroaryl, wherein each $C_{1-6}$ haloalkyl, and bicyclic 8-10 membered heteroaryl is optionally substituted by 1, 2, 3, or 4 substituents independently selected from OH, halo, $C_{1-6}$ alkoxy, and $C_{1-6}$ haloalkyl. In some embodiments, $R^3$ is selected from the group consisting of H, $C_{1-6}$ haloalkyl, and bicyclic 8-10 membered heteroaryl, wherein each $C_{1-6}$ haloalkyl, and bicyclic 8-10 membered heteroaryl is optionally substituted by one substituent independently selected from OH, halo, $C_{1-6}$ alkoxy, and $C_{1-6}$ haloalkyl. In some embodiments, $R^3$ is selected from the group consisting of H, $C_{1-6}$ haloalkyl, and bicyclic 8-10 membered heteroaryl, wherein the 8-10 membered heteroaryl is optionally substituted by one OH group.

In some embodiments, $R^3$ is H. In some embodiments, $R^3$ is $C_{1-6}$ haloalkyl. In some embodiments, $R^3$ is $C_{1-4}$ haloalkyl. In some embodiments, $R^3$ is —$CH_2CH_2F$. In some embodiments, $R^3$ is a 5-10 membered heteroaryl which is optionally substituted by one substituent independently selected from OH, halo, $C_{1-6}$ alkoxy, and $C_{1-6}$ haloalkyl. In some embodiments, $R^3$ is a bicyclic 8-10 membered heteroaryl which is optionally substituted by one substituent independently selected from OH, halo, $C_{1-6}$ alkoxy, and $C_{1-6}$ haloalkyl. In some embodiments, $R^3$ is a bicyclic 8-10 membered heteroaryl which is optionally substituted by one OH group. In some embodiments, $R^3$ is an indole group, wherein the indole is optionally substituted by one OH group. In some embodiments, $R^3$ is 5-hydroxyindole. In some embodiments, $R^3$ is —C(O)N($R^{a3}$)($C_{1-6}$ haloalkoxy). In some embodiments, $R^3$—C(O)NH($C_{1-6}$ haloalkoxy). In some embodiments, $R^3$ is —C(O)

$NHCH_2CH_2OCH_2CH_2OCH_2CH_2F$. In some embodiments, $R^3$ is —C(O)$NHCH_2CH_2OCH_2CH_2OCH_2CH_2$-$^{18}F$. In some embodiments, $R^3$ is $R^5$.

In some embodiments, -$L^3$-$R^3$ forms an oxo group (i.e. =O).

In some embodiments, $R^4$ is H.

In some embodiments, $R^1$, $R^2$, and $R^3$ are each an independently selected $R^5$ group. In some embodiments, $R^1$, $R^2$, and $R^3$ are each the same $R^5$ group.

In some embodiments, each $R^{a1}$, $R^{a2}$ and $R^{a3}$ is H.

In some embodiments:

$L^1$ is selected from the group consisting of a bond, —C(O)—, —C(O)($C_{1-6}$ alkylene)-, and —C(O)($C_{1-6}$ alkyleneoxy)-;

$R^1$ is selected from the group consisting of H, $C_{3-10}$ cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered, heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)$NR^{a3}$—, —C(O)N($R^{a3}$)($C_{1-6}$ alkylene)-, —C(O)N($R^{a3}$)($C_{1-6}$ alkylene)-di($C_{1-6}$ alkyl)amino, and —C(O)N($R^{a3}$)($C_{1-6}$ alkyleneoxy)-; and $R^3$ is selected from the group consisting of H, $C_{1-6}$ haloalkyl, $C_{3-10}$ cycloalkyl, $C_{6-10}$ aryl, 4-10 membered heterocycloalkyl, 5-10 membered heteroaryl, and —C(O)N($R^{a3}$)($C_{1-6}$ haloalkoxy), wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

or alternatively, -$L^3$-$R^3$ forms an oxo group.

In some embodiments:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by 1, 2, 3, or 4 substituents independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$)($C_{1-6}$alkylene)-, —C(O)N($R^{a3}$)($C_{1-6}$ alkylene)-di($C_{1-6}$ alkyl)amino, and —C(O)N($R^{a3}$)($C_{1-6}$ alkyleneoxy)-; and $R^3$ is selected from the group consisting of H, $C_{1-6}$ haloalkyl, 5-10 membered heteroaryl, and —C(O)N($R^{a3}$)($C_{1-6}$ haloalkoxy), wherein each $C_{1-6}$ haloalkyl, and 5-10 membered heteroaryl is optionally substituted by 1, 2, 3, or 4 substituents independently selected from OH, halo, and $C_{1-6}$ haloalkyl;

or alternatively, -$L^3$-$R^3$ forms an oxo group.

In some embodiments:

$L^1$ is selected from the group consisting of a bond and —C(O)($C_{1-6}$alkylene)-;

$R^1$ is selected from the group consisting of H and 4-10 membered heterocycloalkyl, wherein the 4-10 membered heterocycloalkyl is optionally substituted by one substituent independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by one substituent independently selected from OH, halo, and $C_{1-6}$ haloalkyl;

$L^3$ is selected from the group consisting of a bond, —C(O)N($R^{a3}$)($C_{1-6}$alkylene)-, —C(O)N($R^{a3}$)($C_{1-6}$ alkylene)-di($C_{1-6}$ alkyl)amino, and —C(O)N($R^{a3}$)($C_{1-6}$ alkyleneoxy)-; and $R^3$ is selected from the group consisting of H, $C_{1-6}$ haloalkyl, 5-10 membered heteroaryl, and —C(O)N($R^{a3}$)($C_{1-6}$ haloalkoxy), wherein each $C_{1-6}$ haloalkyl, and 5-10 membered heteroaryl is optionally substituted by one substituent independently selected from OH, halo, and $C_{1-6}$ haloalkyl;

or alternatively, -$L^3$-$R^3$ forms an oxo group.

In some embodiments $R^4$ is H. In some embodiments $R^{a3}$ is H.

In some embodiments:

$L^1$ is selected from the group consisting of a bond and —C(O)(n-butylene)-;

$R^1$ is selected from the group consisting of H and unsubstituted bicyclic 8-10 membered heterocycloalkyl;

$L^2$ is selected from the group consisting of —($C_{1-6}$ alkylene)-(5-6 membered heteroarylene)-, —C(O)—, and —C(O)($C_{1-6}$ alkylene)-;

$R^2$ is selected from the group consisting of $C_{1-6}$ alkoxy, phenyl, bicyclic 8-10 membered heterocycloalkyl, and bicyclic 8-10 membered heteroaryl, wherein each $C_{1-6}$ alkoxy, phenyl, bicyclic 8-10 membered heterocycloalkyl, and bicyclic 8-10 membered heteroaryl is optionally substituted by one substituent independently selected from OH, halo, and $C_{1-6}$ haloalkyl;

$L^3$ is selected from the group consisting of a bond, —C(O)NH($C_{1-6}$alkylene)-, —C(O)N($R^{a3}$)($C_{1-6}$ alkylene)-di($C_{1-6}$ alkyl)amino, and —C(O)NH($C_{1-6}$ alkyleneoxy)-; and $R^3$ is selected from the group consisting of H, $C_{1-6}$ haloalkyl, bicyclic 8-10 membered heteroaryl, and —C(O)N($R^{a3}$)($C_{1-6}$ haloalkoxy), wherein each $C_{1-6}$ haloalkyl and bicyclic 8-10 membered heteroaryl is optionally substituted by one substituent independently selected from OH, halo, and $C_{1-6}$ haloalkyl;

or alternatively, -$L^3$-$R^3$ forms an oxo group.

In some embodiments:

$L^1$ is selected from the group consisting of a bond and —C(O)(n-butylene)-;

$R^1$ is selected from the group consisting of H and

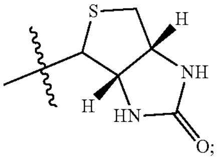 [SMILES: *C1SC[C@@H]2NC(=O)N[C@H]12];

$L^2$ is selected from the group consisting of —($C_{1-6}$ alkylene)-(triazolyl)-, —C(O)—, and —C(O)($C_{1-6}$ alkylene)-;

$R^2$ is selected from the group consisting of $C_{1-6}$ alkoxy, phenyl, bicyclic 8-10 membered heterocycloalkyl, and bicyclic 8-10 membered heteroaryl, wherein each $C_{1-6}$ alkoxy, phenyl, bicyclic 8-10 membered heterocycloalkyl, and bicyclic 8-10 membered heteroaryl is optionally substituted by one substituent independently selected from OH, halo, and $C_{1-6}$ haloalkyl;

$L^3$ is selected from the group consisting of a bond, —C(O)NH($C_{1-6}$alkylene)-, —C(O)NH($C_{1-6}$ alkylene)-N$(CH_3)_2$, and —C(O)NH($C_{1-6}$ alkyleneoxy)-; and $R^3$ is selected from the group consisting of H, $C_{1-6}$ haloalkyl, bicyclic 8-10 membered heteroaryl, and —C(O)N($R^{a3}$)($C_{1-6}$ haloalkoxy), wherein each $C_{1-6}$ haloalkyl and bicyclic 8-10 membered heteroaryl is optionally substituted by one substituent independently selected from OH, halo, and $C_{1-6}$ haloalkyl.

In some embodiments:

$L^1$ is selected from the group consisting of a bond and —C(O)(n-butylene)-;

$R^1$ is selected from the group consisting of H and

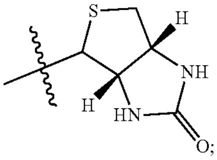 [SMILES: *C1SC[C@@H]2NC(=O)N[C@H]12];

$L^2$ is selected from the group consisting of —$CH_2$-(triazolyl)-, —C(O)—, and —C(O)($C_{1-6}$ alkylene)-;

$R^2$ is selected from the group consisting of $C_{1-6}$ alkoxy, phenyl,

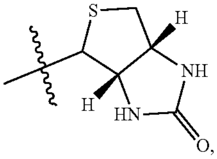 [SMILES: *C1SC[C@@H]2NC(=O)N[C@H]12], and indole, wherein each $C_{1-6}$ alkoxy, phenyl, and indole is optionally substituted by one substituent independently selected from OH, halo, and $C_{1-6}$ haloalkyl;

$L^3$ is selected from the group consisting of a bond, —C(O)NH($C_{1-6}$alkylene)-, —C(O)NH($C_{1-6}$ alkylene)-N$(CH_3)_2$ and —C(O)NH($C_{1-6}$ alkyleneoxy)-; and $R^3$ is selected from the group consisting of H, $C_{1-6}$ haloalkyl, —C(O)NH$CH_2CH_2OCH_2CH_2OCH_2CH_2F$, and indole, wherein each $C_{1-6}$ haloalkyl and indole is optionally substituted by one substituent independently selected from OH, halo, and $C_{1-6}$ haloalkyl.

In some embodiments:

$L^1$ is selected from the group consisting of a bond —C(O)—, —C(O)($C_{1-6}$ alkylene)-, and —C(O)($C_{1-6}$ alkyleneoxy)-;

$R^1$ is selected from the group consisting of H, $C_{3-10}$ cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, and —C(O)($C_{1-6}$alkylene)-;

$R^2$ is selected from the group consisting of $C_{1-6}$ alkoxy, $C_{6-10}$ aryl, 4-10 membered heterocycloalkyl and 5-10 membered heteroaryl, wherein each $C_{1-6}$ alkoxy $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N$R^{a3}$—, —C(O)N($R^{a3}$)($C_{1-6}$ alkylene)-, and —C(O)N($R^{a3}$)($C_{1-6}$alkyleneoxy)-; and $R^3$ is selected from the group consisting of H, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

or alternatively, -$L^3$-$R^3$ forms an oxo group.

In some embodiments:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by 1, 2, 3, or 4 substituents independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$)($C_{1-6}$ alkylene)-, and —C(O)N($R^{a3}$)($C_{1-6}$ alkyleneoxy)-; and $R^3$ is selected from the group consisting of H, $C_{1-6}$ haloalkyl, and 5-10 membered heteroaryl, wherein each $C_{1-6}$ haloalkyl, and 5-10 membered heteroaryl is optionally substituted by 1, 2, 3, or 4 substituents independently selected from OH, halo, and $C_{1-6}$ haloalkyl;

or alternatively, $-L^3-R^3$ forms an oxo group.

In some embodiments:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by one substituent independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by one substituent independently selected from OH, halo, and $C_{1-6}$ haloalkyl;

$L^3$ is selected from the group consisting of a bond, —C(O)N($R^{a3}$)($C_{1-6}$ alkylene)-, and —C(O)N($R^{a3}$)($C_{1-6}$ alkyleneoxy)-; and $R^3$ is selected from the group consisting of H, $C_{1-6}$ haloalkyl, and 5-10 membered heteroaryl, wherein each $C_{1-6}$ haloalkyl, and 5-10 membered heteroaryl is optionally substituted by one substituent independently selected from OH, halo, and $C_{1-6}$ haloalkyl;

or alternatively, $-L^3-R^3$ forms an oxo group.

In some embodiments $R^4$ is H. In some embodiments $R^{a3}$ is H.

In some embodiments:

$L^1$ is selected from the group consisting of a bond and —C(O)(n-butylene)-;

$R^1$ is selected from the group consisting of H and unsubstituted bicyclic 8-10 membered heterocycloalkyl;

$L^2$ is selected from the group consisting of —($C_{1-6}$ alkylene)-(5-6 membered heteroarylene)-, —C(O)—, and —C(O)($C_{1-6}$ alkylene)-;

$R^2$ is selected from the group consisting of $C_{1-6}$ alkoxy, phenyl, bicyclic 8-10 membered heterocycloalkyl, and bicyclic 8-10 membered heteroaryl, wherein each $C_{1-6}$ alkoxy, phenyl, bicyclic 8-10 membered heterocycloalkyl, and bicyclic 8-10 membered heteroaryl is optionally substituted by one substituent independently selected from OH, halo, and $C_{1-6}$ haloalkyl;

$L^3$ is selected from the group consisting of a bond, —C(O)NH($C_{1-6}$ alkylene)-, and —C(O)NH($C_{1-6}$ alkyleneoxy)-; and $R^3$ is selected from the group consisting of H, $C_{1-6}$ haloalkyl, and bicyclic 8-10 membered heteroaryl, wherein each $C_{1-6}$ haloalkyl and bicyclic 8-10 membered heteroaryl is optionally substituted by one substituent independently selected from OH, halo, and $C_{1-6}$ haloalkyl;

or alternatively, $-L^3-R^3$ forms an oxo group.

In some embodiments:

$L^1$ is selected from the group consisting of a bond and —C(O)(n-butylene)-;

$R^1$ is selected from the group consisting of H and

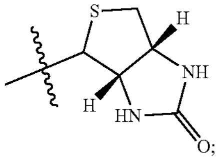 [SMILES: *C1SC[C@@H]2NC(=O)N[C@H]12]

;

$L^2$ is selected from the group consisting of -($C_{1-6}$ alkylene)-(triazolyl)-, —C(O)—, and —C(O)($C_{1-6}$ alkylene)-;

$R^2$ is selected from the group consisting of $C_{1-6}$ alkoxy, phenyl, bicyclic 8-10 membered heterocycloalkyl, and bicyclic 8-10 membered heteroaryl, wherein each $C_{1-6}$ alkoxy, phenyl, bicyclic 8-10 membered heterocycloalkyl, and bicyclic 8-10 membered heteroaryl is optionally substituted by one substituent independently selected from OH, halo, and $C_{1-6}$ haloalkyl;

$L^3$ is selected from the group consisting of a bond, —C(O)NH($C_{1-6}$ alkylene)-, and —C(O)NH($C_{1-6}$ alkyleneoxy)-; and $R^3$ is selected from the group consisting of H, $C_{1-6}$ haloalkyl, and bicyclic 8-10 membered heteroaryl, wherein each $C_{1-6}$ haloalkyl and bicyclic 8-10 membered heteroaryl is optionally substituted by one substituent independently selected from OH, halo, and $C_{1-6}$ haloalkyl, In some embodiments:

$L^1$ is selected from the group consisting of a bond and —C(O)(n-butylene)-;

$R^1$ is selected from the group consisting of H and

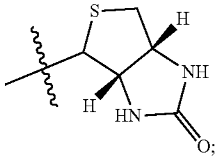 [SMILES: *C1SC[C@@H]2NC(=O)N[C@H]12]

;

$L^2$ is selected from the group consisting of —$CH_2$-(triazolyl)-, —C(O)—, and —C(O)($C_{1-6}$ alkylene)-;

$R^2$ is selected from the group consisting of $C_{1-6}$ alkoxy, phenyl,

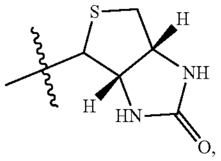 [SMILES: *C1SC[C@@H]2NC(=O)N[C@H]12]

, and indole, wherein each $C_{1-6}$ alkoxy, phenyl, and indole is optionally substituted by one substituent independently selected from OH, halo, and $C_{1-6}$ haloalkyl;

$L^3$ is selected from the group consisting of a bond, —C(O)NH($C_{1-6}$ alkylene)-, and —C(O)NH($C_{1-6}$ alkyleneoxy)-; and $R^3$ is selected from the group consisting of H, $C_{1-6}$ haloalkyl, and indole, wherein each $C_{1-6}$ haloalkyl and indole is optionally substituted by one substituent independently selected from OH, halo, and $C_{1-6}$ haloalkyl.

In some embodiments:

$L^1$ is a bond;

$R^1$ is H;

$L^3$ is a bond; and $R^3$ is H.

In some embodiments:

$L^1$ is a bond;

$R^1$ is H;

$L^2$ is selected from the group consisting of —C(O)— and —C(O)($C_{1-6}$ alkylene)-.

$R^2$ is $C_{6-10}$ aryl which is optionally substituted by 1, 2, 3, or 4 substituents independently selected from OH, halo, and $C_{1-6}$ haloalkyl;

$L^3$ is a bond; and $R^3$ is H.

In some embodiments:

$L^1$ is a bond;

$R^1$ is H;

$L^2$ is —C(O)—.

$R^2$ is $C_{6-10}$ aryl which is optionally substituted by 1, 2, 3, or 4 substituents independently selected from OH, halo, and $C_{1-6}$ haloalkyl;

$L^3$ is a bond; and $R^3$ is H.

In some embodiments:

$L^1$ is a bond;

$R^1$ is H; and $L^3$-$R^3$ forms an oxo group.

In some embodiments:

$L^1$ is a bond;

$R^1$ is H;

$L^2$ is selected from the group consisting of —C(O)—, —C(O)O—, and —C(O)$NR^{a2}$—;

$R^2$ is $C_{6-10}$ aryl which is optionally substituted by 1, 2, 3, or 4 substituents independently selected from OH, halo, and $C_{1-6}$ haloalkyl;

-$L^3$-$R^3$ forms an oxo group; and $R^{a2}$ is H.

In some embodiments:

$L^1$ is a bond;

$R^1$ is H;

$L^2$ is —C(O)$NR^{a2}$—;

$R^2$ is $C_{6-10}$ aryl which is optionally substituted by 1, 2, 3, or 4 substituents independently selected from OH, halo, and $C_{1-6}$ haloalkyl;

-$L^3$-$R^3$ forms an oxo group; and $R^{a2}$ is H.

In some embodiments, the compound of Formula VI or Formula I is a compound of Formula II:

(II)

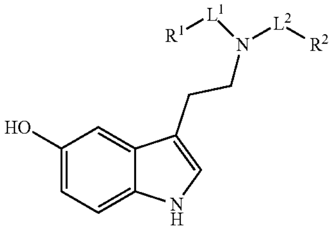

or a pharmaceutically acceptable salt thereof, wherein $R^1$, $L^1$, $L^2$, and $R^2$ are as defined above.

In some embodiments, the compound of Formula VI or Formula I is a compound of Formula III:

(III)

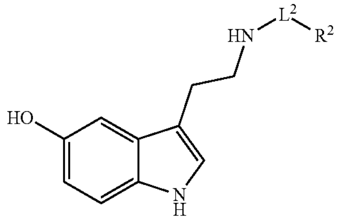

or a pharmaceutically acceptable salt thereof, wherein $L^2$ and $R^2$ are as defined above.

In some embodiments, the compound of Formula VI or Formula I is a compound of Formula IV:

(IV)

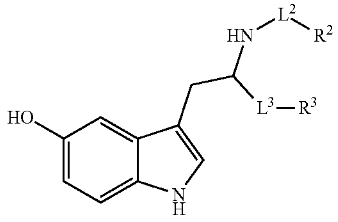

or a pharmaceutically acceptable salt thereof wherein $L^2$, $R^2$, $L^3$, and $R^3$ are as defined above.

In some embodiments, the compound of Formula VI or Formula I is a compound of Formula V:

(V)

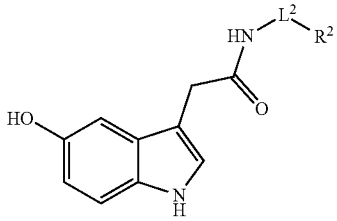

or a pharmaceutically acceptable salt thereof, wherein $L^2$ and $R^2$ are as defined above.

In some embodiments, the compound of Formula VI or Formula I is a compound selected from the group consisting of:

-continued
(3)
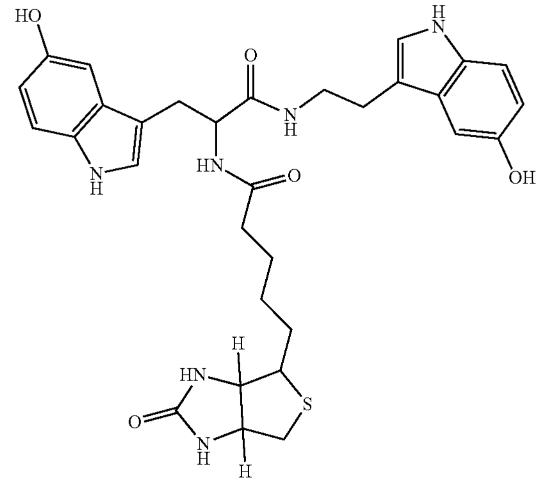
(4)
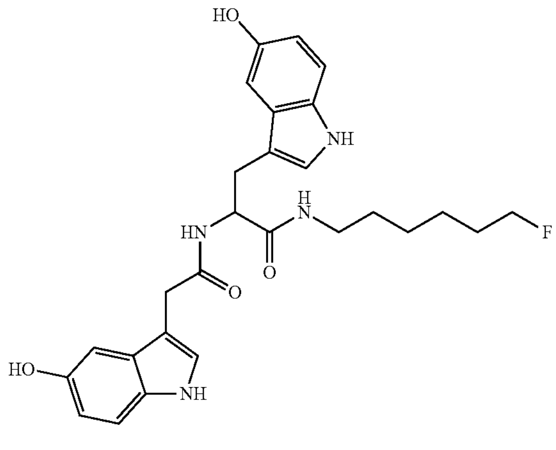
(5)
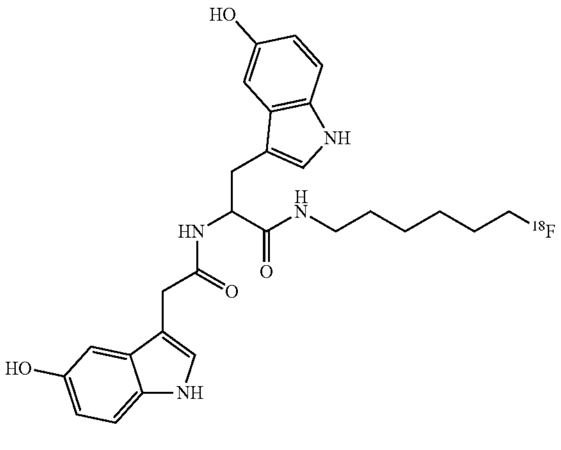
(6)
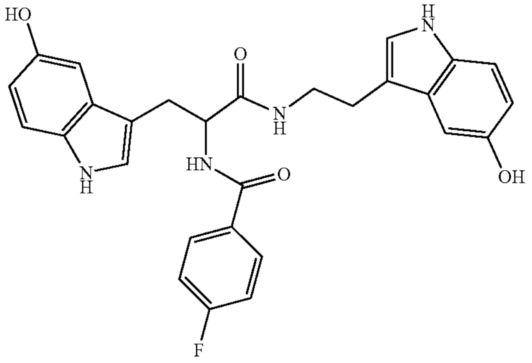
(7)
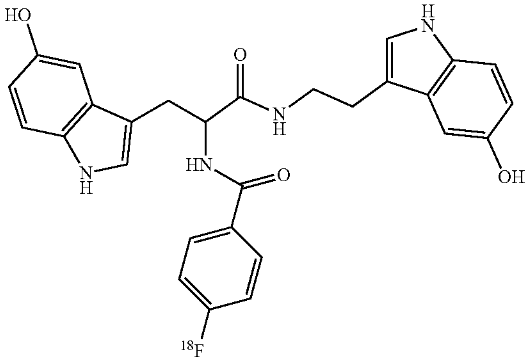
(8)
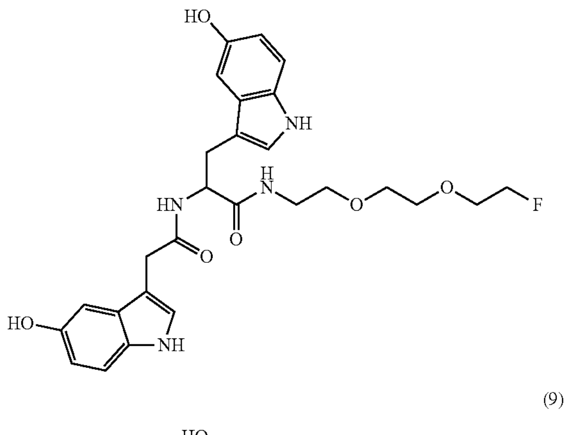
(9)
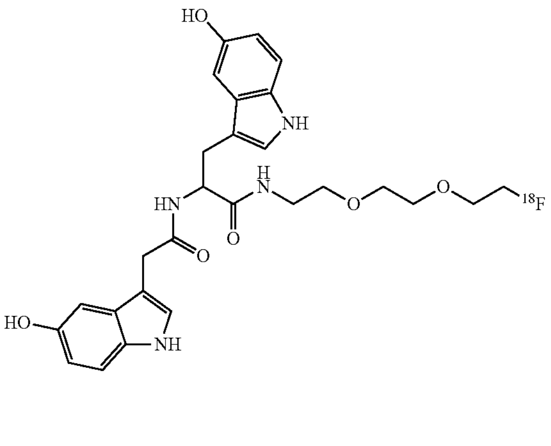

-continued
(12)
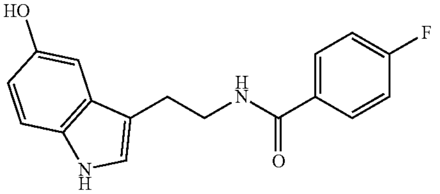
(13)
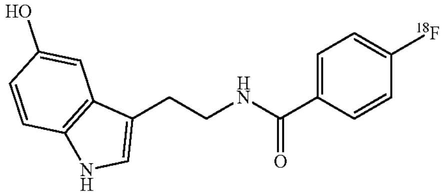
(14)
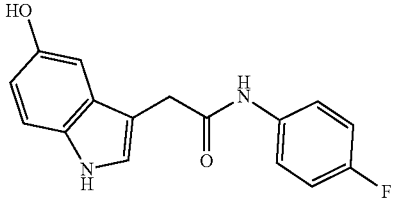
(15)
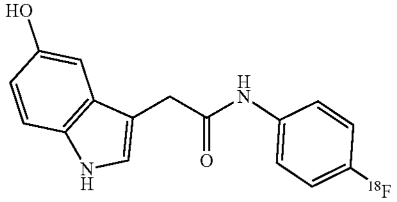
(16)
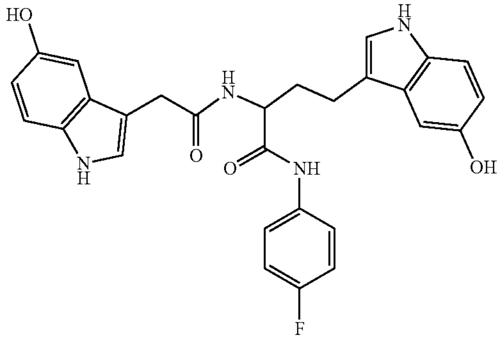
(17)
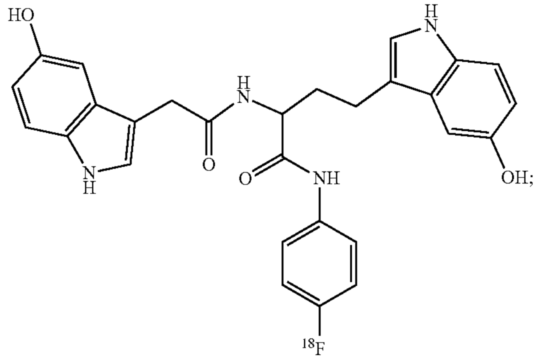
;
-continued
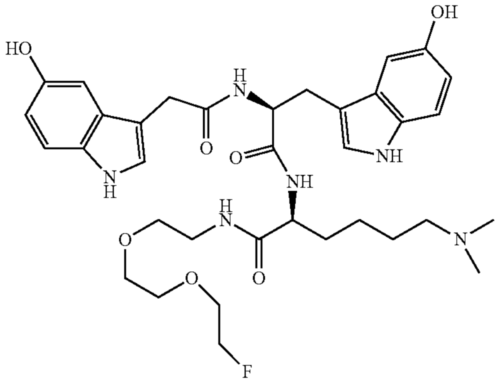
; and
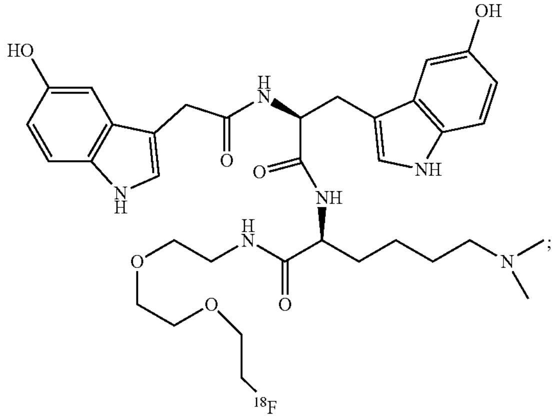
;
or a pharmaceutically acceptable salt thereof.
In some embodiments, the compound of Formula VI or Formula I is a compound selected from the group consisting of:
(3)
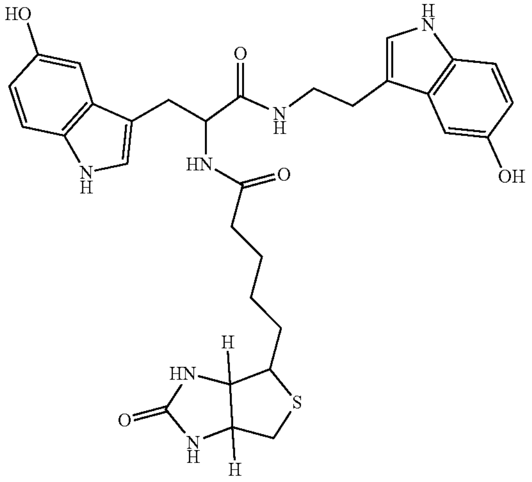

-continued
(4)
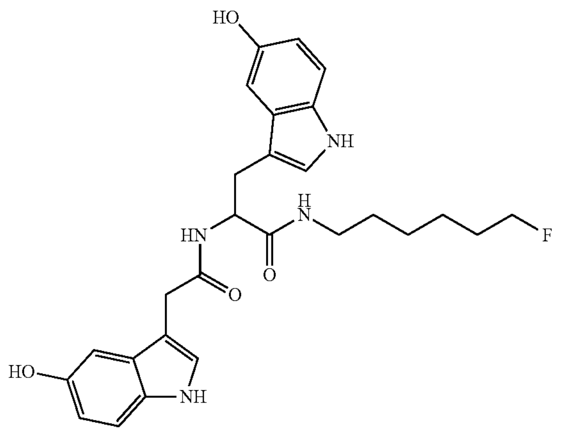
(5)
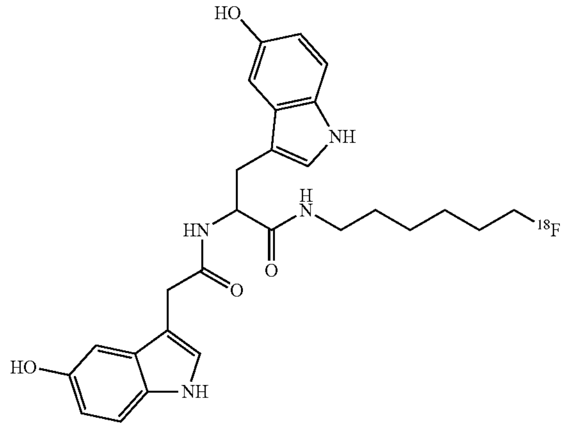
(6)
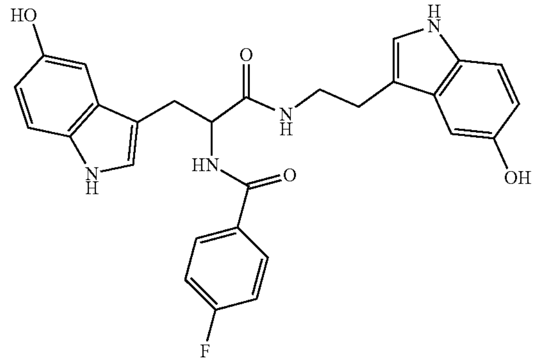
-continued
(7)
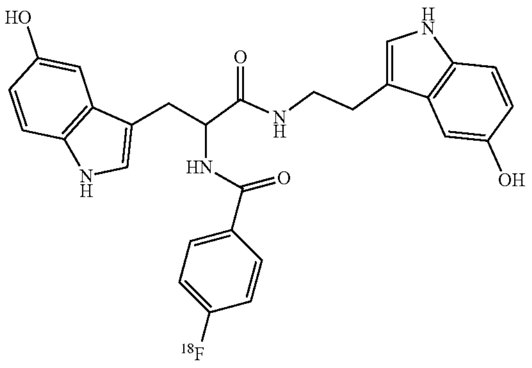
(8)
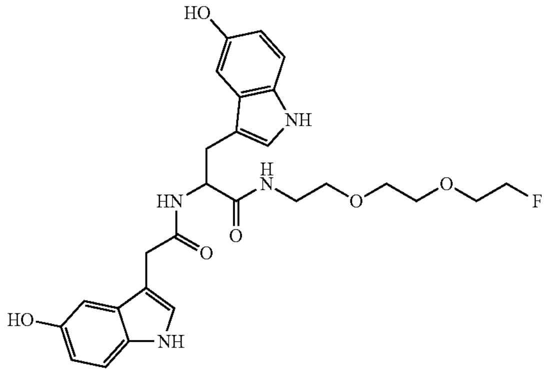
(9)
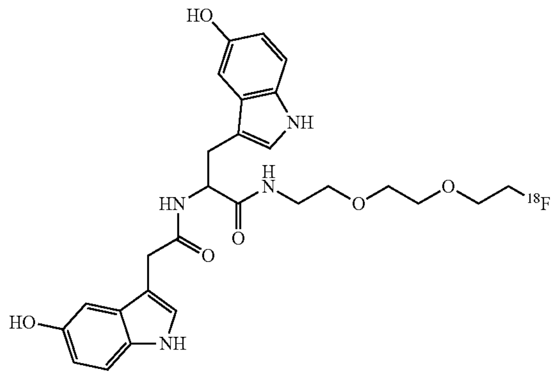
(12)
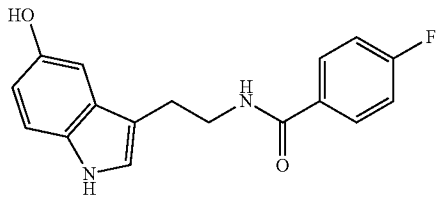
(13)
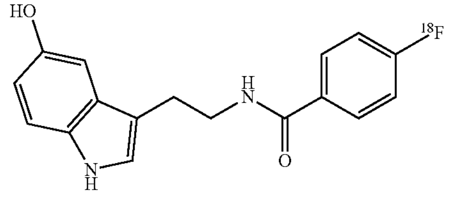

-continued
(14)
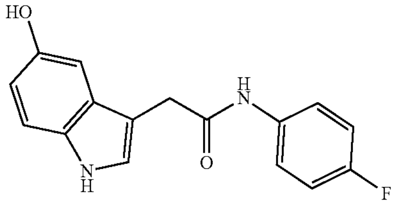
(15)
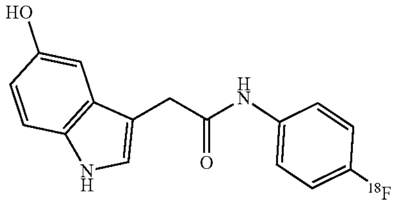
(16)
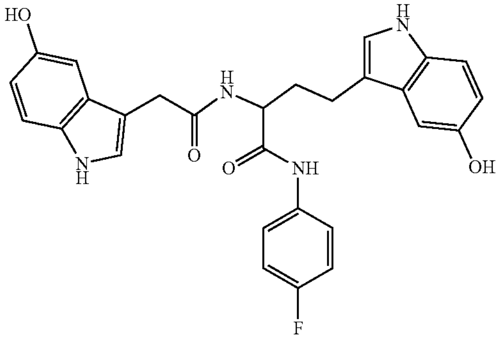
and
(17)
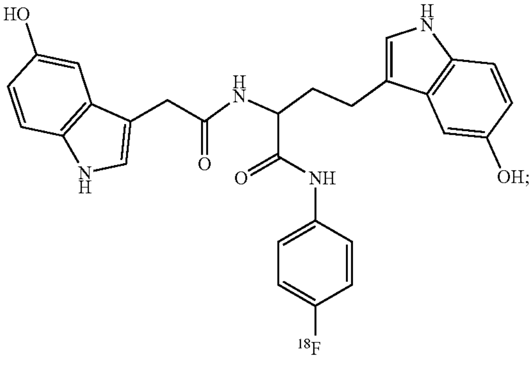
;
or a pharmaceutically acceptable salt thereof.
In some embodiments, the compound of Formula VI or Formula I is:
(3)
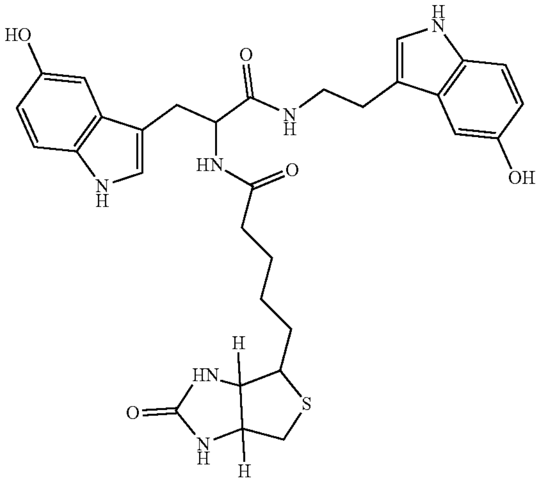
or a pharmaceutically acceptable salt thereof.
In some embodiments, the compound of Formula VI or Formula I is a compound selected from the group consisting of:
(5)
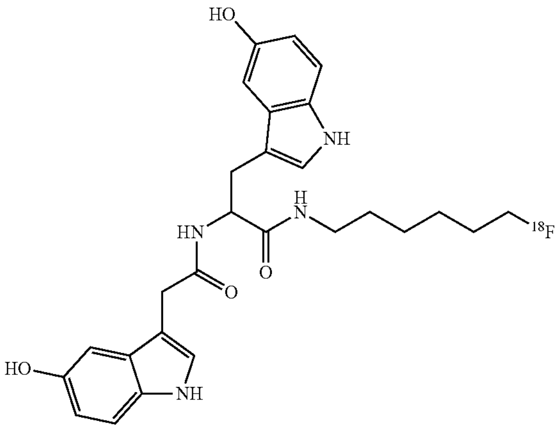
(7)
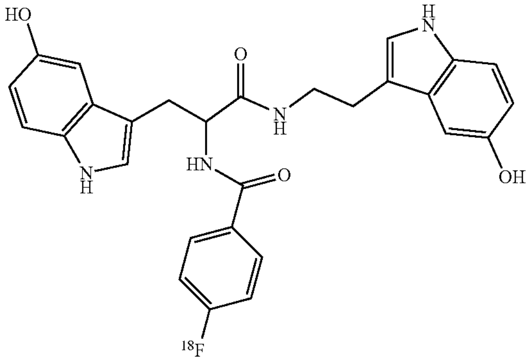

-continued (9)

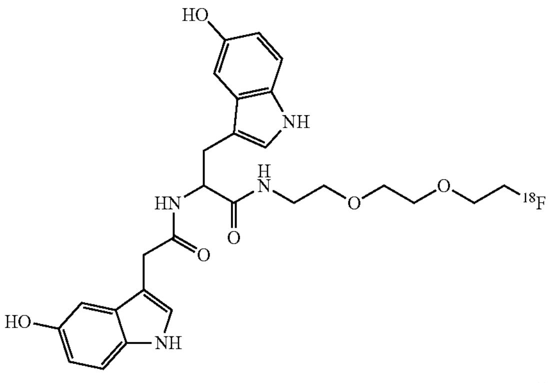

(13)

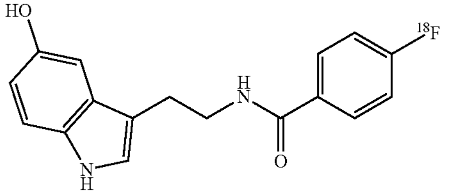

(15)

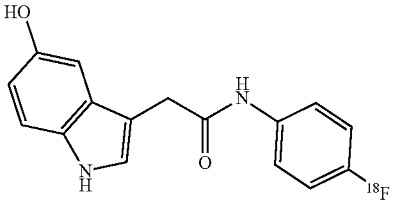

and (17)

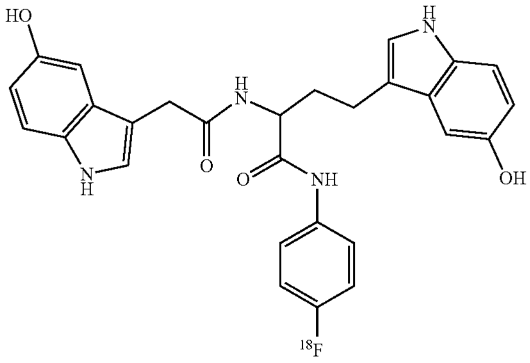

or a pharmaceutically acceptable salt thereof.

Synthesis

As will be appreciated, the compounds provided herein, including salts thereof, can be prepared using known organic synthesis techniques and can be synthesized according to any of numerous possible synthetic routes.

The synthesis of the intermediates 1 and 2f are shown in Scheme 1. Briefly, 5-hydroxy-indole acetic acid (5-HIAA) was coupled with 5-hydroxy-L-tryptophan using N,N'-dicyclohexylcarbodiimide (DCC) and N-hydroxysuccinimide (NHS) as coupling agents to give intermediate 1 in the yield of 62%. The addition order (5-HIAA first reacted with DCC and NHS) of the substrate minimized the formation of homo-coupling byproduct from 5-hydroxy-L-tryptophan.

The reaction of triethylene glycol with tosyl chloride gave intermediate 2a, followed by reacting with sodium azide providing mono-substituted intermediate 2b, which was treated with triphenyl-phosphene then water to give intermediate 2c. Intermediate 2c was subsequently Boc-protected, followed by fluorination with TBAF at 60° C. to give intermediate 2e. Boc-deprotection of intermediate 2e with TFA provided intermediate 2f and the overall yield of the three steps was 50%.

Scheme 1.

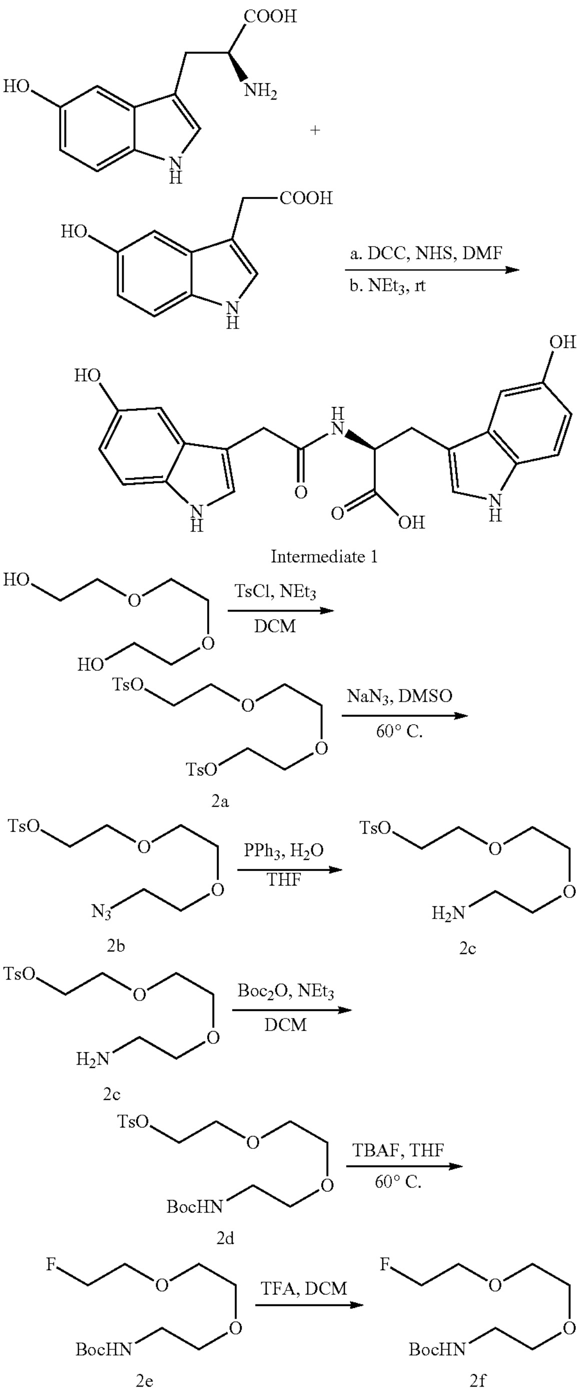

The compounds of Formula VI (e.g., compounds of Formula I) provided herein can be also prepared using methods analogous to those shown in Scheme 2, by substituting the appropriate starting materials.
Scheme 2.
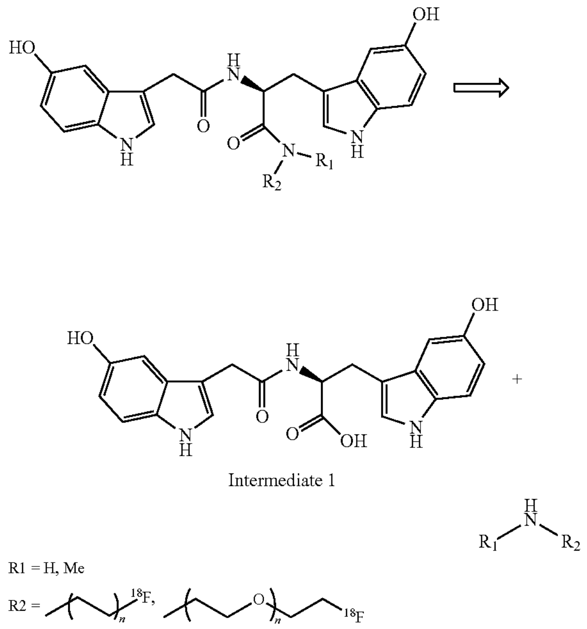
Intermediate 1
Compound 5
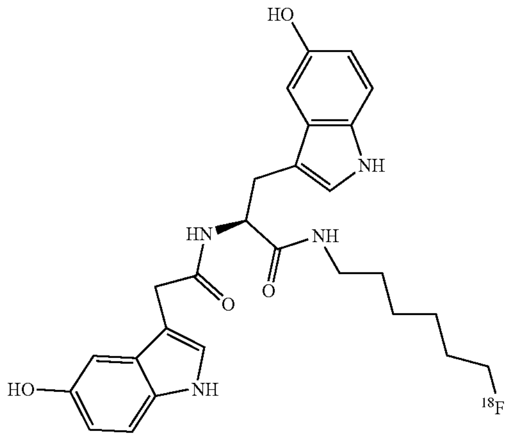
Compound 7
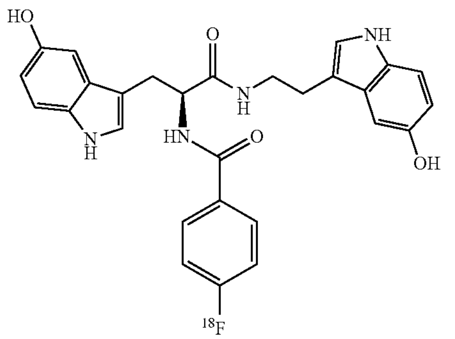
-continued
Compound 19
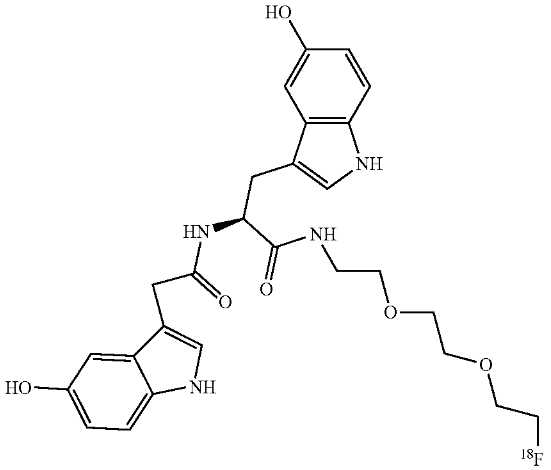
The compounds of Formula VI (e.g., compounds of Formula I) provided herein can be also prepared using methods analogous to those shown in Scheme 3.
Scheme 3.
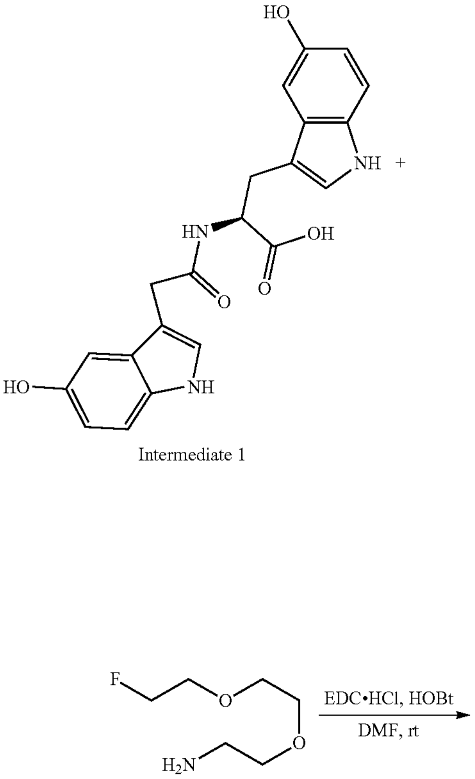
Intermediate 1
Intermediate 2f -continued
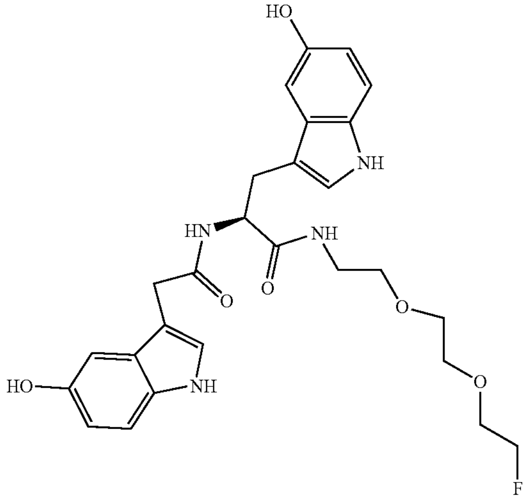
Compound 8
The compounds of Formula VI (e.g., compounds of Formula I) provided herein can be also prepared using methods analogous to those shown in Scheme 4.
Scheme 4.
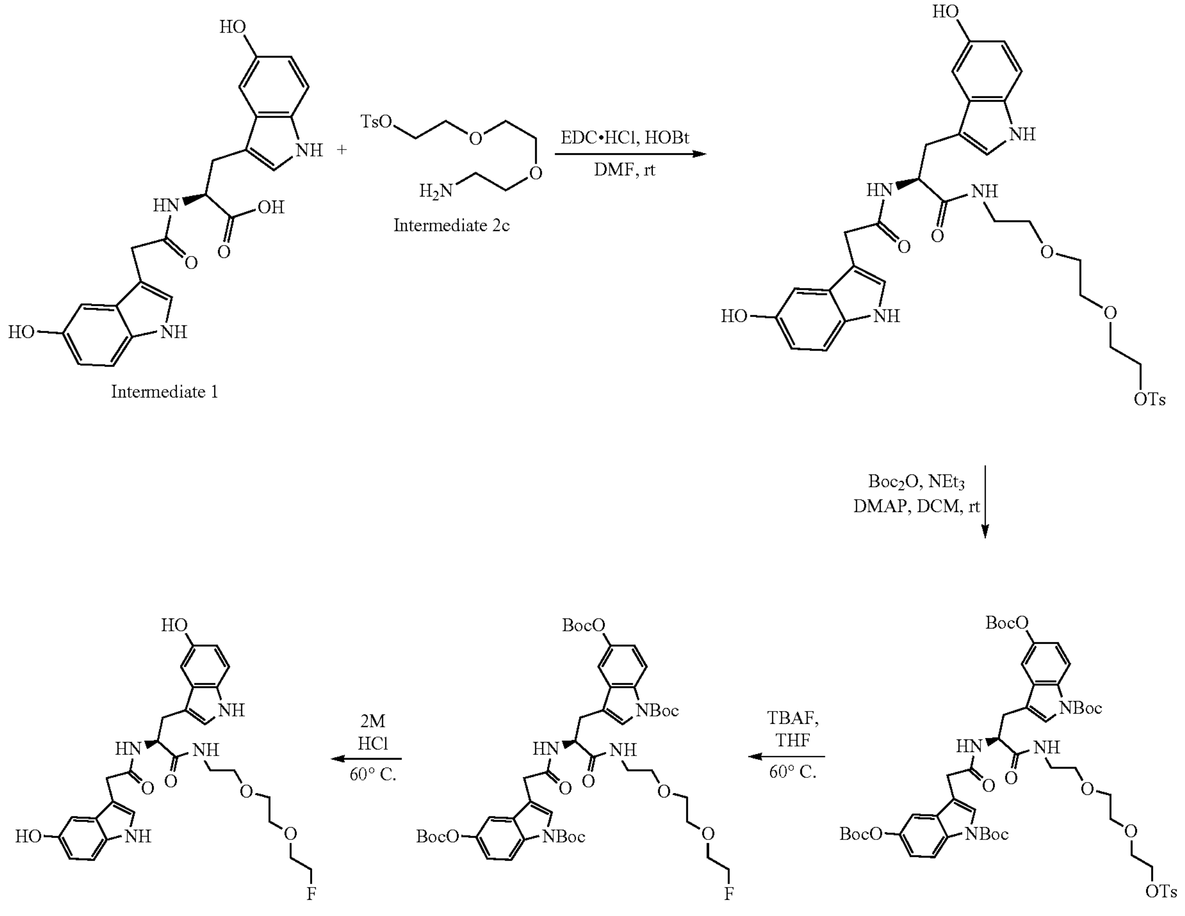
Intermediate 1
Intermediate 2c
Compound 8

The compounds of Formula VI (e.g. compounds of Formula I) provided herein can be also prepared using methods analogous to those shown in Scheme 5.
Scheme 5.
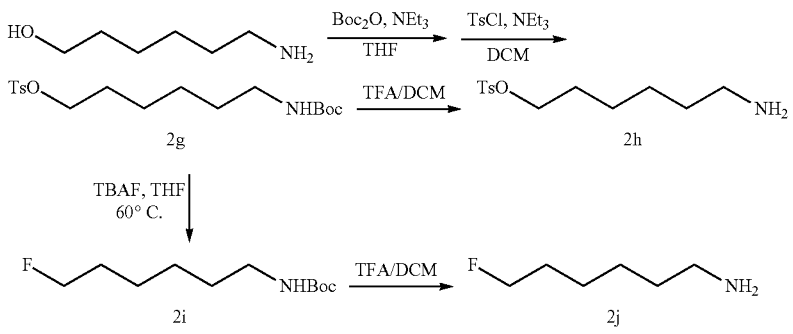
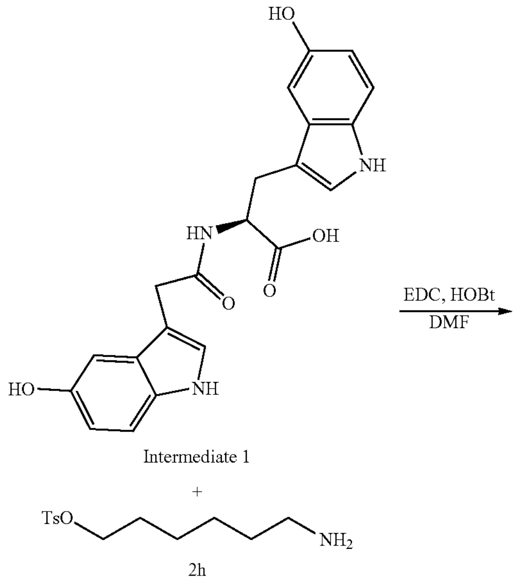
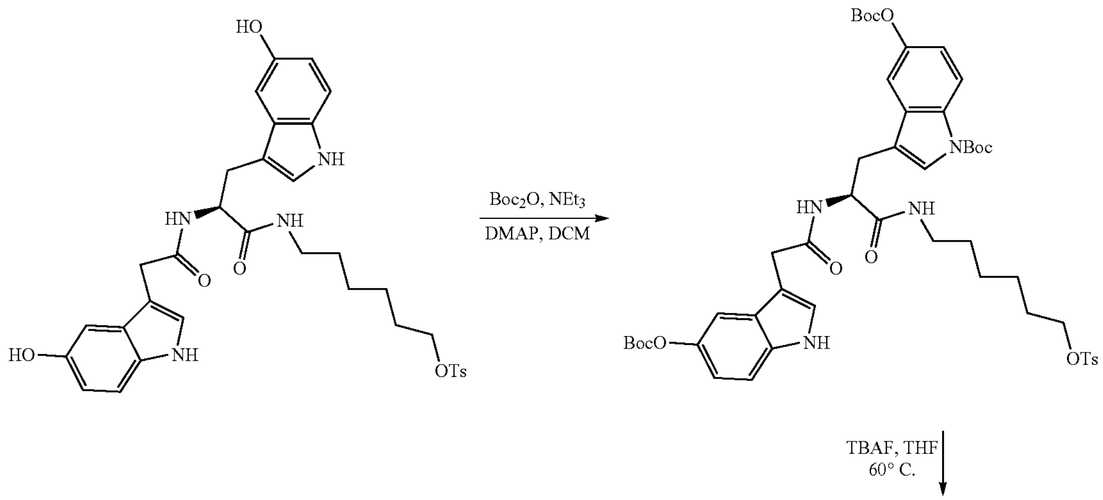

-continued
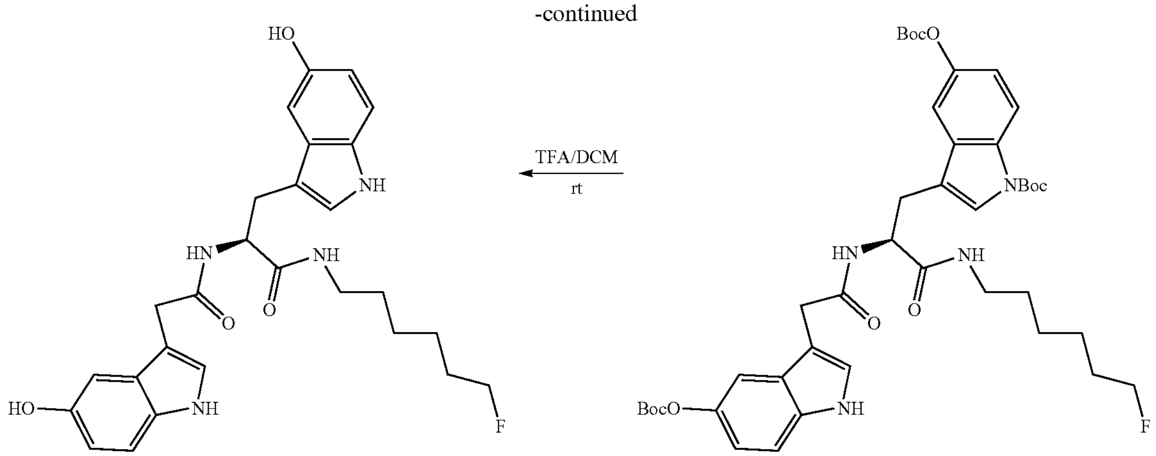
Compound 4
The compounds of Formula VI (e.g., compounds of Formula I) provided herein can be also prepared using methods analogous to those shown in Scheme 6.
Scheme 6.
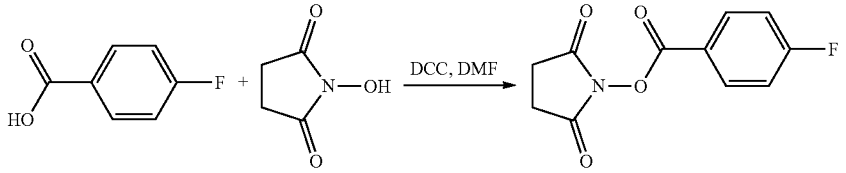
2k
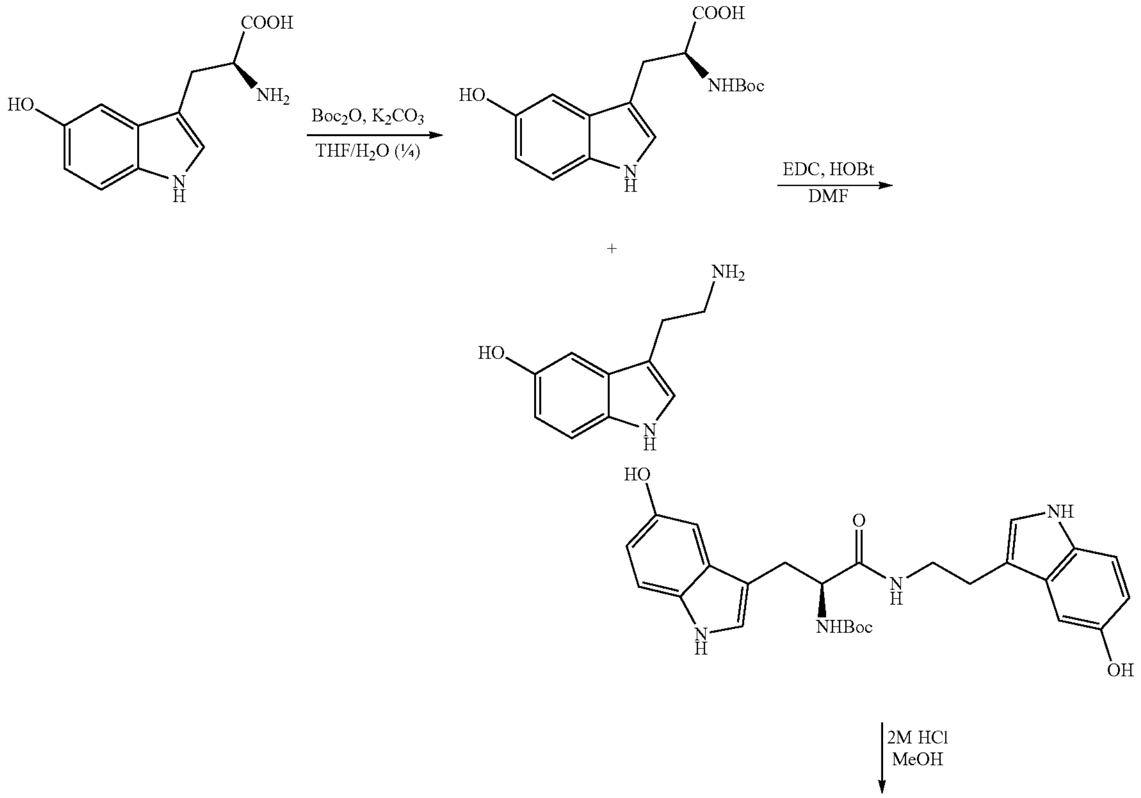

-continued
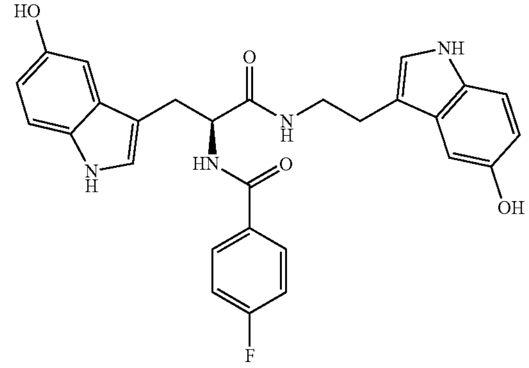
Compound 6
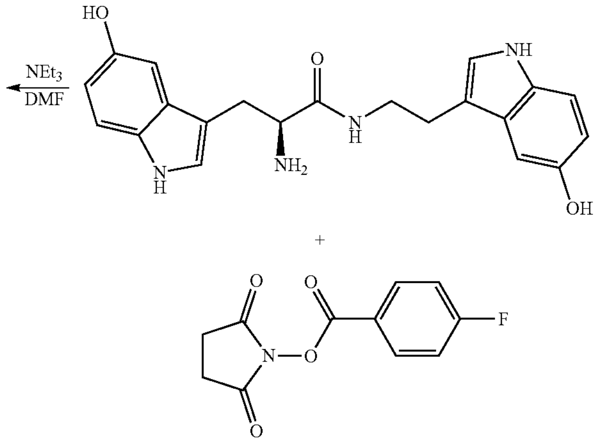
2k
The compounds of Formula VI (e.g., compounds of Formula I) provided herein can be also prepared using methods analogous to those shown in Scheme 7.
Scheme 7.
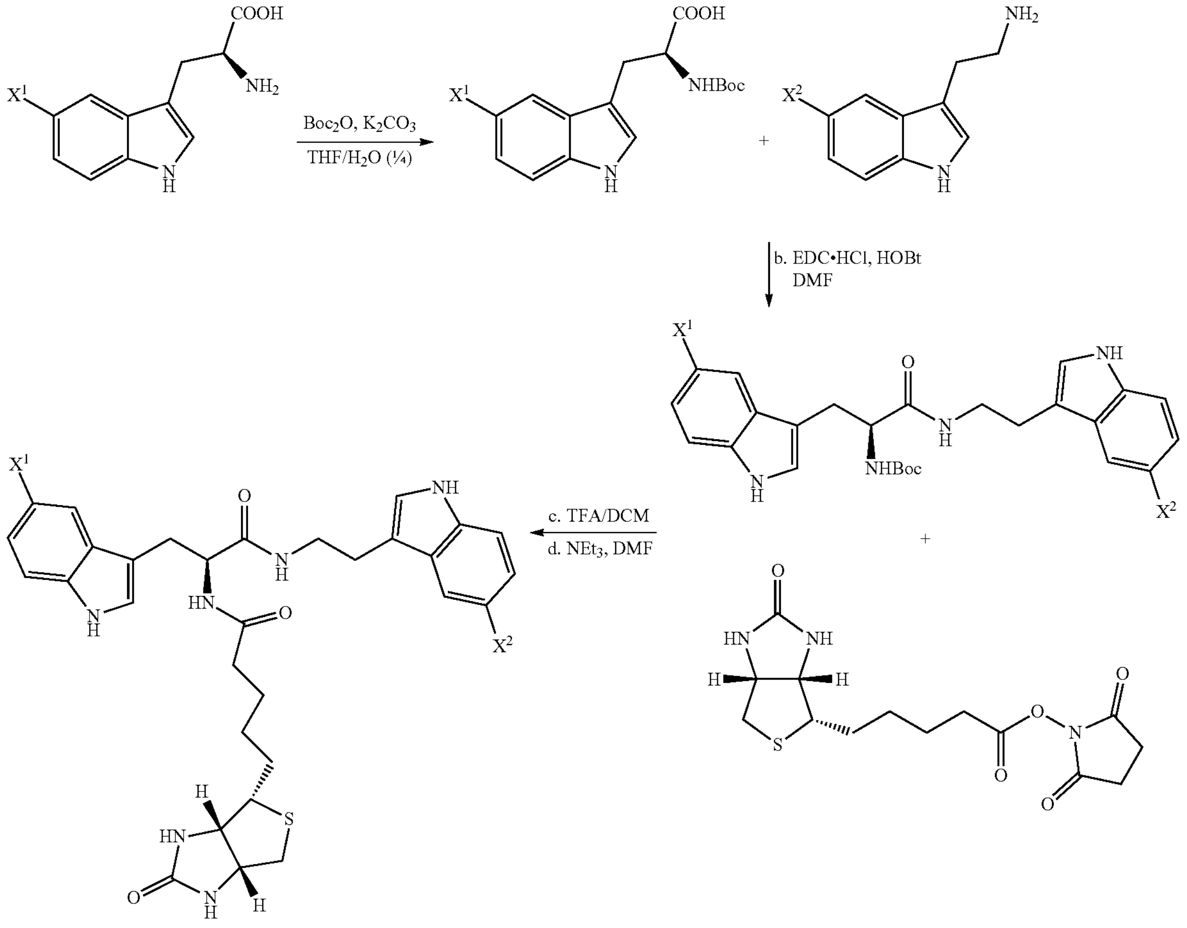
$X^1$ = H or OH
$X^2$ = H or OH The radiolabeled compounds of Formula VI (e.g., compounds of Formula I) provided herein can be prepared, for example, using methods analogous to those shown below in the procedure provided in Scheme 8.

Scheme 8.

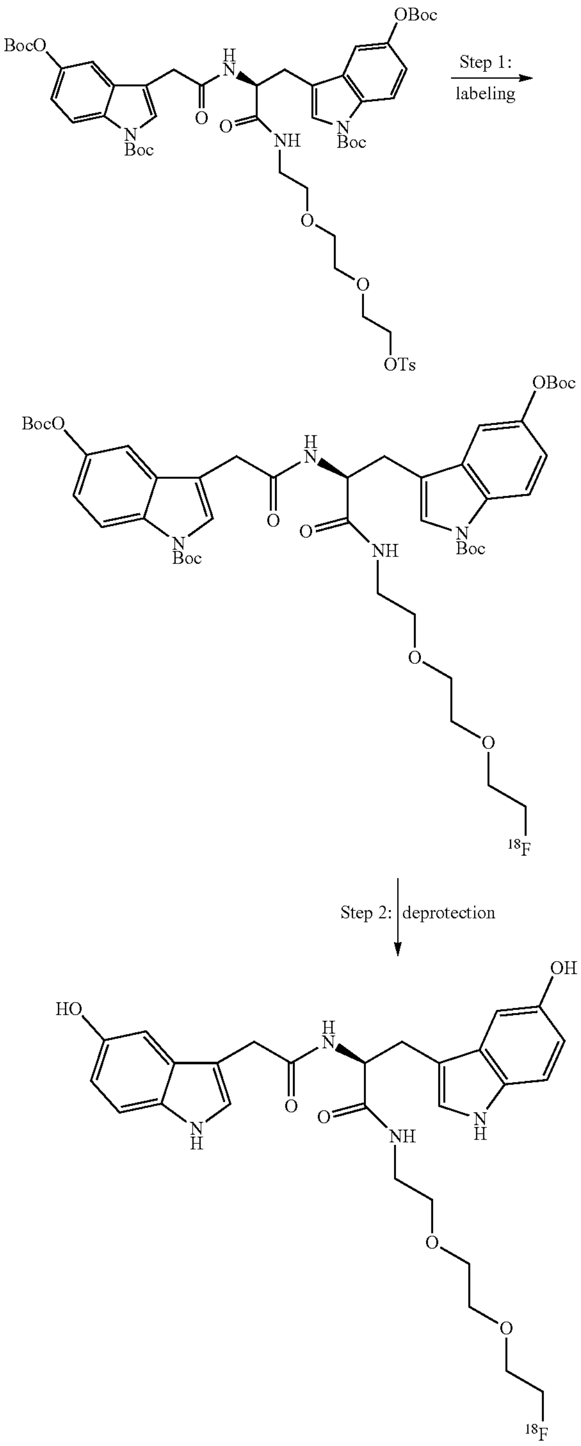

Compound 9

Synthetic methods for incorporating radioisotopes into organic compounds are well known in the art, and one of ordinary skill in the art will readily recognize other methods applicable for the compounds provided herein.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4, 2011/1-4; 2012/1-2 (Thieme, 2001-2012); Katritzky, et al. (Ed) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, $—NR(CR'R'')_n—$ includes both $—NR(CR'R'')_n—$ and $—(CR'R'')_nNR—$. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formulae "—O-alkyl" or "—(O-alkylene)$_p$-", or "-(alkylene-O)$_p$—, wherein the alkyl or alkylene group has n to m carbons and p is an integer from 1 to 6. Example alkoxy groups include methoxy, ethoxy, propoxy (e.g., n-propoxy and isopropoxy), tert-butoxy, $—(CH_2OCH_2OCH_2)—$, $—(CH_2CH_2OCH_2CH_2O)—$, $—(OCH_2)—$, $—(OCH_2OCH_2CH_2)—$, $—(CH_2CH_2OCH_2CH_2O)—$, $—(CH_2CH_2OCH_2CH_2OCH_2CH_2)—$ and the like. In some embodiments, the alkyl group has 1 to 6, 1 to 4, or 1 to 3 carbon atoms. In some embodiments, p is 1. In some embodiments, p is 2. In some embodiments, p is 3. In some embodiments, p is 4. In some embodiments, p is 5. In some embodiments, p is 6.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g, phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "di($C_{n-m}$-alkyl)amino" refers to a group of formula $—N(alkyl)_2$, wherein the two alkyl groups each has, independently, n to m carbon atoms. In some embodiments, each alkyl group independently has 1 to 6, 1 to 4, or 1 to 3 carbon atoms. In some embodiments, a di($C_{n-m}$-alkyl)amino as $—N(CH_3)_2$ (i.e., dimethylamino).

As used herein, "halo" refers to F, Cl, Br, or I. In some embodiments, a halo is F, Cl, or Br. In some embodiments, a halo is F. In some embodiments, a halo is [$^{18}$F].

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, the term "$C_{n-m}$ haloalkoxy", employed alone or in combination with other terms, refers to a group of formulae "—O-alkyl" or "—(O-alkylene)$_p$-", or "-(alkylene-O)$_p$—, wherein the alkyl or alkylene group, has n to m carbons, p is an integer from 1 to 6, and each alkyl and alkylene group has from one halogen atom to 2s+1 halogen atoms which may be the same or different. Example haloalkoxy groups include $OCF_3$, $OCH_2CF_3$, $OCH_2CHF_2$, $OCH_2CH_2F$, OCF2CF3, $OCF_2CF_2CF_2$, $OCH_2CH_2CF_3$, $—CH_2OCH_2OCH_2F$, $—CH_2OCH_2OCHF_2$, $—CH_2OCH_2OCF_3$, $—(CF_2CF_2OCH_2CH_2O)—$, $—(OCF_2)—$, $—(OCF_2OCH_2CH_2)—$, $—(CH_2CH_2OCH_2CH_2OCH_2CH_2)—$, $——CH_2CH_2OCH_2CH_2OCH_2CH_2F$, and the like. In some embodiments, the haloalkoxy group has 1 to 6, 1 to 4, or 1 to 3 carbon atoms. In some embodiments, p is 1. In some embodiments, p is 2. In some embodiments, p is 3. In some embodiments, p is 4. In some embodiments, p is 5. In some embodiments, p is 6. In some embodiments, the haloalkoxy group is a fluoroalkoxy group. In some embodiment, the haloalkoxy group is a [$^{18}$F]-fluoroalkoxy group.

As used herein, "cycloalkyl" refers, to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member, selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, tetrazolyl, 1,2,3-thiadiazolyl, 1,2,3-oxadiazolyl, 1,2,4-triazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}C$], [$^{18}F$]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e. at least 45% incorporation of deuterium). Exemplary isotopes that may be incorporated into the compounds provided herein include, but are not limited to, $^{2}H$, $^{3}H$, $^{11}C$, $^{13}C$, $^{14}C$, $^{13}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein: alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use*, Wiley-VCH, 2002.

Methods of Use

The present application further provides a method of imaging a cell or tissue sample. As used herein, the term "subject," refers to any animal, including mammals. For example, mice, rats, other rodents, rabbits, dogs, cats, swine, cattle, sheep, horses, primates, and humans. In some embodiments, the subject is a human.

In some embodiments, the method comprises:

i) administering to the subject a compound provided herein (e.g., a compound of any of Formulas I-VI, or a pharmaceutically acceptable salt thereof);

ii) waiting a time sufficient to allow the compound to accumulate at the cell or tissue sample; and iii) imaging the cell or tissue sample with an imaging technique. In some embodiments, the method further comprises imaging the cell or tissue sample prior to step i). In some embodiments, the method is an in vitro method. In some embodiments, the method is an in vivo method.

The present application further provides a method of diagnosing a disease or disorder associated with abnormal myeloperoxidase (MPO) activity in a subject. In some embodiments, the method comprises:

i) administering to the subject a compound provided herein (e.g., a compound of any of Formulas I-VI, or a pharmaceutically acceptable salt thereof);

ii) waiting a time sufficient to allow the compound to accumulate at a cell or tissue site associated with the disease; and iii) imaging the cell or tissue with an imaging technique. In some embodiments, the method further comprises imaging the subject prior to step i). In some embodiments, the method is an in vitro method. In some embodiments, the method is an in vivo method.

In some embodiments, the time sufficient is from about 5 minutes to about 6 hours, for example, from about 5 minutes to about 6 hours, about 5 minutes to about 4 hours, about 5 minutes to about 2 hours, about 5 minutes to about 1 hour, about 5 minutes to about 30 minutes, about 30 minutes to about 6 hours, about 30 minutes to about 4 hours, about 30 minutes to about 2 hours, about 30 minutes to about 1 hour, about 1 hour to about 6 hours, about 1 hour to about 4 hours, about 1 hour to about 2 hours, about 2 hours to about 6 hours, about 2 hours to about 4 hours, or from about 4 hours to about 6 hours.

The present application further provides a method of imaging myeloperoxidase (MPO) activity in a cell. In some embodiments, the method comprises:

i) contacting the cell with a compound provided herein (e.g., a compound of any of Formulas I-VI, or a pharmaceutically acceptable salt thereof); and ii) imaging the cell with an imaging technique.

The present application further provides a method of imaging myeloperoxidase (MPO) activity in a tissue sample. In some embodiments, the method comprises:

i) contacting the tissue sample with a compound provided herein (e.g., a compound of any of Formulas I-VI, or a pharmaceutically acceptable salt thereof); and ii) imaging the tissue sample with an imaging technique.

The present application further provides a method of detecting myeloperoxidase (MPO) activity in a cell or tissue sample. In some embodiments, the method comprises:

i) contacting the cell or tissue sample with a compound provided herein (e.g., a compound of any of Formulas I-VI, or a pharmaceutically acceptable salt thereof); and ii) imaging the cell or tissue sample with an imaging technique.

The present application further provides a method of detecting myeloperoxidase activity in a subject. In some embodiments, the method comprises:

i) administering to the subject a compound provided herein (e.g., a compound of any of Formulas I-VI, or a pharmaceutically acceptable salt thereof); and ii) imaging the subject with an imaging technique.

The present application further provides a method of monitoring treatment of a disease or disorder associated with abnormal myeloperoxidase (MPO) activity in a subject, the method comprising:

i) administering to the subject a compound provided herein (e.g., a compound of any of Formulas I-VI, or a pharmaceutically acceptable salt thereof);

ii) imaging the subject with an imaging technique;

iii) administering to the subject a therapeutically effective amount of a therapeutic compound to treat the disease or disorder;

iv) imaging the cell or tissue in the subject with an imaging technique; and v) comparing the image of step i) and the image of step iv).

In some embodiments, the method further comprises administering to the subject a compound provided herein (e.g., a compound of any of Formulas I-VI, or a pharmaceutically acceptable salt thereof) after the administering of step iii) and prior to the imaging of step iv). In some embodiment, the therapeutic compound is useful in the treatment of a disease or disorder associated with abnormal myeloperoxidase (MPO) activity. In some embodiments, the therapeutic compound is a therapeutic compound provided herein.

In some embodiments, the imaging technique is selected from the group consisting of fluorescence imaging and positron emission tomography (PET). In some embodiments, the imaging technique is fluorescence imaging. In some embodiments, the fluorescence imaging is selected from the group consisting of fluorescence molecular tomography (FMT) and fluorescence refractory imaging (FRI). In some embodiments, the imaging technique is positron emission tomography.

In some embodiments, the compound is:

(3)

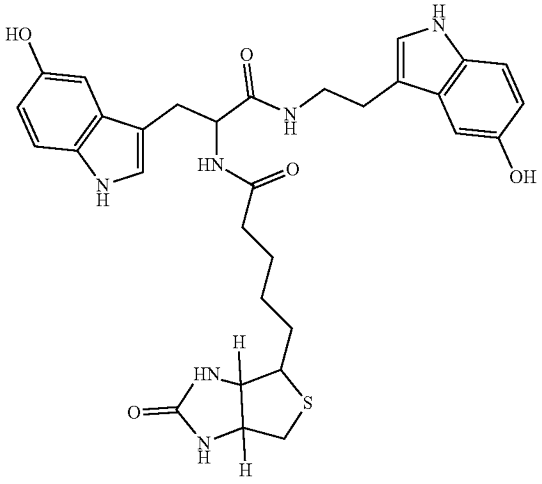

and the imaging technique is fluorescence imaging. In some embodiments, the fluorescence imaging is selected from the group consisting of fluorescence molecular tomography (FMT) and fluorescence refractory imaging (FRI).

In some embodiments, the compound is selected from the group consisting of:

(5)

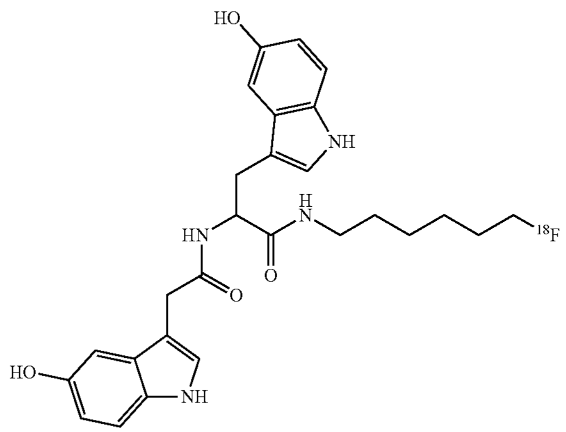

(7)

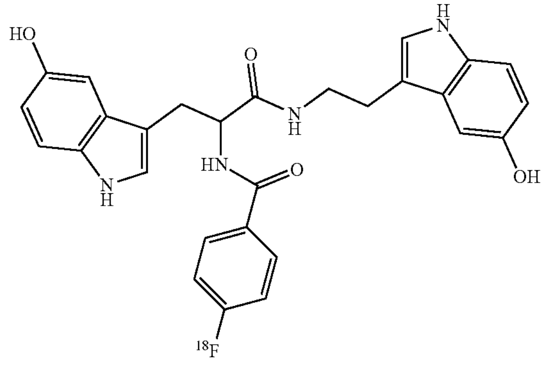

(9)

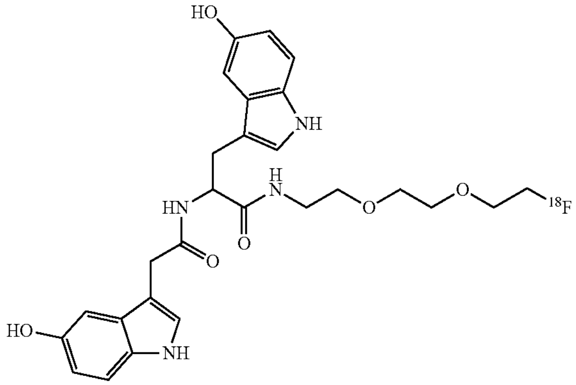

(13)

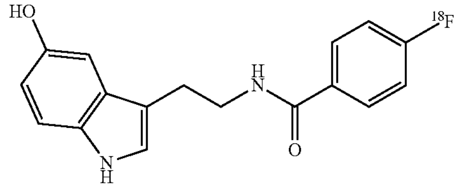

(15)

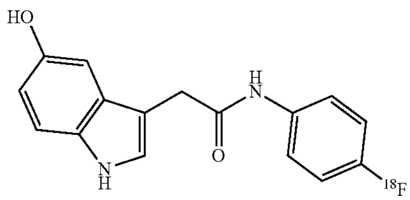

and

-continued (17)

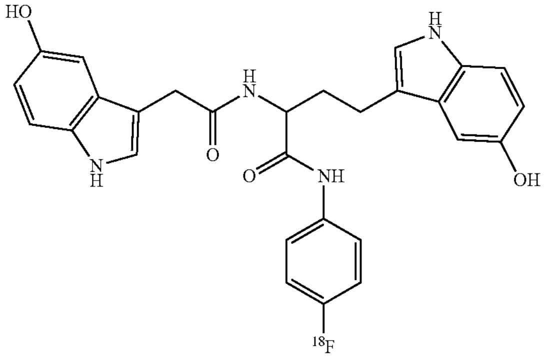

and the imaging technique is positron emission tomography.

In some embodiments, the disease or disorder associated with abnormal myeloperoxidase activity is selected from the group consisting of cancer, a rheumatic disease, an infectious disease, a disease of the central nervous system, a cardiovascular disorder, an autoimmune disorder, and inflammation associated with one or more of a cancer, a rheumatic disease, an infectious disease, a disease of the central nervous system, a cardiovascular disorder, and an autoimmune disorder. In some embodiments, the disease or disorder associated with abnormal myeloperoxidase activity is selected from the group consisting of cancer, a rheumatic disease, an infectious disease, a disease of the central nervous system, a cardiovascular disorder, and an autoimmune disorder. In some embodiments, the disease or disorder associated with abnormal myeloperoxidase activity is selected from the group consisting of inflammation associated with one or more of a cancer, a rheumatic disease, an infectious disease, a disease of the central nervous system, a cardiovascular disorder, and an autoimmune disorder.

In some embodiments, the disease or disorder associated with abnormal myeloperoxidase activity is a cancer. In some embodiments, the cancer comprises a solid tumor. In some embodiments, the cancer is a solid tumor. In some embodiments, the cancer is selected from the group consisting of bladder cancer, breast cancer, carcinoma, cervical cancer, colorectal cancer, endometrial cancer, glioma, cancer of the head and neck, liver cancer, lung cancer, melanoma, ovarian cancer, pancreatic cancer, prostate cancer, renal cancer, skin cancer, stomach cancer, testicular cancer, leukemia, and thyroid cancer. In some embodiments, the cancer is a solid tumor associated with one or more of bladder cancer, breast cancer, carcinoma, cervical cancer, colorectal cancer, endometrial cancer, glioma, cancer of the head and neck, liver cancer, lung cancer, melanoma, ovarian cancer, pancreatic cancer, prostate cancer, renal cancer, skin cancer, stomach cancer, testicular cancer, thyroid cancer, or any combination thereof. In some embodiments, the disease or disorder associated with abnormal myeloperoxidase activity is inflammation associated with one or more cancers selected from the group consisting of bladder cancer, breast cancer, carcinoma, cervical cancer, colorectal cancer, endometrial cancer, glioma, cancer of the head and neck, liver cancer, lung cancer, melanoma, ovarian cancer, pancreatic cancer, prostate cancer, renal cancer, skin cancer, stomach cancer, testicular cancer, thyroid cancer, leukemia, or any combination thereof.

In some embodiments, the disease or disorder associated with abnormal myeloperoxidase activity is a disease of the central nervous system. In some embodiments, the disease of the central nervous system is selected from the group consisting of Alzheimer's disease, stroke, epilepsy, Parkinson's disease, and inflammation associated with Alzheimer's disease, stroke, epilepsy, and Parkinson's disease. In some embodiments, the disease of the central nervous system is selected from the group consisting of Alzheimer's disease, stroke, epilepsy, and Parkinson's disease. In some embodiments, the disease of the central nervous system is inflammation associated with one or more of Alzheimer's disease, and stroke, epilepsy, and Parkinson's disease.

In some embodiments, the disease or disorder associated with abnormal myeloperoxidase activity is a cardiovascular disorder. In some embodiments, the cardiovascular disorder is selected from the group consisting of atherosclerosis, myocardial infarction, atrial fibrillation, vasculitis, and inflammation associated with one or more of atherosclerosis, myocardial infarction, atrial fibrillation, and vasculitis. In some embodiments, the cardiovascular disorder is selected from the group consisting of atherosclerosis, myocardial infarction, atrial fibrillation, and vasculitis. In some embodiments, the cardiovascular disorder is inflammation associated with one or more of atherosclerosis, myocardial infarction, atrial fibrillation, and vasculitis.

In some embodiments, the disease or disorder associated with abnormal myeloperoxidase activity is an autoimmune disorder. In some embodiments, the autoimmune disorder is selected from the group consisting of multiple sclerosis, meningitis, encephalitis, and inflammation associated with one or more of multiple sclerosis, meningitis, and encephalitis. In some embodiments, the autoimmune disorder is inflammation associated with one or more of multiple sclerosis, meningitis, and encephalitis.

In some embodiments, the disease or disorder associated with abnormal myeloperoxidase activity is a rheumatic disease. In some embodiments, the rheumatic disease is selected from the group consisting of rheumatoid arthritis, osteoarthritis, and inflammatory arthritis. In some embodiments, the rheumatic disease is inflammatory arthritis. In some embodiments, the inflammatory arthritis is selected from the group consisting of gout and calcium pyrophosphate deposition disease (CPPD). In some embodiments, the disease or disorder associated with abnormal myeloperoxidase activity is inflammation associated with one or more of rheumatoid arthritis, osteoarthritis, and inflammatory arthritis.

In some embodiments, the disease or disorder associated with abnormal myeloperoxidase activity is an infectious disease. In some embodiments, the infectious disease is a fungal disease or a bacterial disease. In some embodiments, the fungal disease is a disease associated with *C. albicans*. In some embodiments, the infectious disease comprises a yeast infection. In some embodiments, the yeast infection is an infection associated with *C. tropicalis*. In some embodiments, the disease or disorder associated with abnormal myeloperoxidase activity is inflammation associated with an infectious disease or a bacterial disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a subject or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder reversing the pathology and/or symptomatology) such as decreasing the severity of disease or reducing or alleviating one or more symptoms of the disease.

Combination Therapies

One or more additional therapeutic agents such as, for example, anti-inflammatory agents, steroids, immunosuppressants, chemotherapeutic agents, or other agents such as therapeutic antibodies, can be used in combination with the compounds of the present application for treatment of the diseases provided herein.

Example antibodies for use in combination therapy include but are not limited to trastuzumab (e.g. anti-HER2), ranibizumab (e.g. anti-VEGF-A), bevacizumab (e.g. anti-VEGF), panitumumab (e.g. anti-EGFR), cetuximab (e.g. anti-EGFR), rituxan (anti-CD20) and antibodies directed to c-MET.

Example steroids include corticosteroids such as cortisone, dexamethasone, hydrocortisone, methylprednisolone, prednisolone, and prednisone.

Example anti-inflammatory compounds include aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example immunosuppressants include azathioprine, chlorambucil, cyclophosphamide, cyclosporine, daclizumab, infliximab, methotrexate, and tacrolimus.

One or more of the following agents may be used in combination with the compounds provided herein and are presented as a non-limiting list: a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, tipifamib, gefitinib, erlotinib hydrochloride, antibodies to EGFR, imatinib mesylate, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, rituximab, alemtuzumab, clofarabine, cladribine, aphidicolin, sunitinib, dasatinib, tezacitabine, triapine, didox, trimidox, amidox, bendamustine, ofatumumab, and idelalisib.

In some embodiments, the additional therapeutic agent is useful for the treatment of multiple sclerosis. In some embodiments, the additional therapeutic agent is selected from the group consisting of interferon beta-1a, interferon beta-1b, peginterferon beta-1a, glatiramer acetate, teriflunomide, fingolimod, mitoxantrone, dimethyl fumarate, natalizumab, ozanimod, laquinimod, alemtuzumab, daclizumab, rituximab, ocrelizumab, and ofatumumab.

Pharmaceutical Compositions and Formulations

When employed as pharmaceuticals, the compounds provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, (e.g., intrathecal or intraventricular, administration), Parenteral administration can be in the form of a single bolus dose, or may be, for example, by a continuous perfusion pump. In some embodiments, the compounds provided herein are suitable for parenteral administration. In some embodiments, the compounds provided herein are suitable for intravenous administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the compositions provided herein are suitable for intravenous administration.

Also provided are pharmaceutical compositions which contain, as the active ingredient, a compound provided herein (e.g., a compound of any of Formulas I-VI, or a pharmaceutically acceptable salt thereof), in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyyinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, however, that the amount of the compound actually administered will usually be determined by a physician, according to the relevant circumstances, including the chosen route of administration, the actual compound administered, the age, weight, and response of the individual subject, the severity of the subject's symptoms, and the like.

EXAMPLES

The invention is further described in the following examples, which do not limit the scope of the invention described in the claims.

General Methods and Materials

All of the chemicals required for this work were obtained from Sigma Chemical Co. unless otherwise stated. 5-Hydroxy-L-tryptophan was obtained from Chem-Impex Imt'l Inc. (Wood Dale, Ill.). 5-Hydroxytryptamine was obtained from Alfa Aesar (Ward Hill, Mass.). Myeloperoxidase was obtained from Lee Biosolutions (St. Louis. Mo.). Matrigel Matrix was obtained from VWR international (Radnor, Pa.). Dulbecco's modified Eagle's medium (DMEM). Female C57Bl/6J mice (6-10 weeks) were purchased from Jackson Laboratory, Glucose oxidase (GOX) was purchased from Affymetrix (Santa Clara, Calif.).

Statistical analysis was performed using Prism 5.0 software (Graphpad, La Jolla, Calif.) P-values<0.05 were considered significant. Data were compared using the Student's t tester or Mann-Whitney U test. Correlation was determined by calculating the Pearson's correlation coefficient. Fluorescence intensity was quantified using ImageJ software, and results presented as relative fluorescence units (RFU).

Intermediate 1. (S)-3-(5-hydroxy-1H-indol-3-yl)-2-(2-(5-hydroxy-1H-indol-3-yl)acetamido)propanoic acid

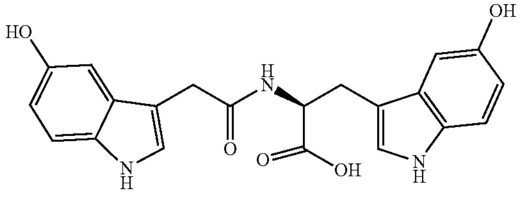 [SMILES: O=C(Cc1c[nH]c2ccc(O)cc12)N[C@@H](Cc1c[nH]c2ccc(O)cc12)C(=O)O]

To a solution of 2-(5-hydroxy-1H-indol-3-yl)acetic acid (191 mg, 1.0 equiv.) in DMF (3 mL) was added N-hydroxysuccinimide (126 mg, 1.1 equiv.) and N,N'-dicyclohexylcarbodiimide (DCC) (216 mg, 1.05 equiv.) at room temperature and the reaction mixture was stirred for 30 min. The solution was then filtered and added slowly to a solution of 5-hydroxytryptophan (264 mg, 1.2 equiv.) and trimethylamine ($Et_3N$) (280 μL, 2.0 equiv.) in DMF (3 mL). The reaction mixture was then stirred for another 1 h. After filtration, the solution was purified using reverse phase chromatography using a gradient of acetonitrile/water, 0-100% over 20 min to give the desired Intermediate 1 (243 mg, 62%). $^1$H NMR (500 MHz, DMSO) δ 12.52 (broad, 1H), 10.49 (s, 1H), 10.47 (s, 1H), 7.99 (d, J=8.0 Hz, 1H), 7.09 (m, 2H), 6.99 (s, 1H), 6.94 (s, 1H), 6.81 (m, 2H), 6.56 (m, 2H), 4.30 (dd, 1H), 3.95 (s, 1H), 3.41 (m, 2H), 3.03 (dd, 1H), 2.92 (dd, 1H); $^{13}$C NMR (125 MHz, DMSO) δ 173.4, 170.6, 150.2, 150.1, 130.6, 130.5, 128.0, 127.8, 124.0, 123.9, 111.6. 111.5, 111.25, 111.22, 108.7, 107.7, 102.6, 102.1, 52.8, 48.6, 27.3; LCMS found m/z 394.3 (M+1).

Intermediate 2. 2-(2-(2-fluoroethoxy)ethoxy)ethanamine (Intermediate 2f)

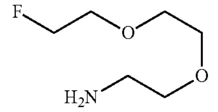

Step 1. (ethane-1,2-diylbis(oxy))bis(ethane-2,1-diyl) bis(4-methylbenzenesulfonate) (Intermediate 2a)

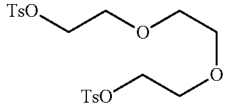 [SMILES: Cc1ccc(S(=O)(=O)OCCOCCOCCOS(=O)(=O)c2ccc(C)cc2)cc1]

To a solution of triethylene glycol (750 mg, 1.0 equiv.) in DCM (20 mL) was added triethylamine (2.1 mL, 3.0 equiv.) then tosyl chloride (2.29 g, 2.4 equiv.) portionwise and the reaction mixture was stirred at room temperature for 2 h. The reaction mixture was washed with saturated $NH_4Cl$ solution (20 mL×3), then by brine. The resulting mixture was subsequently dried and evaporated. The residue was purified using flash column in the eluent of ethyl acetate/hexane (1/5, then 1/1) to give a white powder (2.11 g, 92%). $^1$H NMR (500 MHz, DMSO) δ 7.77 (d, J=8.0 Hz, 4H), 7.46 (d, J=8.0 Hz, 4H), 4.09 (t, 4H), 3.53 (t, 4H), 3.38 (t, 4H), 2.41 (s, 6H); $^{13}$C NMR (125 MHz, DMSO) δ 145.3, 132.9, 130.6, 128.1, 70.4, 70.0, 68.3, 21.5, LCMS found m/z 459.5; (M+1).

Step 2. 2-(2-(2-azidoethoxy)ethoxy)ethyl 4-methylbenzenesulfonate (Intermediate 2b)

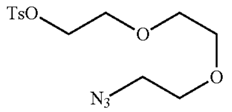

To a solution of intermediate 2a (138 g, 1.0 equiv.) in DMSO was added sodium azide (191 mg, 0.95 equiv.) portion-wise and the reaction was heated to 60° C. and stirred for 1 h. The reaction was allowed to cool to room temperature and was extracted with water and ethyl acetate (15 mL×3), the combined organic phase was washed with brine, dried, and evaporated. The residue was purified using flash chromatography with the eluent of ethyl acetate/hexane (1/4) to give the desired compound 2b (593 mg, 58%). $^1$H NMR (500 MHz, DMSO) δ 7.78 (d, J=8.0 Hz, 2H), 7.47 (d, J=8.0 Hz, 2H), 4.10 (t, 2H), 3.60 (m, 6H), 3.49 (t, 2H), 3.40 (t, 2H), 2.49 (s, 3H), $^{13}$C NMR (125 MHz, DMSO) δ 145.3, 132.9, 130.6, 128.1, 70.4, 70.2, 70.0, 69.7, 68.4, 50.4, 21.5; LCMS found m/z 330.2 (M+1).

Step 3. 2-(2-(2-aminoethoxy)ethoxy)ethyl 4-methylbenzenesulfonate (Intermediate 2c)

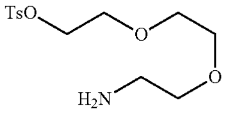

To a solution of intermediate 2b (494 mg, 1 equiv.) in anhydrous THF (5 mL) was added triphenylphosphine (786 mg, 2 equiv.) portion-wise at 0° C. The reaction was warmed to room temperature and stirred for another 5 h. Then two drops of water were added and the reaction mixture was stirred for 2 h. 3 mL of 1 M HCl was then added to the reaction mixture, the THF was evaporated, and the aqueous phase washed with ethyl acetate. Then the above solution was purified using reverse phase chromatography using a gradient of acetonitrile/water, 0-100% over 20 min) to give the desired intermediate 2c (377 mg, 83%). $^1$H NMR (500 MHz, DMSO) δ 7.79 (broad, 2H), 7.78 (s, 1H), 7.50 (t, J=8.0 Hz, 2H), 7.12 (t, J=8.0 Hz, 2H), 4.10 (m, 1H), 3.58 (m, 6H), 3.54 (t, 2H), 3.49 (m, 1H), 2.96 (t, 2H), 2.41 (s, 3H); $^{13}$C NMR (125 MHz, DMSO) δ 145.8, 132.8, 130.6, 128.5, 72.7, 70.4, 70.1, 68.4, 67.1, 60.6, 21.2; LCMS found m/z; 304.1 (M+1).

Step 4. 2,2-dimethyl-4-oxo-3,8,11-trioxa-5-azatridecan-13-yl 4-methylbenzenesulfonate (Intermediate 2d)

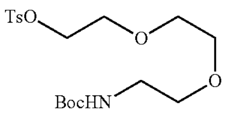 [SMILES: Cc1ccc(S(=O)(=O)OCCOCCOCCNC(=O)OC(C)(C)C)cc1]

To a solution of intermediate 2c (303 mg, 1.0 equiv.) in DCM (5 mL) was added $Et_3N$ (1.5 equiv.) and di-tert-butyldicarbonate ($Boc_2O$)(1.2 equiv.) at room temperature and the reaction was stirred for 2 h. The reaction solution was evaporated and extracted with ethyl acetate (5×3 mL×3), washed by brine (3 mL×3), dried over anhydrous $Na_2SO_4$, and evaporated to give intermediate 2d without further purification.

Step 5. tert-butyl (2-(2-(2-fluoroethoxy)ethoxy) ethyl)carbamate (Intermediate 2e)

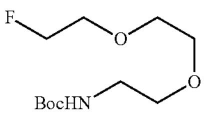

To a solution of intermediate 2d in THF (4 mL) was added the solution of tetrabutylammonium fluoride (TBAF) (1 mL, 2 M) and the reaction mixture was heated to 60° C. and stirred for 30 min. The solvent was evaporated and the resulting residue was extracted with ethyl acetate (5 mL×3), washed by brine (3 mL×3), dried over anhydrous $Na_2SO_4$, and evaporated. The residue was washed through silica pad with the eluent of ethyl acetate/hexane in the ratio of 1/3 to give the intermediate 2e.

Step 6. 2-(2-(2-fluoroethoxy)ethoxy)ethanamine (Intermediate 2f)

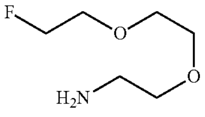

Intermediate 2e was added to a mixture of 10% trifluoroacetic acid (TFA) in DCM (2 mL) at room temperature and stirred for 30 min. The TFA and solvent were removed by evaporation and the residue was purified using flash chromatography with gradient DCM/MeOH (95/5 to 90/10 containing 1% $Et_3N$) to give intermediate 2f. The overall yield of the three steps is 50%. $^1$H NMR (500 MHz, DMSO): 8.31 (broad, 2H), 4.56 (m, 1H), 4.46 (m, 1H), 3.68 (m, 1H), 3.62 (m, 3H), 3.58 (m, 4H), 2.92 (m, 2H); $^{13}$C NMR (125 MHz, DMSO): 84.2, 82,9, 70.2, 70.1, 67.0, 39.6. LCMS found m/z: 152.1 (M+1).

Example 1

(S)—N-(2-(2-(2-fluoroethoxy)ethoxy)ethyl)-3-(5-hydroxy-1H-indol-3-yl)-2-(2-(5-hydroxy-1H-indol-3-yl)acetamido)propanamide (Compound 8)

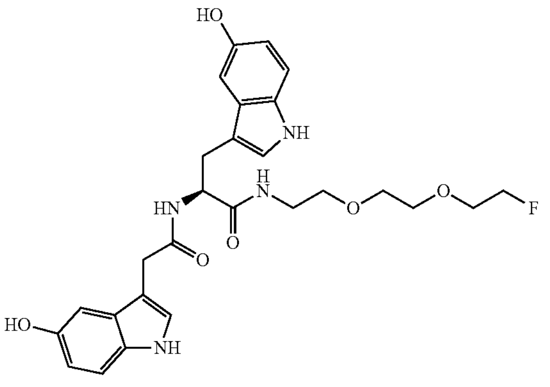 [SMILES: O=C(Cc1c[nH]c2ccc(O)cc12)N[C@@H](Cc1c[nH]c2ccc(O)cc12)C(=O)NCCOCCOCCF]

To a solution of Intermediate 1 (80 mg, 1.0 eq.) in DMF (2 mL) was added hydroxybenzotriazole (HOBt) (48 mg, 1.5 eq.) and N-(3-dimethylaminopropyl)-N'-ethylcarbodiimide hydrochloride (EDC-HCl) (51 mg, 1.5 eq.) at room temperature. After stirring for 30 min, a solution of 2f (39 mg, 1.3 eq,) in DMF (1.5 mL) was added slowly and stirred at room temperature for another 1 h. The reaction mixture was purified by HPLC with 0/100 $CH_3CN/H_2O$/0.5% TFA as solvent system to give a white solid (58 mg, 55%), $^1$H NMR (500 MHz, DMSO) δ 10.50 (s, 1H), 10.38 (s, 1H), 7.82 (m, 2H), 7.10 (m, 2H), 6.99 (d, 1H), 6.91 (s, 1H), 6.85 (s, 1H), 6.82 (s, 1H), 6.58 (m, 2H), 4.53 (d, 1H), 4.46 (m, 1H), 4.43 (d, 1H), 3.63 (m, 1H), 3.57 (m, 1H), 3.48 (m, 2H), 3.47 (m, 1H), 3.44 (m, 3H), 3.25 (m, 2H), 3.17 (m, 1H), 2.93 (m, 1H), 2.82 (m, 1H) δ $^{13}C$ NMR (125 MHz, DMSO): 171.9, 170.9, 158.7, 150.7, 150.6, 131.1, 131.0, 128.6, 128.5, 124.6, 124.4, 112.0, 111.9, 109.4, 108.2, 103.1, 102.9, 84.1, 82.8, 70.1, 70.0, 69.2, 53.8, 49.1, 38.9, 33.0, 28.6, LCMS found m/z 527.1 (M+1).

Example 2

Alternative Synthesis of (S)—N-(2-(2-(2-fluoroethoxy)ethoxy)ethyl)-3-(5-hydroxy-1H-indol-3-yl)-2-(2-(5-hydroxy-1H-indol-3-yl)acetamido)propanamide (Compound 8)

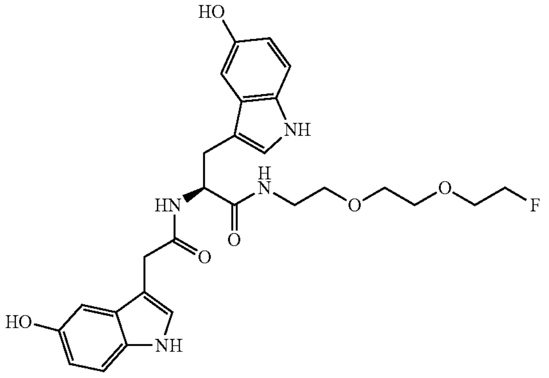 [SMILES: O=C(Cc1c[nH]c2ccc(O)cc12)N[C@@H](Cc1c[nH]c2ccc(O)cc12)C(=O)NCCOCCOCCF]

Step 1. (S)-1-(5-hydroxy-1H-indol-3-yl)-4-((5-hydroxy-1H-indol-3-yl)methyl)-2,5-dioxo-9,12-dioxa-3,6-diazatetrodecan-14-yl 4-methylbenzenesufonate

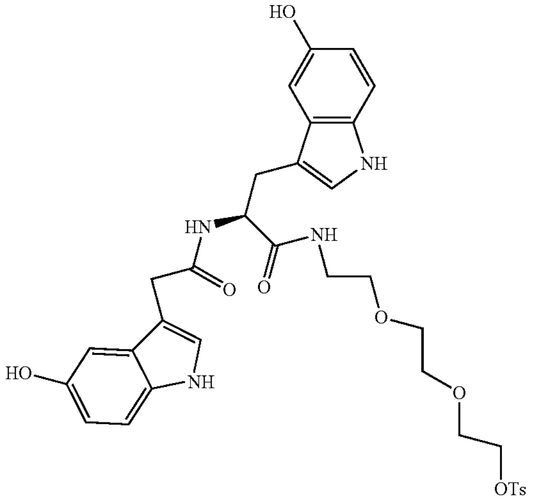 [SMILES: Cc1ccc(S(=O)(=O)OCCOCCOCCNC(=O)[C@H](Cc2c[nH]c3ccc(O)cc23)NC(=O)Cc2c[nH]c3ccc(O)cc23)cc1]

To a solution of Intermediate 1 (236 mg, 1.0 eq.) in DMF (3 mL) was added HOBt (121 mg, 1.5 eq.) and EDC-HCl (172 mg, 1.5 eq.) at room temperature. After stirring for 30 min, a solution of Intermediate 2c (265 mg, 1.3 eq.) DMF (1.5 mL) was added dropwise, and the reaction mixture was stirred at room temperature for 1 h. The reaction mixture was extracted with ethyl acetate (10 mL×3). The combined organic phase washed with brine, dried over anhydrous $Na_2SO_4$, and concentrated to dryness. The mixture was used for the next step without further purification.

Step 2. (S)-tert-butyl 3-(2-(2-(1-(tert-butoxycarbonyl)-5-((tert-butoxycarbonyl)oxy)-1H-indol-3-yl)acetamido)-3-oxo-3-((2-(2-(2-(tosyloxy)ethoxy)ethoxy)ethyl)amino)propyl)-5-((tert-butoxycarbonyl)oxy)-1H-indole-1-carboxylate

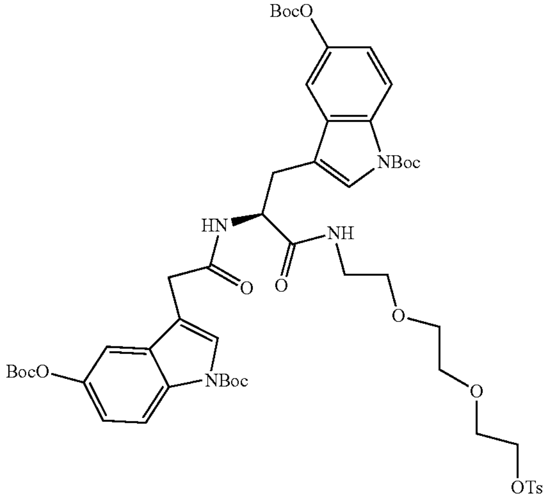

To the suspension of the compound prepared in Step 1, (270 g, 1.0 equiv.) in DCM (5 mL) was added $Boc_2O$ (380 mg, 4.4 equiv.), $NEt_3$ (340 μL, 6 equiv.) and N,N-dimethylaminopyridine (19 mg, 0.4 equiv.) at room temperature, and stirred for 30 min. The reaction mixture was concentrated and separated using flash chromatography with the eluent of hexane/ethyl acetate (4/1, then 1/1) to give the desired off-white powder (190 mg, 45%).

Step 3. (S)-tert-butyl 3-(2-(2-(1-(tert-butoxycarbonyl)-5-(tert-butoxycarbonyl)oxy)-1H-indol-3-yl)acetamido)-3-((2-(2-(2-fluoromethoxy)ethoxy)ethyl)amino)-3-oxopropyl)-5-((tert-butoxycarbonyl)oxy)-1H-indole-1-carboxylate

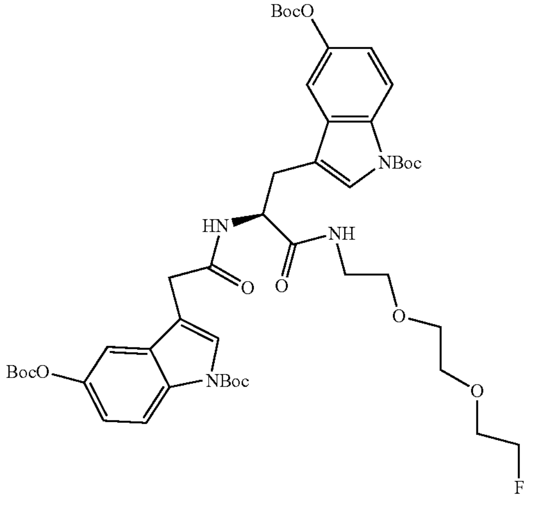

To a solution of 1 M TBAF in THF was added the product prepared in Step 2 (30 mg, 1.0 eq.). The reaction mixture was heated to 60° C. and stirred for 30 min. After cooling to room temperature, the solvent was evaporated and the resulting residue dissolved with ethyl acetate (9 mL). The combined organic phase washed by brine, dried over anhydrous $Na_2SO_4$, and concentrated. The mixture obtained was used in the next step without further purification. $^1$H NMR (500 MHz, DMSO) δ 8.48 (d, 1H), 8.17 (m, 1H), 7.8 (m, 1H), 7.52 (s, 1H), 7.51 (s, 1H), 7.43 (d, 1H), 7.33(d, 1H), 7.1 (m, 1H), 4.62 (dd, 1H), 4.06 (t, 2H), 3.52 (m, 2H), 3.37 (m, 4H), 3.34 (m, 4H), 3.29 (m, 2H), 2.98 (m, 1H), 2.87 (m, 1H), 1.60 (s, 9H), 1.57 (s, 9H), 1.49 (s, 9H), 1.48 (s, 9H); $^{13}$C NMR (125 MHz, DMSO) δ 171.4, 169.6, 152.2, 152.1, 149.2, 146.7, 146.6, 145.3, 132.8, 132.7, 131.4, 131.2, 130.5, 128.2, 118.5, 116.9, 115.7, 115.5, 112.5, 112.3, 110.3, 110.2, 84.2, 84.1, 83.4, 83.3, 70.4, 70.0, 69.9, 69.3, 68.3, 53.1, 42.3, 27.9 (overlap, 6), 27.7 (overlap, 6), 21.5. LCMS found m/z 928.0 (M+1).

Step 6. (S)—N-(2-(2-(2-fluoroethoxy)ethoxy)ethyl)-3-(5-hydroxy-1H-indol-3-yl)-2-(2-(5-hydroxy-1H-indol-3-yl)acetamido)propanamide

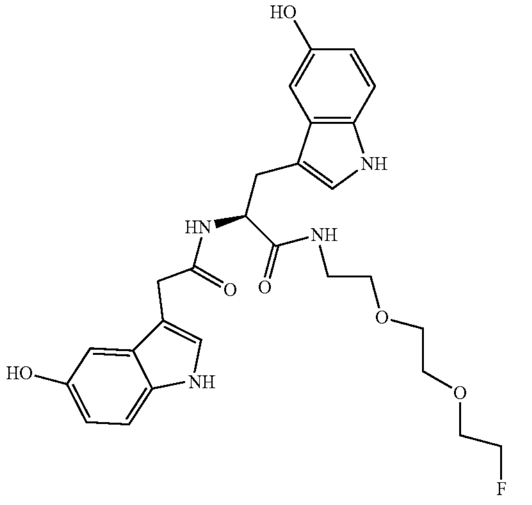 [SMILES: O=C(Cc1c[nH]c2ccc(O)cc12)N[C@@H](Cc1c[nH]c2ccc(O)cc12)C(=O)NCCOCCOCCF]

To 2 M HCl acetonitrile (0.5 mL) was added the product prepared in Step 5 (12 mg) and the reaction mixture was stirred at 60° C. for 30 min. The solvent was evaporated and the residue was separated using preparative HPLC to give the desired product. The overall yield for steps 5-6 was 60%.

Example 3

Synthesis of (S)—N-(6-fluorohexyl)-3-(5-hydroxy-1H-indol-3-yl)-2-(2-(5-hydroxy-1H-indol-3-yl)acetamido)propanamide (Compound 4)

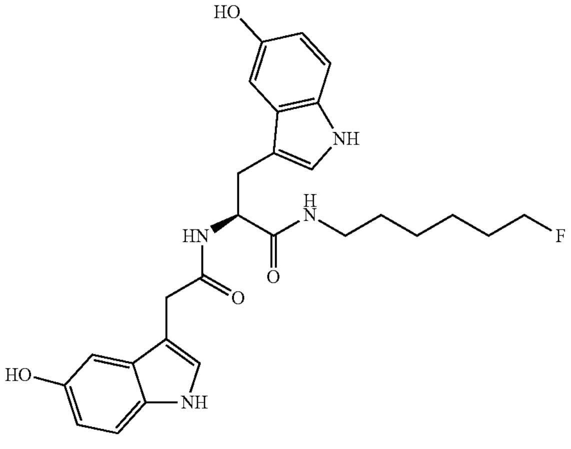 [SMILES: O=C(Cc1c[nH]c2ccc(O)cc12)N[C@@H](Cc1c[nH]c2ccc(O)cc12)C(=O)NCCCCCCF]

Compound 4 was prepared according to the procedures described for the preparation of Compound 8. $^1$H NMR (500 MHz, MISO) δ 10.50 (d, 1H), 10.41 (d, 1H), 8.54 (broad, $^1$H), 7.84 (d, 1H), 7.69 (m, 1H), 7.10 (m, 2H), 7.00 (d, 1H), 6.91 (d, 1H), 6.84 (m, 2H), 6.57 (m, 2H), 4.44 (m, 2H), 4.32 (m, 1H), 2.92 (m, 4H), 1.54 (m, 2H), 1.22 (m, 4H), 1.11 (m, 2H); $^{13}$C NMR (125 MHz, DMSO) δ: 171.0, 170.4, 150.2, 136.2, 130.6, 128.0, 124.1, 123.8, 122.8, 113.8, 111.5, 111.3, 111.1, 109.0, 107.8, 102.6, 90.1, 86.1, 84.5, 82.9, 80.9, 53.4, 41.3, 39.0, 38.4, 32.5, 29.8, 28.7, 25.8, 24.3; LCMS found m/z: 495.3 (M+1).

Example 4

Synthesis of (S)-4-fluoro-N-(3-(5-hydroxy-1H-indol-3-yl)-1-((2-(5-hydroxy-1H-indol-3-yl)ethyl)amino)-1-oxopropan-2-yl)benzamide (Compound 6)

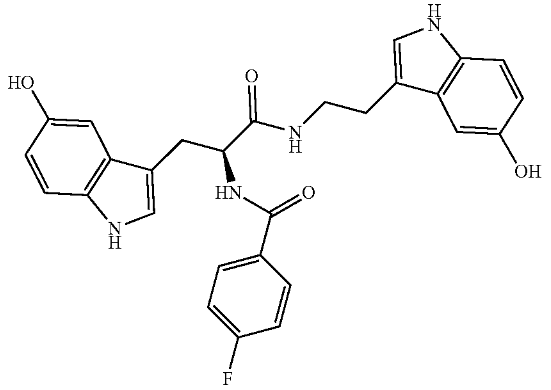 [SMILES: O=C(N[C@@H](Cc1c[nH]c2ccc(O)cc12)C(=O)NCCc1c[nH]c2ccc(O)cc12)c1ccc(F)cc1]

(S)-2-amino-3-(5-hydroxy-1H-indol-3-yl)-N-(2-(5-hydroxy-1H-indol-3-yl)ethyl)propanamide and intermediate 2k were reacted in the presence of triethylamine to provide cold Compound 6, as shown in Scheme 6. (S)-2-amino-3-(5-hydroxy-1H-indol-3-yl)-N-(2-(5-hydroxy-1H-indol-3-yl)ethyl)propanamide was prepared from Boc-protected 5-hydroxy-L-tryptophan and serotonin, treated with the coupling agent EDC and HOBt, and subsequent Boc-deprotection. Intermediate 2k was prepared by DCC coupling of 4-fluorobenzoic acid with NHS. $^1$H NMR (500 MHz, DMSO) δ 10.48 (d, 1H), 10.44 (d, 1H), 8.49 (d, 1H), 8.16 (m, 1H), 7.91 (m, 1H), 7.27 (m, 2H), 7.11 (m, 3H), 7.01 (m, 2H), 6.86 (d, 1H), 6.59 (m, 2H), 4.67 (m, 1H), 3.34 (m, 2H), 3.15 (dd, 1H), 3.04 (dd, 1H), 2.72 (m, 2H); 13C NMR (125 MHz, DMSO) δ: 171.5, 165.1, 162.6, 150.2, 130.8, 130.7, 130.2, 128.0, 127.9, 124.0, 123.1, 115.2, 114.7, 111.7, 111.5, 111.3, 111.2, 110.8, 109.7, 102.6, 102.3, 54.3, 39.2, 27.7, 25.3; LCMS found m/z (M+1): 501.3.

Example 5

N—((S)-3-(5-hydroxy-1H-indol-3-yl)-1-((2-(5-hydroxy-1H-indol-3-yl)ethyl)amino)-1-oxopropan-2-yl)-5-((3aS,4S,6aR)-2-oxohexahydro-1H-thieno[3,4-d]imidazol-4-yl)pentanamide (Compound 3)

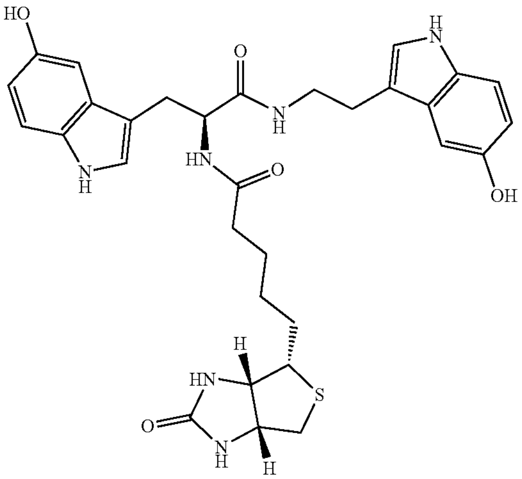 [SMILES: O=C(CCCC[C@@H]1SC[C@@H]2NC(=O)N[C@@H]21)N[C@@H](Cc1c[nH]c2ccc(O)cc12)C(=O)NCCc1c[nH]c2ccc(O)cc12]

Step 1. (S)-2-((tert-butoxycarbonyl)amino)-3-(5-hydroxy-1H-indol-3-yl)propanoic acid

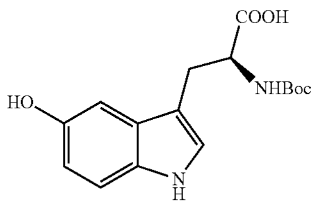 [SMILES: CC(C)(C)OC(=O)N[C@@H](Cc1c[nH]c2ccc(O)cc12)C(=O)O]

To a solution of $K_2CO_3$ (440 mg, 3.2 mmol) in water (4 mL), L-5-hydroxy tryptophan (5-HT, 330 mg, 1.5 mmol) was added. Next, a solution of di-tert-butyl dicarbonate (392 mg, 1.8 mmol) in THF (2 ml) was added to the solution and the reaction mixture was stirred at room temperature for 2 h. The reaction mixture was adjusted to pH 2-3 by addition of 1M HCl. After evaporating to remove THF, the resulting solution was extracted with ethyl acetate (10 mL×3), the organic phase washed with brine (5 mL×3), dried over anhydrous $Na_2CO_3$, and evaporated. The residue was separated using flash chromatography (ethyl acetate as eluent) to give the desired product (76%). $^1H$ NMR: 12.48 (s, 1H), 10.48 (s, 1H), 8.59 (s, 1H), 7.11 (d, J=8.0 Hz, 1H), 7.02 (d, J=2.0 Hz, 1H), 6.93 (D, J=8.5 Hz, 1H), 6.81 (d, J=2.0 Hz, 1H), 6.57 (dd, J1=8.5 Hz, J2=2.0 Hz, 1H), 4.09 (m, 1H), 3.00 (dd, J1=28 Hz, J2=5 Hz, 1H), 2.86 (dd, J1=28 Hz, J2=5 Hz, 1H); 1.32 (s, 9H); $^{13}C$ NMR: 174.0, 155.4, 150.2, 130.6, 127.7, 124.1, 111.7, 111.2. 109.1, 102.0, 78.0, 54.3, 28.2, 26.9; LCMS found m/z: 321.3 (M+1).

Step 2

(S)-tert-butyl (3-(5-hydroxy-1H-indol-3-yl)-1-((2-(5-hydroxy-1H-indol-3-yl)ethyl)amino)-1-oxopropan-2-yl)carbamate

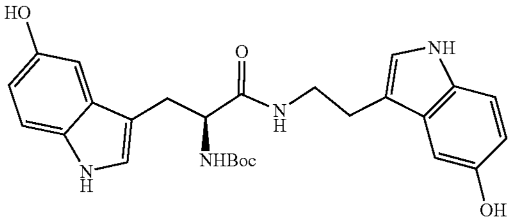 [SMILES: CC(C)(C)OC(=O)N[C@@H](Cc1c[nH]c2ccc(O)cc12)C(=O)NCCc1c[nH]c2ccc(O)cc12]

To a solution of the product of Step 1 (192 mg, 0.6 mmol) in DMF (3 mL) was added EDC.HCl (140 mg, 0.72 mmol) and HOBt (108 mg, 0.72 mmol), and the resulting mixture was stirred for 10 min. A solution of free-base serotonin (110 mg, 0.5 mmol) prepared in advance in DMF (2 mL) was then added and the reaction mixture was stirred for another 2 h. The reaction mixture was then extracted with ethyl acetate (10 mL×3), the organic layer washed by brine (5 mL×3), dried over anhydrous $Na_2CO_3$, and evaporated. The residue was separated using flash chromatography (ethyl acetate as eluent) to give a white solid (196 mg, (82%. $^1H$ NMR: 10.45 (s, 2H), 8.56 (s, 1H), 8.54 (s, 1H), 7.89 (t, 1H), 7.10 (d, J=8.5 Hz, 1H), 7.09 (d, 9.0 Hz, 1H), 7.0 (m, 2H), 6.88 (d, J=1.5 Hz, 1H), 6.83 (d, J=2.0 Hz, 1H), 6.67 (d, J=8.5 Hz, 1H), 6.57 (m, 2H), 4.12 (m, 1H), 3.26 (m, 2H), 2.96 (dd, J1=14.5 Hz, J2=4.5 Hz, 1H), 2.79 (dd, J1=14.5 Hz, J2=4.5 Hz, 1H), 2.66 (m, 2H), 1.32 (s, 9H); $^{13}C$ NMR: 171.8, 155.1, 150.15, 150.13, 130.8, 130.6, 128.1, 127.8, 123.9, 123.0, 111.6, 111.4, 111.2, 111.1, 110.7, 109.3, 102.5, 102.2, 77.9, 55.0, 40.1, 28.2, 28.0, 25.2; LCMS found m/z; 479.3 (M+1).

Step 3. N—((S)-3-(5-hydroxy-1H-indol-3-yl)-1-((2-(5-hydroxy-1H-indol-3-yl)ethyl)amino)-1-oxopropan-2-yl)-5-((3aS,4S,6aR)-2-oxohexahydro-1H-thieno[3,4-d]imidazol-4-yl)pentanamide

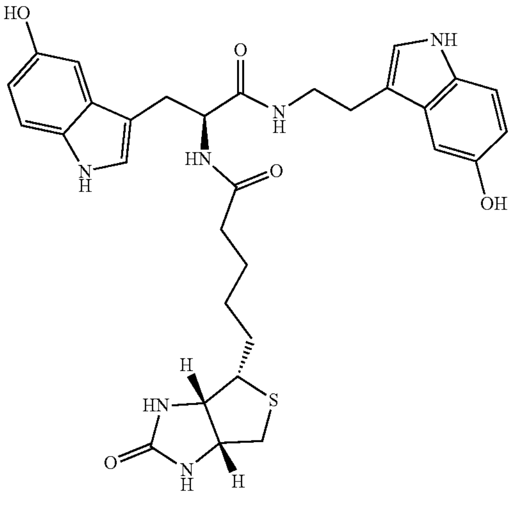 [SMILES: O=C(CCCC[C@@H]1SC[C@@H]2NC(=O)N[C@@H]21)N[C@@H](Cc1c[nH]c2ccc(O)cc12)C(=O)NCCc1c[nH]c2ccc(O)cc12]

To a solution of 10% TFA in DCM (2 mL) was added the product of Step 2 (95 mg), and the reaction mixture was stirred for 5 h at room temperature. Then the reaction mixture was evaporated to remove the solvent and used without further purification. To the solution of the obtained compound in DMF (2 mL) was added TEA (140 μL, 1 mmol) and biotin-NHS (54 mg, 0.16 mmol). The reaction mixture was stirred for 4 h at room temperature. The reaction mixture was then purified using preparative HPLC (gradient: 0-100% of acetonitrile/water) to give the desired product, Compound 3 (36 mg, 40%). $^1$H NMR: 10.5 (s, 1H), 10.4 (s, 1H), 7.96 (t, 1H), 7.89 (d, J=8.0 Hz, 1H), 7.10 (d, J=8.5 Hz, 1H), 7.09 (d, J=8.5 Hz, 1H), 6.99 (m, 2H), 6.88 (d, J=2.0 Hz, 1H), 6.82 (d, J=2.0 Hz, 1H), 6.57 (m, 2H), 6.39 (b, 2H), 4.47 (m, 1H), 4.26 (m, 1H), 4.04 (m, 1H), 3.26 (m, 2H), 3.00 (m, 2H), 2.78 (m, 3H), 2.65 (m, 2H), 2.07 (m, 2H), 1.55 (m, 1H), 1.42 (m, 3H), 1.20 (m, 2H); $^{13}$C NMR: 173.6, 173.2, 164.4, 151.8, 132.5, 132.3, 129.7, 129.5, 125.6, 124.8, 113.3, 113.1, 112.9, 112.8, 112.4, 111.0, 104.2, 103.9, 62.6, 60.9, 57.0, 54.9, 36.6, 29.7, 29.6, 29.5, 27.1, 26.9, 26.8, 26.0; LCMS found m/z: 605.3 (M+1).

Example 6

N—((S)-1-((2-(1H-indol-3-yl)ethyl)amino)-3-(1H-indol-3-yl)-1-oxopropan-2-yl)-5-((3aS,4S,6aR)-2-oxohexahydro-1H-thieno[3,4-d]imidazol-4-yl)pentanamide (Compound 18)

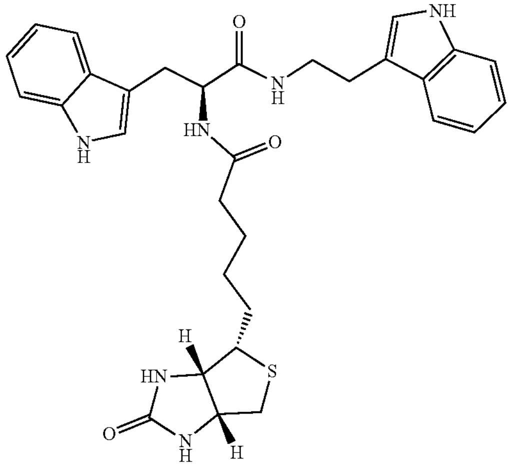 [SMILES: O=C(CCCC[C@@H]1SC[C@@H]2NC(=O)N[C@@H]21)N[C@@H](Cc1c[nH]c2ccccc12)C(=O)NCCc1c[nH]c2ccccc12]

The non-specific analogue, Compound 18, was synthetized according to the procedure described in Example 5, substituting L-tryptophan for 5-HT. L-tryptophan cannot be oxidized by MPO. $^1$H NMR (500 MHz, DMSO) δ: 10.80 (d, 1H), 10.77 (d, 1H), 8.02 (m, 1H), 7.93 (d, 1H), 7.58 (d, 1H), 7.52 (d, 1H), 7.32 (m, 2H), 7.10 (m, 2H), 7.05 (m, 2H), 6.95 (m, 2H), 6.38 (broad, 1H), 4.51 (dt, 1H), 4.27 (m, 2H), 4.05 (m, 2H), 3.31 (m, 2H), 2.99 (m, 3H), 2.76 (m, 3H), 2.55 (d, 2H), 2.07 (m, 2H); $^{13}$C NMR (125 MHz, DMSO) δ: 171.7, 171.3, 162.5, 136.0, 135.8, 127.1, 126.9, 123.2, 122.4, 120.7, 120.6, 118.3, 118.0 (2), 117.9, 111.5, 111.1, 111.0, 110.1, 60.7 (2), 59.0, 55.1, 53.1 (2), 34.7, 27.8, 27.7, 27.6, 24.9, 24.8. LCMS found m/z: 572.2 (M+1).

Example 7

Radiolabeling Chemistry

Figure 1A:
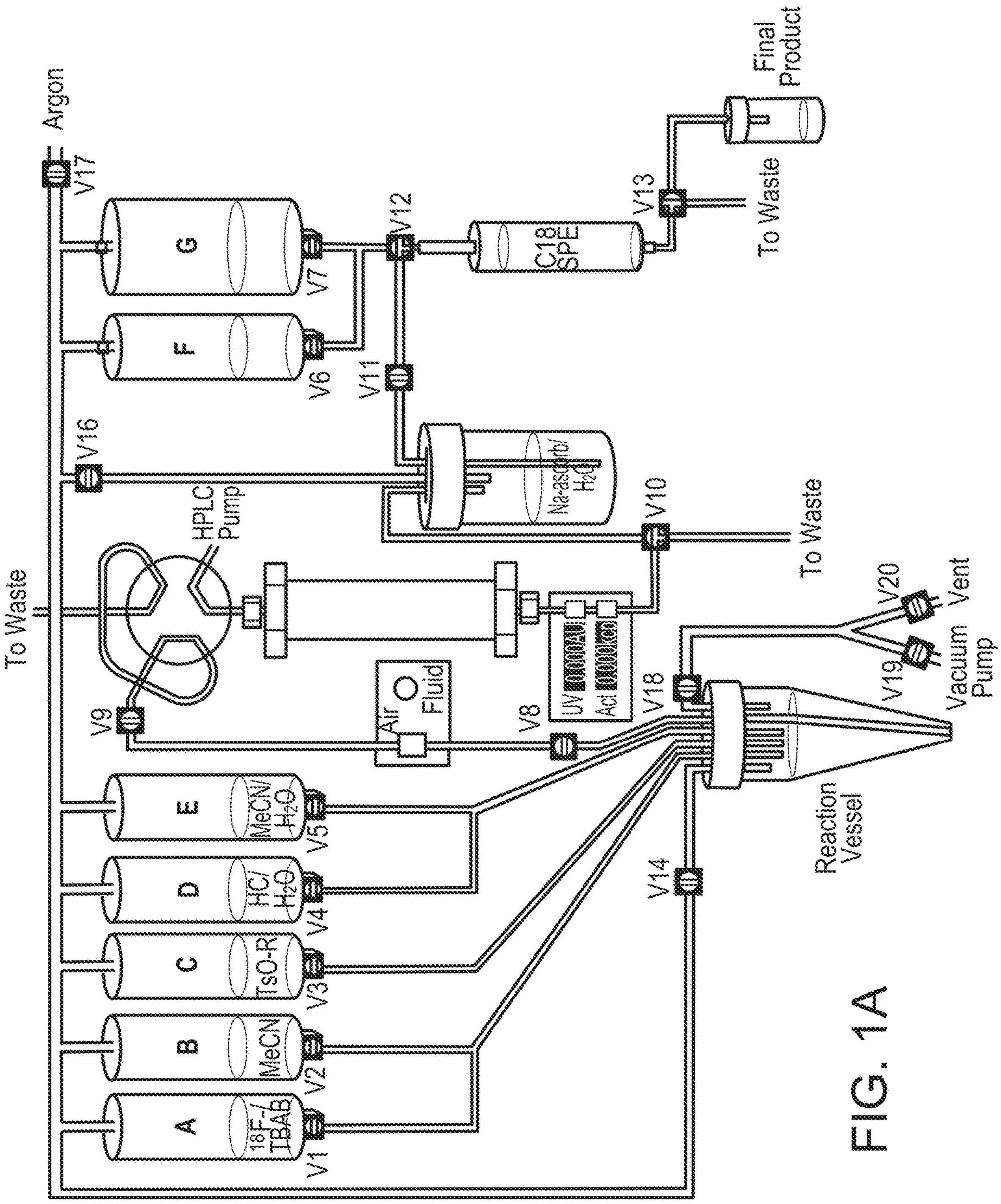
FIG. 1A shows an automated radiolabeling synthesis system used in the radiolabeling chemistry described in Example 8.

Radiolabeling chemistry was performed using automated synthesis of the following steps: (1) azeotropic drying of [$^{18}$F]-fluoride; (2) [$^{18}$F]-fluorination; (3) Boc deprotection; and (4) HPLC purification, followed by solid-phase formulation of the final product. The synthesis module was operated in the following sequences with numerical references to FIG. 1. Automated syntheses were performed on a Synthra (Hamburg, Germany) model RN Plus automated synthesizer module. Boc-deprotection was conducted with 0.4 mmol aqueous HCl at 95° C. added directly to the labeling reaction mixture without any prior purification. The two-step synthesis can be finished in approximately 80 min with the total radiochemical yield of 47% after decay correction.

1. [$^{18}$F]-Fluoride, received from PETNET (Waltham, Mass.), was produced by the $^{18}$O(p,n)$^{18}$F nuclear reaction and delivered to the reagent vial A (A) of the radiosynthesis module via syringe after mixing with tetrabutylammonium bicarbonate (TBAT, 75 mM in $H_2O$, 250 μL) and acetonitrile (MeCN, 300 μL).
2. Automated synthesis began with the addition the [$^{18}$F]-fluoride/TBAB mixture (A) and MeCN (B) to the reaction vessel 1 (RV1).
3. The mixture (RV1) was dried azeotropically at 65° C. under $N_2$ flow and vacuum over 5 min, then at 98° C. under $N_2$ flow and vacuum for 8 min, then cooled down to 50° C.
4. The TsO-protected precursor of Compound 8 (5 mg in 400 μL MeCN), pre-loaded into C, was added to RV1, RV1 was pressurized to 2 atm with argon (V14) and the reaction mixture was maintained at 70° C. for 10 min.
5. The reaction mixture was then cooled to 50° C., vented via valve V18, and hydrochloric acid (1.5 M in water, 400 μL) pre-loaded into D was added to RV1. The reactor was sealed via the closure of valve V18 and the reaction mixture was heated to 70° C. and this temperature was maintained for 17 min, then cooled to 30° C.
6. The reaction mixture (RV1) was diluted with a mixture of MeCN/$H_2O$ (25/370 μL) pre-loaded into E.
7. The crude reaction mixture (RV1) was transferred to the HPLC loop using argon pressure via a fluid detector (through V8 and V9), injected onto a semi-preparative column (Machery-Nagel Nucleodur Pyramid C18 semi-preparative, 250×10.00 mm, 5 μm), and eluted with 25:75 $CH_3CN/H_2O$ (0.075% formic acid) by volume at a flow rate of 5.5 mL/min. The eluent was monitored by UV (λ=254 nm) and radiochemical detectors connected in series.
8. A typical semi-preparative HPLC chromatogram is as follows. The fraction containing the major radiochemical product (tR=20.1 min) was collected, via valve 20, into a 50-mL dilution vessel, which was preloaded with 20 mL of 0.5% (w/v) aqueous sodium ascorbate.
9. The diluted HPLC fraction was then loaded onto a Sep-pak Plus C18 SPE cartridge (C18 SPE) (Waters; preactivated with 5 mL EtOH followed by 10 mL $H_2O$).
10. The C18 SPE cartridge was washed with 5 mL 0.5% (w/v) aqueous sodium ascorbate, preloaded into G to remove traces of salts, HPLC mobile phase, and [$^{18}$F] fluoride and then Compound 9 was eluted with 1.5 mL MeCN preloaded into F, into a collection vial.
11. This material was removed from the automated synthesis module and concentrated under reduced pressure.

Figure 1B:
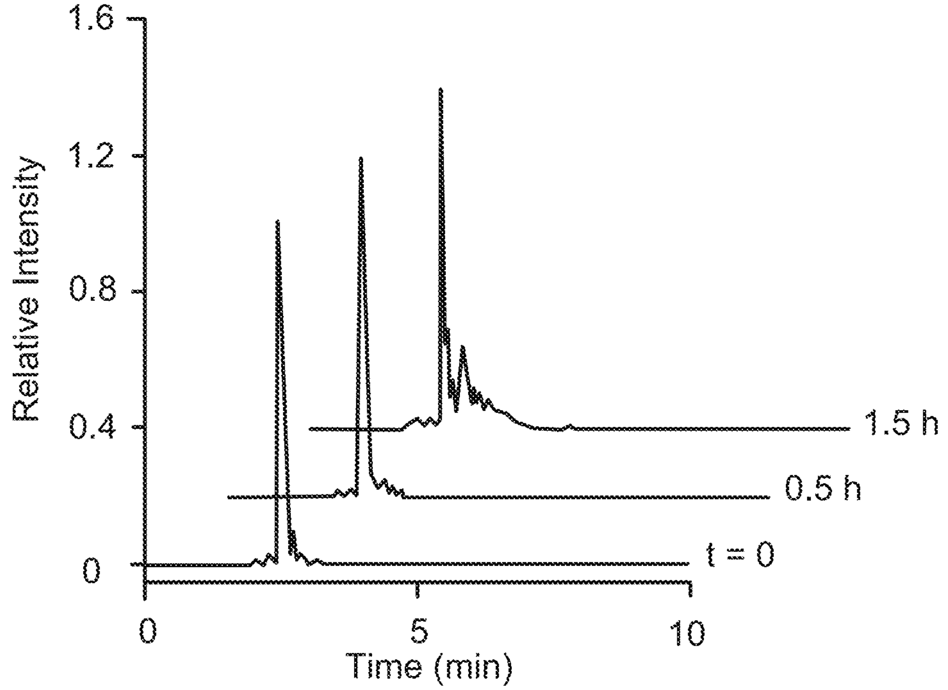
FIG. 1B shows the stability of Compound 9 stored in 1×PBS at room temperature for 0, 0.5 h and 1.5 h.
Figure 1C:
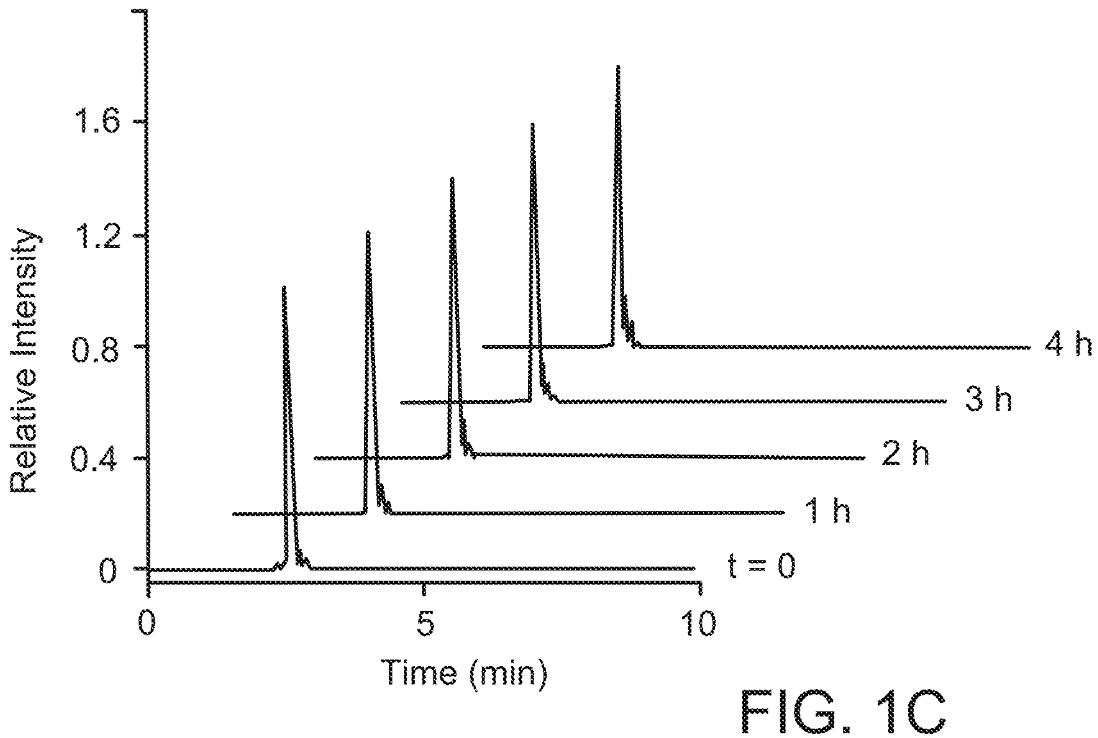
FIG. 1C shows the stability of Compound 9 stored in 0.5% Na-ascorbate (w/v) in saline at room temperature for 0, 1 h, 2 h, 3 h and 4 h.

Compound 9 degraded over time when stored in 1×PBS for injection at room temperature as shown in FIG. 1B. Without being bound by theory, it is speculated that the oxygen dissolved in the solvent caused degradation of the Compound 9. To inhibit degradation, 0.5% (w/v) aqueous sodium-ascorbate in saline was used instead for formulation, and the resulting Compound 9 was stable for at least 4 h at room temperature as shown in FIG. 1C.

Example 8

PET-CT Imaging
In Vivo Validation
Matrigel Experiment

300 μL of 1:1 mixture of matrigel and minimal essential medium (MEM) containing GOX and/or different concentrations of MPO (0, 15 μL, 30 μL) was injected subcutaneously into the ventral aspect of the thighs of the mouse. After 30 min, 300-600 μCi of MPO Compound 9 was injected intravenously. After 2 h, the mice were scanned using PET scanning.

Figure 2A:
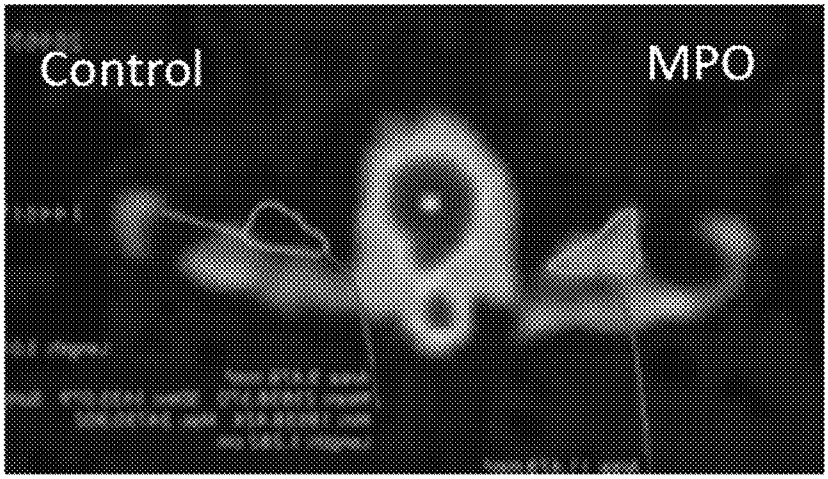
FIG. 2A shows Matrigel in vivo experiments with Compound 5. Control thigh: GOX: (4 μL, 1 mg/mL), MPO thigh: GOX (4 μL)+MPO (15 μL).
Figure 2B:
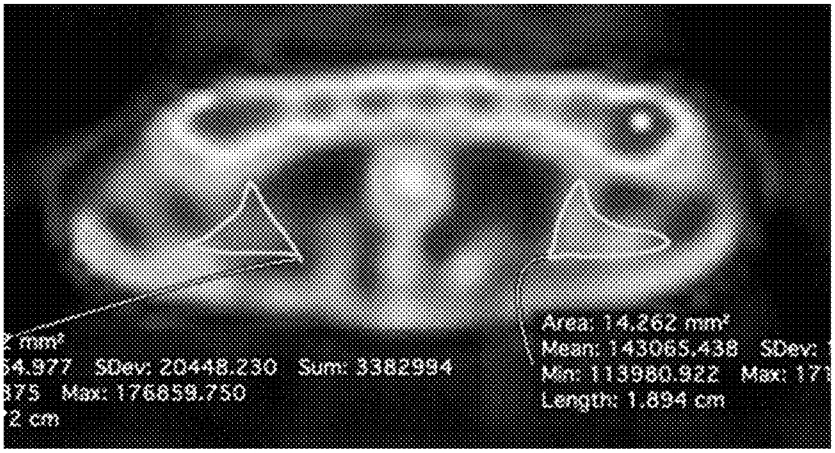
FIG. 2B shows Matrigel in vivo experiments with Compound 7. Control thigh: GOX (4 μL, 1 mg/mL), MPO thigh: GOX (4 μL)+MPO (15 μL).

To validate the efficacy of the MPO PET agents for in vivo applications, matrigel implantation experiments were performed by embedding MPO in matrigel along with glucose oxidase (GOX) as $H_2O_2$ donor. Matrigel is a gelatinous protein mixture that is liquid at 0° C. but forms a gel at body temperature while remaining diffusible to molecules from the bloodstream when injected into living animals (see e.g., Chen et al, *Radiology,* 2006, 240(2):473-481). The MPO/matrigel mixtures were injected subcutaneously to the thighs of the mice followed by injection of the MPO PET tracers 30 min later. As shown in FIGS. 2A-2C, Compound 9 demonstrated superiorities over Compounds 5 and 7, including high ratio of signal to background, lower liver and heart uptake and no observed defluorination. The signal of MPO side was around 1.7 fold higher compared to that of control side. Although Compound 5 gave similar signal of MPO side to that of control side (FIG. 2B), high heart and liver uptake and high background were observed from defluorination. Compound 7 gave both low signal and high heart uptake (FIG. 2A).

Figure 3A:
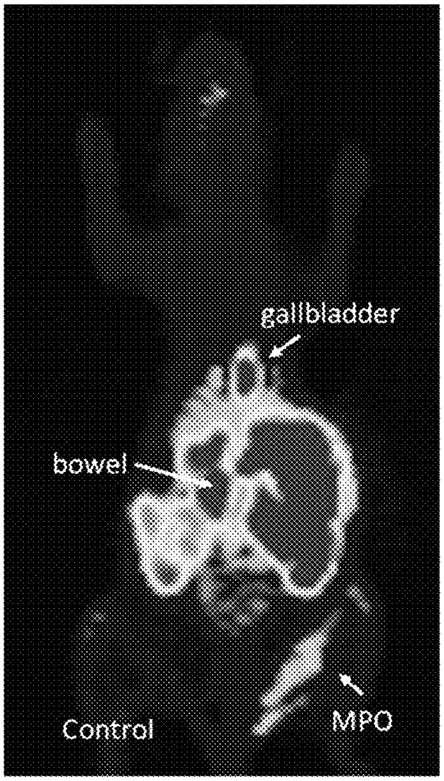
FIG. 3A shows representative results of MPO-PET matrigel imaging using Compound 9. Control thigh: GOX (4 μL, 1 mg/mL), MPO thigh: GOX (4 μL)+MPO (15 μL).
Figure 3B:
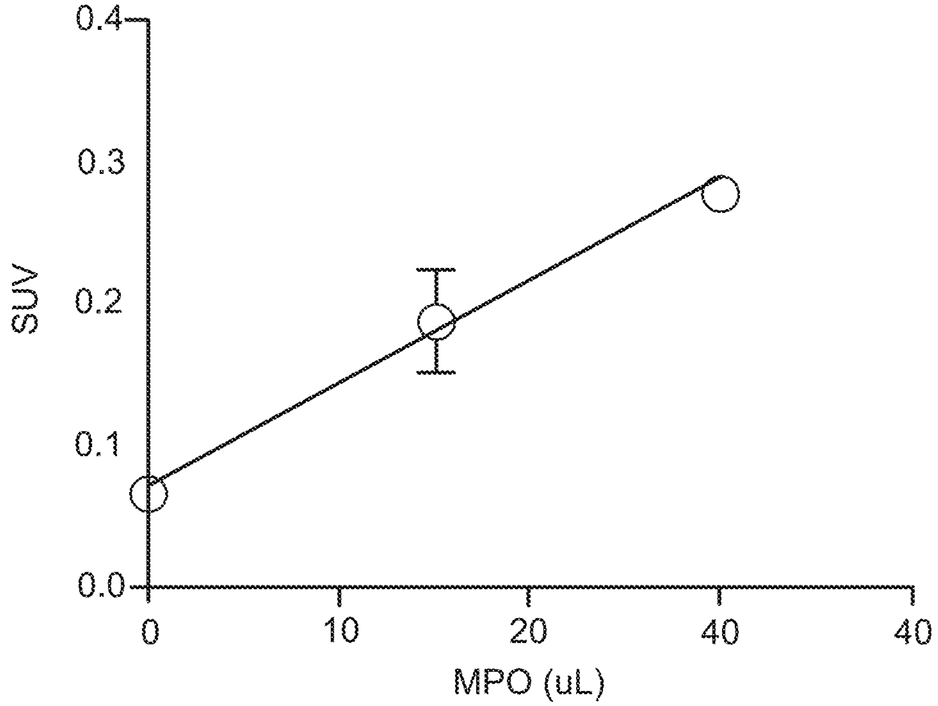
FIG. 3B shows representative results of the MPO-PET matrigel imaging experiment using Compound 9. The PET signal of matrigel experiment is linearly proportional to the concentration of MPO (0, 15 μL, 30 μL).

To verify the specificity of Compound 9 over MPO, different concentrations of MPO (0, 15 μL, 30 μL) were embedded in matrigel for the implantation experiments. A linear increase in signal was observed that was proportional to the MPO concentrations, as shown in FIG. 3B.

Pharmacokinetics and Biodistribution

Figure 4A:
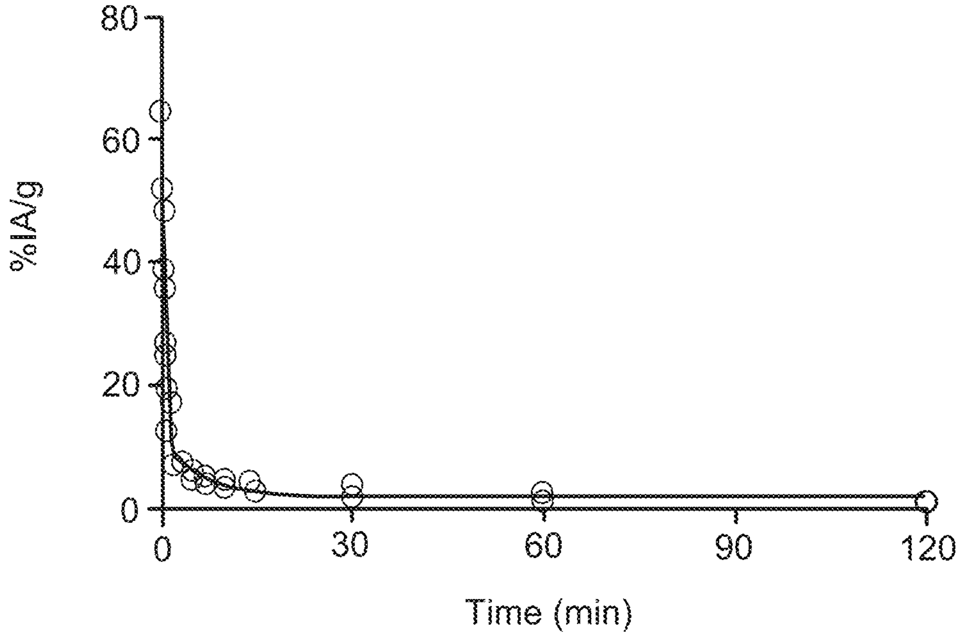
FIG. 4A shows the blood half-life of Compound 9.
Figure 4B:
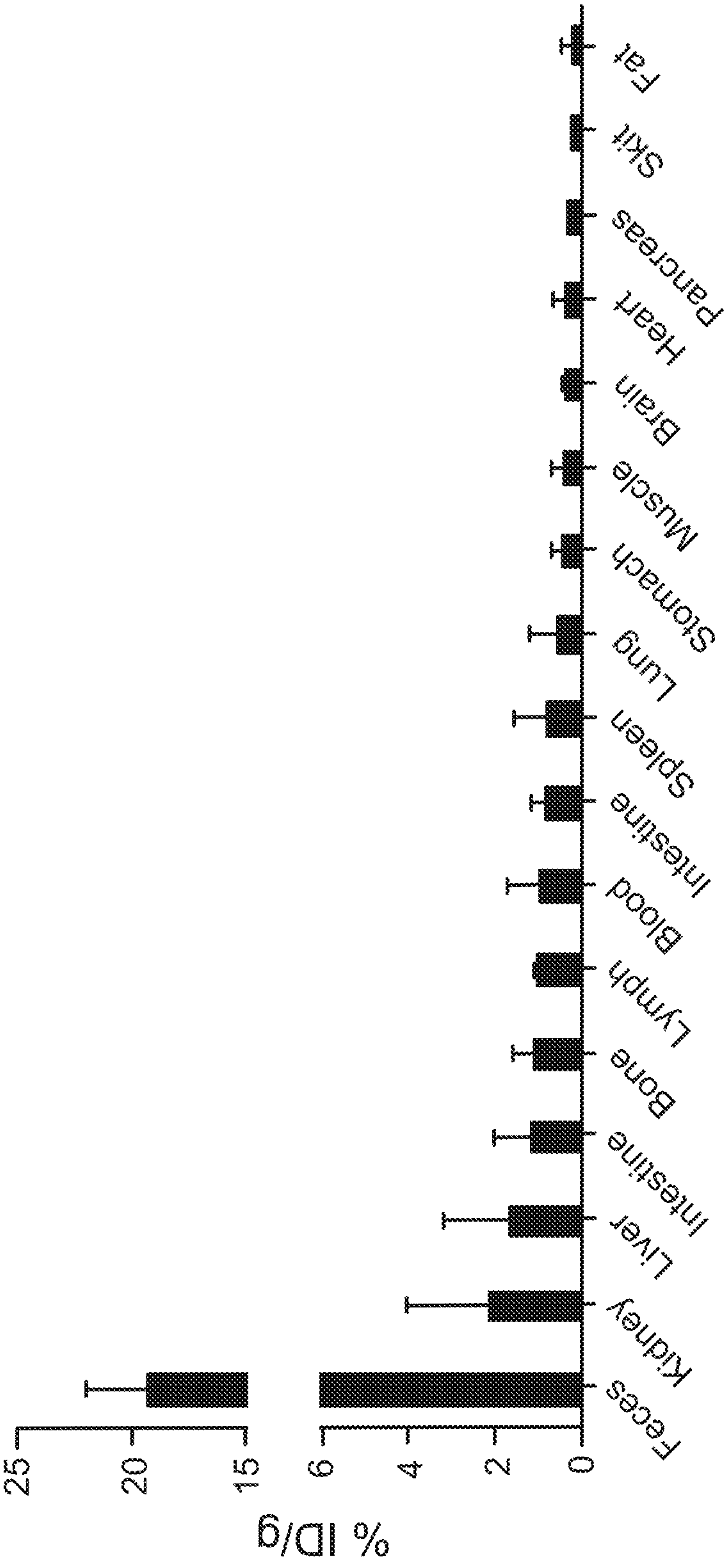
FIG. 4B shows the biodistribution of Compound 9 in various organs.

The pharmacokinetic and biodistribution of Compound 9 was evaluated in wild-type C57BL/6 mice. After systemic intravenous (i.v.) injection via the tail vein, blood samples were collected to determine clearance rate of Compound 9 from the blood. The major organs of the mouse were harvested and the radioactivity was measured. Data was fit by a two-phase exponential decay model to give 0.26 min short half-life and a 4.66 min slow half-life with the fast half-life accounting for 94.7% of the clearance, as shown in FIG. 4A. The biodistribution of various organs are shown in FIG. 4B. Besides feces, the liver and kidney showed the highest radioactivity, followed by bone and lymph.

FIG. 5A-5D shows results of an MPO dynamic study using Compound 9.

CFA Inflammation and Treatment by MPO Inhibitor PF-1355

Each pair contained one treated and one untreated, number of pairs, n=3. The 1/1 emulsion of CFA/PBS (40 μL) was injected subcutaneously on the dorsal side of one forepaw under isoflurane anesthesia, and PBS (40 μL) was injected on the other forepaw as control. After 1 h, the treated group was given PF-1355 (50 mg/kg) by gavage, then treated every 6 h for another 3 times, and the control group was treated with vehicle (10 mL/kg) accordingly. After 24 h, 300-600 uCi of Compound 9 was injected intravenously. After another 2 h, each pair of the mice was scanned side by side.

After validating the efficacy of the MPO Compound 9 in matrigel experiments, the specificity of the agent in inflammation was investigated. Complete Freund's Adjuvant (CFA) or its emulsion can cause inflammation when injected subcutaneously to the animal. The CFA emulsion was injected to one dorsal side of the forepaw of the mouse and the other side was injected with PBS. After 24 h, Compound 9 was injected intravenously and scanned 2 h after injection. As shown in FIG. 6A, the signal of the CFA side was 4 fold higher than that of the vehicle injection. To further verify the specificity of the MPO Compound 9, the mice were treated with MPO inhibitor PF-1355 1 h after CFA emulsion injection and continuously every 6 h afterwards for 4 times before injecting the Compound 9. The control group was treated with vehicle after CFA injection. Then each pair of the mice from treated and untreated groups were scanned. The signal of treated group decreased significantly compared to that of the untreated group due to the inhibition of MPO activity by PF-1355, as shown in FIG. 6B. The mean inhibition percentage of the three pairs was 59%, as shown in Table 1.

TABLE 1

| Mouse pair # | PF-1355 treated | Untreated | Ratio | % Inhibition |
|---|---|---|---|---|
| 1 | .0555 | .168 | | |
| 2 | .0736 | .166 | | |
| 3 | .0575 | .121 | | |
| mean | .0622 | .152 | .410 | 59% |

These data demonstrate that Compound 9 is specific to inflammation and MPO activity and can be used as a treatment tracking agent to report the inflammatory progress. The values listed are in SUV.

Example 9

In Vivo Validation of Sensitivity and Specificity of Compound 3

Four to ten weeks old female C57BL/6J or MPO-knockout mice (from Jackson Laboratories, Bar Harbor, Me.) were used for all animal experiments. Mice were fed biotin free diet for 5 days before imaging with fluorescence molecular tomography (FMT) or fluorescence refractory imaging (FRI).

To validate sensitivity of the Compound 3, different concentrations of purified human MPO (Lee Biosolutions, St. Louis, Mo.) and glucose oxidase (GOX, as a $H_2O_2$ donor, Affymetrix, Santa Clara, Calif.) were embedded in a mixture of matrigel (BD Bioscience, San Jose, Calif.) and minimal essential medium (MEM, Corning, Corning, N.Y.), and injected 400 μL of this mixture subcutaneously into the ventral aspect of the thigh. After 30 min, 2 nmol of Compound 3 in 100 μL phosphate buffered saline (PBS) was injected intravenously. One hour later, 25 μL of streptavidin AlexaFluor-647 (2 mg/mL, SA-647, Invitrogen, Carlsbad, Calif.) was injected intravenously, and FMT was performed every 15 minutes for a total of 60 minutes. Mice were imaged on a dedicated FMT system (Perkin Elmer, Waltham, Mass.) at 635 nm excitation and 655 nm emission.

To validate specificity of the Compound 3, mice were injected with a 1:1 mixture of MEM and matrigel as above, containing a combination of GOX, MPO, and/or 4-aminobenzoic acid hydrazide (ABAH, a specific irreversible MPO inhibitor, Sigma). In addition, ABAH was injected intraperitoneally (i.p.) in some mice. Compound 3 or the nonspecific analogue, Compound 18, (2 nmol in 10 μL PBS) were injected intravenously 30 minutes later, and 25 μL SA-647 (2 mg/mL) was injected 60 minutes thereafter. Imaging using a dedicated FRI system (Olympus OV-110, Tokyo, Japan) was performed 30 minutes after injection of SA-647. AlexaFluor-647 bound to MPO-sensor was detected at 595-635 nm excitation and 675/50 nm emission. A linear increase in signal was detected with increasing concentrations of MPO, while no signal over background was detected with vehicle injection FIG. 7A, which demonstrates that our probe is sensitive to MPO activity.

On fluorescence reflectance imaging (FRI), increased fluorescent signal was detected with MPO and GOX, which was readily inhibited by the addition of ABAH as shown in FIG. 7B. With MPO but without GOX, no fluorescence was detectible, showing that the Compound 3 was not activated by $H_2O_2$ alone as shown in FIG. 7B. Absence of both MPO and GOX also resulted in no appreciable fluorescence as shown in FIG. 7B. Systemic (intraperitoneal) injection of ABAH also resulted in abrogation of fluorescence signal consistent with successful MPO inhibition as shown in FIG. 7B. Lastly, the nonspecific analogue containing tyrosine instead of 5-HT moieties was insensitive to both GOX and MPO as shown in FIG. 7B. These results show specificity of Compound 3 towards MPO.

Example 10

Irritant Contact Dermatitis

Female C57Bl/6J (wildtype, Jackson laboratories, Bar Harbor, Me.) and MPO-knockout (KO, Jackson laboratories) mice were treated topically with 0.08 μmol Phorbol 12-myristate 13-acetate (PMA, Sigma, St. Louis, Mo.) on one hind-paw and with vehicle on the other to induce irritant contact dermatitis. This model is well described in the literature and triggers rapid inflammation with influx of neutrophils into the skin. 6 hours after induction, mice were injected intravenously with either 2 nmol of Compound 3 or the non-specific analogue, Compound 18. 1 hour later, 2.5 μg SA-647 was injected intravenously to bind to the biotinylated Compound 3. Mice underwent in vivo imaging using a dedicated in vivo FRI system as described above in Example 11.

Applying these findings to mouse models of disease, the specificity of the probe was investigated in irritant contact dermatitis. When wildtype mice were treated topically with PMA to induce irritant contact dermatitis, increased fluorescence signal on the PMA-treated hind-paw but not the vehicle-treated hind-paw was seen FIG. 8A. In MPO-knockout mice treated with PMA and injected with Compound 3, no fluorescence over background was detected, as shown in FIG. 8B. Similarly, injection of the non-specific analogue into PMA-treated wildtype mice did not result in fluorescence over background, as shown in FIG. 8C. Quantification of fluorescence confirmed these findings, as fluorescence intensity was 130.5±4.7 for PMA compared to 34.4±8.6 for vehicle ($p<0.01$) in wildtype mice injected with Compound 3, 36.9±9.8 for PMA compared to 43.9±10.8 for vehicle ($p>0.05$) in MPO-KO mice injected with Compound 3, and 50.1±5.8 for PMA compared to 28.4±5.5 for vehicle ($P>0.05$) in wildtype mice injected with non-specific control sensor, as shown in FIG. 8D.

Example 11

Brain Abscess

Female C57Bl/6J mice were then anesthetized and fixed in a stereotactic head frame (David Kopf Instruments, Tujunga, Calif.). 1-3×$10^6$ colony forming units (CFU) salmonella bacteria (ATCC #14028) were suspended in 2 μL PBS and slowly injected into the deep frontal white matter (2.0 mm lateral and 1.2 mm anterior to bregma) at a depth of 3.0 mm. 23 hours later, mice were injected intravenously with 2 nmol Compound 3 as above, followed by intravenous injection of SA-647. Mice were then anesthetized with Isoflurane and transcardially perfused with 20 mL of ice cold PBS. Brains were harvested and cut into 1 mm coronal slices using a brain slicer (Harvard Apparatus, Holliston, Mass.) and immediately underwent FRI as described above. Brains from mice injected with salmonella were also embedded in OCT (Sakura, Torrance, Calif.) and snap-frozen in chilled isopentane (Sigma) and stored at 80° C. until sectioning. Serial 6 μm sections were cut on a cryostat (Thermo scientific). Sections were thawed at room temperature for 10-20 minutes and rehydrated in PBS for 10 minutes. Then sections were incubated in blocking buffer (1% horse serum in PBS) for 30 minutes at room temperature, and incubated with MPO specific probe diluted in incubation buffer (1% bovine serum albumin 1% normal donkey serum, 0.3% Triton X-100, and 0.01% sodium azide in PBS) overnight at 4° C. At the same time, adjacent sections were incubated with fluorescent anti-MPO antibody diluted in incubation buffer. Sections were washed in wash buffer 3 times and then incubated with SA-AF-647 antibody, and then washed in wash buffer 3 times. After that, sections were counterstained with DAPI (4',6-diamidino-2-phenylindole, Invitrogen) and mounted with anti-fade mounting medium. Images were captured with a digital camera (Nikon DXSM 1200-F, Nikon Inc., NY).

Next, CNS abscesses were induced in the frontal lobes of wildtype mice by intracerebral injection of salmonella, as shown in FIG. 9A, followed by injection of Compound 3 and AF-647 at 23 hours. Ex vivo FRI of coronal brain slices resulted in increased fluorescence signal consistent with MPO activity in the ipsilateral hemisphere but not the contralateral hemisphere. Contrary, injection of saline instead of bacteria did not result in significantly elevated MPO signal, as shown in FIG. 9B. Quantification of fluorescence intensity confirmed these findings, as signal was 43242 (mean value) in the ipsilateral hemisphere, and 10972 ((mean value) in the contralateral hemisphere, as shown in FIG. 9B.

When adding the Compound 3 followed by SA-647 to fresh-frozen ex vivo sections from abscess and control areas, increased fluorescent signal consistent with MPO activity in the ipsilateral hemisphere but not the contralateral hemisphere was detected. Adjacent sections incubated with an anti-MPO antibody to stain MPO protein demonstrated signal in both ipsilateral and contralateral hemisphere. In the contralateral control area, cells that stained positively for MPO protein but no appreciable MPO activity were detected, as shown in FIG. 9C. In addition, areas with MPO activity often demonstrated relatively less MPO protein.

Example 12

Imaging of Neutrophil Extracellular Traps

Female C57Bl/6J mice were injected subcutaneously at the dorsal aspect of the thigh with $10^8$ CFU of *Streptococcus pneumonia* (SPn, ATCC #6303) to induce bacterial cellulitis.

6 hours after induction, mice were injected intravenously with 2 nmol of MPO. 1 hour later, 2.5 μg Strepavidin-AlexaFluor-647 were injected intravenously to bind to the biotinylated Compound 3. To distinguish neutrophil granule release (where MPO and other granule proteins are secreted into the phagosome or extracellular space) from NET formation (where chromatin strands with MPO are released by neutrophils), 1 μg of the membrane-impermeable DNA dye Sytox Green (Invitrogen) was injected intravenously at the same time. Mice then underwent in vivo imaging using a dedicated FRI system as described above in Example 11. AlexaFluor-647 bound to MPO-sensor was detected at 595-635 nm excitation and 675/50 nm emission. Sytox Green was detected at 460-490 nm excitation and 530/40 nm emission.

Next, NET formation was imaged in vivo in a mouse model of bacterial cellulitis by injecting mice with *Streptococcus pneumonia* (SPn) and imaging both MPO with Compound 3 and extracellular DNA with Sytox Green. Increased fluorescence signal of both Compound 3 and Sytox Green was detected in thighs injected with SPn, but not in the contralateral thigh injected with PBS only, as shown in FIG. 10A-10B. Areas positive for MPO activity corresponded to areas of extracellular DNA (Sytox Green), suggesting the presence of NETs at the site of SPn induced bacterial cellulitis. Fluorescence quantification showed increased signal on the side injected with SPn (212.5±22.9 RFU), but not on the side injected with PBS as shown in FIG. 10A-B (49.4±15.5 RFUs, $p<0.01$).

NETs have only recently been described, and increasing evidence points to involvement in not only infection, but also thrombosis and autoimmunity, Hitherto, research on NETs outside of in vitro systems is conducted by either post-mortem histological assessment or fluorescence microscopy. By co-injection of Compound 3 with Sytox Green, sites of MPO activity and extracellular DNA, two defining molecular components of NETs, were imaged (35). Without being bound by theory, colocalization of these two markers suggests NET formation in vivo.

Compound 3 allowed for detection of dermatitis, CNS abscess, and cellulitis with a CNR of approximately 4. This is much higher than a previously reported fluorescent MPO probe (SNAPF), where CNRs of around 1.4 and 1.6 were found in vitro and in vivo, respectively. Furthermore, the CNR for SNAPF in vivo was calculated by utilizing transgenic mice with overexpression of human MPO. Since human MPO is approximately 10 times more active than murine MPO, it is expected that CNR would be even higher in humans using the MPO probe described herein (i.e., Compound 3). To investigate specificity, MPO knockout mice were utilized and wildtype mice were injected with a non-specific control probe. In both instances, signals above background were not detected, showing specificity of the probe system.

Example 13

In Vitro Color Change

Conditions

Each vial contains 2 mM of $^{19}F$ compound 9 in PBS (150 uL, 5% DMSO) and the following agents, and was incubated at 37° C. for 1 hr:

Vial 1: control (2 mM 19F Compound 8 only)

Vial 2: Glucose (6 μL, 1M), GOX (4 μL, 1 mg/mL);

Vial 3: $H_2O_2$ (2 μL), HRP (horseradish peroxidase, 1 μL);

Vial 4: $H_2O_2$(2 μL), MPO (10 μL):

Vial 5: $H_2O_2$ (2 μL), MPO (10 μL);

Comparing to vial 1, vial 2 had no color change in the absence of MPO. Vial 3, 4 and 5 turned to yellow or brown over time since the oligomerization of the 19F compound in the presence of MPO and $H_2O_2$, as shown in FIG. 11.

Example 16

Blood Brain Barrier Assay

Female C57Bl/6J mice were injected intravenously with either 3'-deoxy-3'-$^{18}F$-fluorothymidine (FLT) or Compound 9 (300-600 μCi). The mice were imaged 2 hours after the PET tracers were injected. As shown in FIG. 12, Compound 9 showed higher uptake in the brain compared to FLT, a compound that is unable to cross the blood brain barrier (BBB), demonstrating that Compound 9 can cross intact BBB and may be a useful imaging agent for repotting neurological diseases.

Example 17

(S)-6-(dimethylamino)-N-(2-(2-(2-fluoroethoxy)ethoxy)ethyl)-2-((S)-3-(5-hydroxy-1H-indol-3-yl)-2-(2-(5-hydroxy-1H-indol-3-yl)acetamido)propanamido)hexanamide

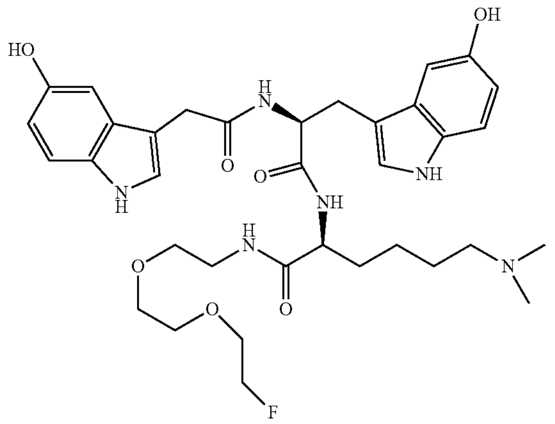 [SMILES: CN(C)CCCC[C@H](NC(=O)[C@H](Cc1c[nH]c2ccc(O)cc12)NC(=O)Cc1c[nH]c2ccc(O)cc12)C(=O)NCCOCCOCCF]

The compound of Example 17 was prepared according to procedures similar to the synthesis of Compound 8 (see e.g., Example 1 and Scheme 3). In brief, N-Boc-N-dimethyl-L-lysine was coupled with Intermediate 2f using (3-dimethylaminopropyl)-N'-ethylcarbodiimide hydrochloride (EDC.HCl) and N-hydroxysuccinimide (NHS) as coupling agents. The subsequent de-protection of the Boc group by 10% trifluoroacetic acid afforded (S)-2-amino-6-(dimethylamino)-N-(2-(2-(2-fluoroethoxy)ethoxy)ethyl)-hexanamide, which was then coupled with Intermediate 1 to give the title compound. $^1H$ NMR (500 MHz, DMSO) δ 12.52 (broad, 1H), 10.46 (s, 1H), 10.42 (s, 1H), 9.25 (broad, 1H), 8.54 (m, 2H), 7.96 (m, 2H), 7.61 (dd, 1H), 7.05 (d, 1H), 7.03 (d, 1H), 6.94 (m, 2H), 6.75 (m, 2H), 6.51 (m, 2H), 4.48 (m, 2H), 4.36 (m, 2H), 3.33-3.58 (m, 6H), 2.79-3.10 (m, 4H), 2.57-2.66 (m, 4H), 2.47 (s, 6H), 1.40-1.47 (m, 4H), 1.10 (m, 2H); $^{13}C$ NMR (500 MHz, DMSO) δ 174.0, 171.9, 171.2, 150.7, 150.6, 131.0, 128.5, 128.4, 128.3, 124.6 (2), 112.2, 112.0, 111.7, 109.3, 109.2, 108.2, 103.0, 102.6, 84.3, 82.7, 70.2, 70.0, 69.3, 56.9, 53.9, 53.2, 52.6, 42.5, 38.9, 32.7, 31.7, 28.1, 23.7, 22.5. LCMS found m/z 683.5 (M+1).

Example 18

(S)-6-(dimethylamino)-N-(2-(2-(2-fluoro-$^{18}$F) ethoxy)ethoxy)ethyl)-2-((S)-3-(5-hydroxy-1H-indol-3-yl)-2-(2-(5-hydroxy-1H-indol-3-yl)acetamido) propanamido)hexanamide hydrochloric acid salt

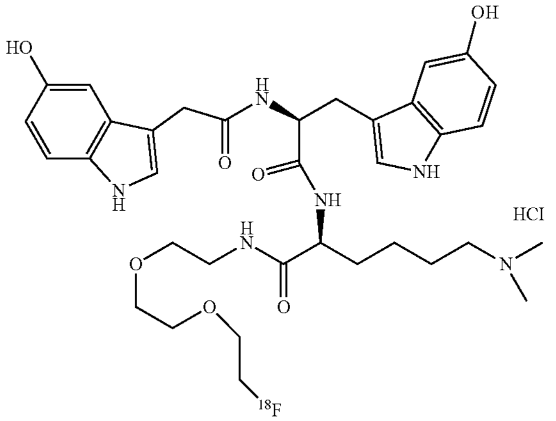

[18F]-Radiolabeling was performed according to the procedures described in Example 7, beginning with the Boc-protected precursor of Example 17. The Boc de-protection was performed with 1M HCl to afford the final compound, which exhibited increased solubility.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of imaging a cell or tissue sample, the method comprising:

i) administering to the subject a compound of Formula I

I

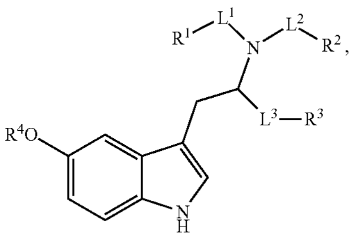

or a pharmaceutically acceptable salt thereof, wherein:

$L^1$ is selected from the group consisting of a bond, —C(O)—, —C(O)O—, —C(O) NR$^{a1}$—, —C(O)($C_{1-6}$ alkylene)-, and —C(O)($C_{1-6}$ alkyleneoxy)-;

$R^1$ is selected from the group consisting of H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, —C(O)O—, —C(O) NR$^{a2}$—, —C(O)($C_{1-6}$ alkylene)-, and —C(O)($C_{1-6}$ alkyleneoxy)-;

$R^2$ is selected from the group consisting of $C_{1-6}$ alkoxy, $C_{3-10}$ cycloalkyl, $C_{6-10}$ aryl, 4-10 membered heterocycloalkyl, and 5-9 membered heteroaryl, wherein each $C_{1-6}$ alkoxy, $C_{3-10}$ cycloalkyl, $C_{6-10}$ aryl, 4-10 membered heterocycloalkyl, and 5-9 membered heteroaryl is optionally substituted by 1, 2, 3, or 4 substituents independently selected from OH, halo, $C_{1-6}$ alkoxy, and $C_{1-6}$ haloalkyl;

$L^3$ is selected from the group consisting of a bond, —C(O)—, —C(O)O—, —C(O)($C_{1-6}$ alkylene)-, —C(O)($C_{1-6}$ alkyleneoxy)-, —C(O)N(R$^{a3}$) ($C_{1-6}$ alkylene)-, —C(O)N(R$^{a3}$) ($C_{1-6}$ alkylene)-di($C_{1-6}$ alkyl) amino, and —C(O)N(R$^{a3}$) ($C_{1-6}$ alkyleneoxy)-;

$R^3$ is selected from the group consisting of $C_{1-6}$ haloalkyl, $C_{3-10}$ cycloalkyl, $C_{6-10}$ aryl, 4-10 membered heterocycloalkyl, 5-10 membered heteroaryl, and —C(O)N (R$^{a3}$) ($C_{1-6}$ haloalkoxy), wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$R^4$ is H; and each R$^{a1}$, R$^{a2}$, and R$^{a3}$ is independently selected from the group consisting of H, $C_{1-6}$ alkyl, $C_{2-6}$ alkenyl, $C_{2-6}$ alkynyl, and $C_{1-6}$ haloalkyl;

ii) waiting a time sufficient to allow the compound to accumulate at a cell or tissue site associated with the disease; and iii) imaging the cell or tissue with an imaging technique.

2. The method of claim 1, wherein the method is an in vivo method.

3. The method of claim 1, wherein the sufficient time is from about 5 minutes to about 6 hours.

4. The method of claim 1, wherein the imaging technique is selected from fluorescence imaging and positron emission tomography.

5. The method of claim 1, wherein the cell or tissue is brain cell or tissue.

6. The method of claim 1, wherein:

$L^1$ is selected from the group consisting of a bond, —C(O)—, —C(O)($C_{1-6}$ alkylene)-, and —C(O)($C_{1-6}$ alkyleneoxy)-;

$R^1$ is selected from the group consisting of H, $C_{3-10}$ cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-9 membered heteroaryl, wherein each $C_{1-6}$ alkoxy, $C_{6-10}$ aryl, 4-10 membered heterocycloalkyl, and 5-9 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl.

7. The method of claim 1, wherein:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by 1, 2, 3, or 4 substituents independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-9 membered heteroaryl, wherein each $C_{1-6}$ alkoxy, $C_{6-10}$ aryl, 4-10 membered heterocycloalkyl, and 5-9 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl, and 5-10 membered heteroaryl, wherein each $C_{1-6}$ haloalkyl, and 5-10 membered heteroaryl is optionally substituted by 1, 2, 3, or 4 substituents independently selected from OH, halo, and $C_{1-6}$ haloalkyl.

8. The method of claim 1, wherein:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by one substituent independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-9 membered heteroaryl, wherein each $C_{1-6}$ alkoxy, $C_{6-10}$ aryl, 4-10 membered heterocycloalkyl, and 5-9 membered heteroaryl is optionally substituted by one substituent independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl and 5-10 membered heteroaryl, wherein each $C_{1-6}$ haloalkyl and 5-10 membered heteroaryl is optionally substituted by one substituent independently selected from OH, halo, and $C_{1-6}$ haloalkyl.

9. The method of claim 1, wherein the compound of Formula I is selected from any one of the following compounds, of a pharmaceutically acceptable salt thereof:

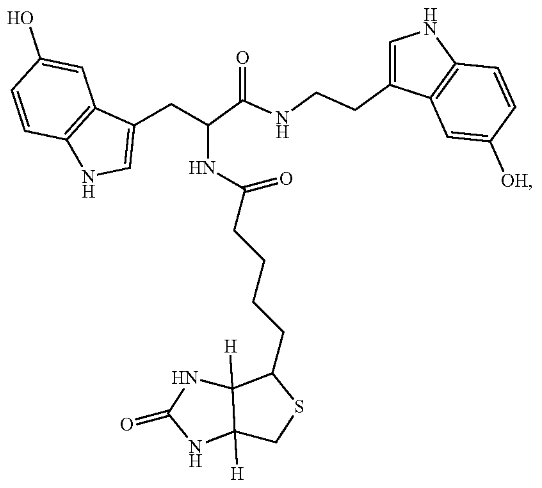

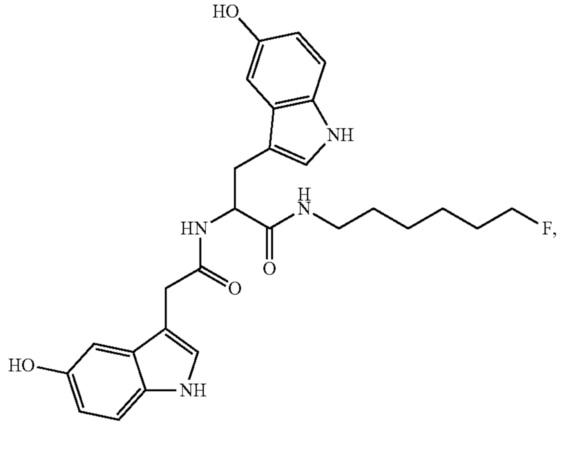

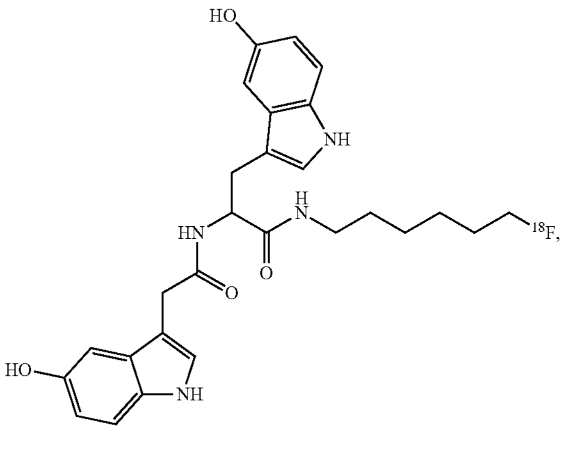

-continued
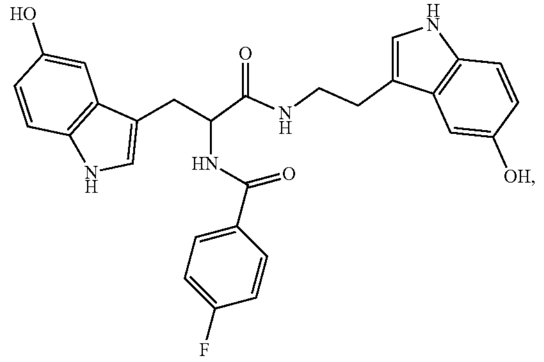
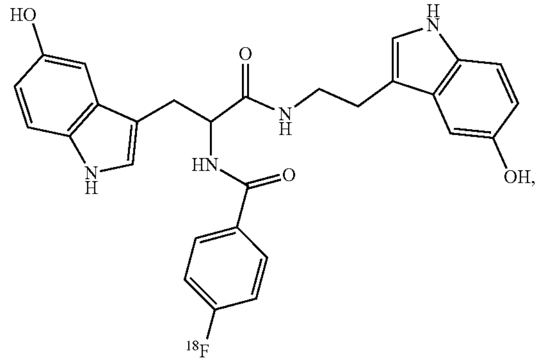
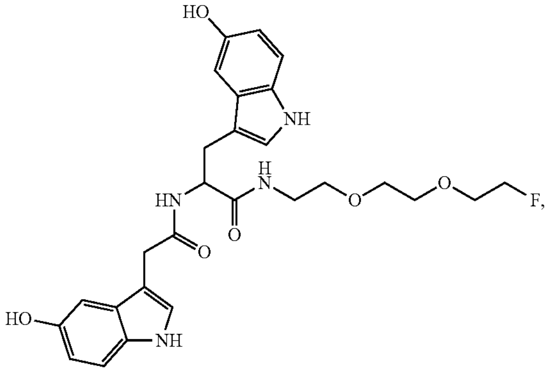
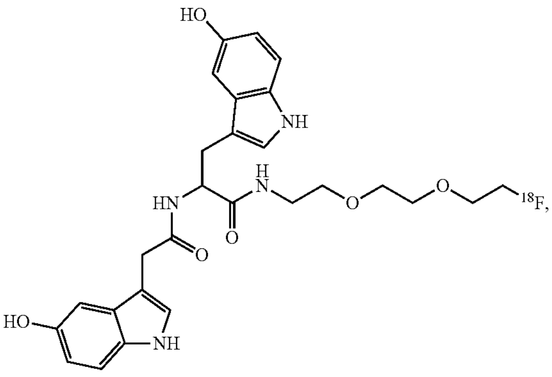
-continued
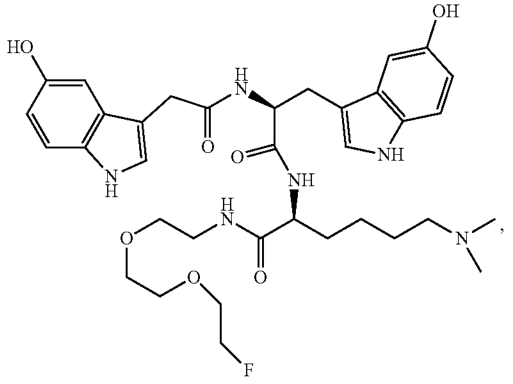
or
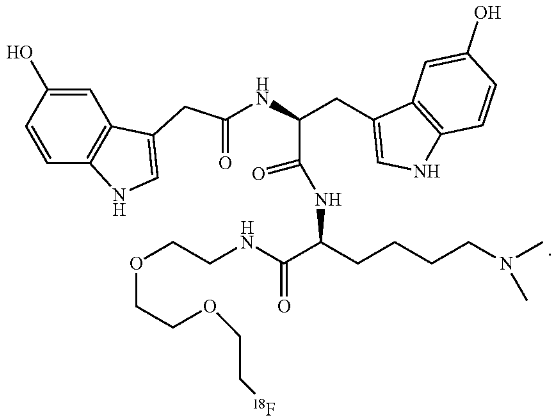
10. The method of claim 1, wherein the compound has formula:
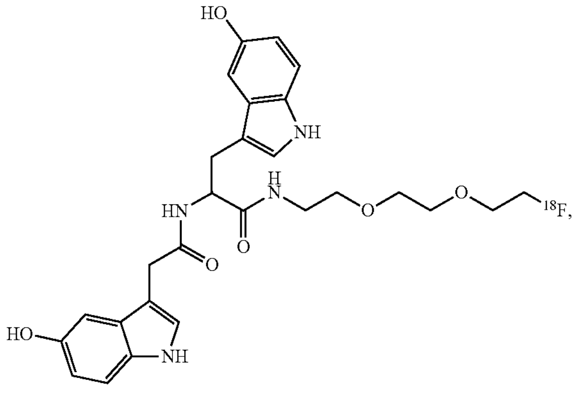 [SMILES: O=C(Cc1c[nH]c2ccc(O)cc12)NC(Cc1c[nH]c2ccc(O)cc12)C(=O)NCCOCCOCC[18F]]
or a pharmaceutically acceptable salt thereof.
11. A method of diagnosing a disease or disorder associated with abnormal myeloperoxidase activity in a subject, comprising:

i) administering to the subject a compound of Formula I:

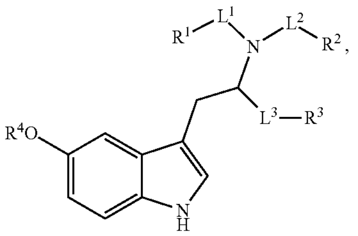

I or a pharmaceutically acceptable salt thereof, wherein:

$L^1$ is selected from the group consisting of a bond, —C(O)—, —C(O)O—, —C(O) $NR^{a1}$—, —C(O)($C_{1-6}$ alkylene)-, and —C(O)($C_{1-6}$ alkyleneoxy)-;

$R^1$ is selected from the group consisting of H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, —C(O)O—, —C(O) $NR^{a2}$—, —C(O)($C_{1-6}$ alkylene)-, and —C(O)($C_{1-6}$ alkyleneoxy)-;

$R^2$ is selected from the group consisting of $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkoxy, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^3$ is selected from the group consisting of a bond, —C(O)—, —C(O)O—, —C(O)($C_{1-6}$ alkylene)-, —C(O)($C_{1-6}$ alkyleneoxy)-, —C(O)N($R^{a3}$) ($C_{1-6}$ alkylene)-, —C(O)N($R^{a3}$) ($C_{1-6}$ alkylene)-di($C_{1-6}$ alkyl) amino, and —C(O)N($R^{a3}$) ($C_{1-6}$ alkyleneoxy)-;

$R^3$ is selected from the group consisting of $C_{1-6}$ haloalkyl, $C_{3-10}$ cycloalkyl, $C_{6-10}$ aryl, 4-10 membered heterocycloalkyl, 5-10 membered heteroaryl, and —C(O)N ($R^{a3}$) ($C_{1-6}$ haloalkoxy), wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$R^4$ is H; and each $R^{a1}$, $R^{a2}$, and $R^{a3}$ is independently selected from the group consisting of H, $C_{1-6}$ alkyl, $C_{2-6}$ alkenyl, $C_{2-6}$ alkynyl, and $C_{1-6}$ haloalkyl;

ii) waiting a time sufficient to allow the compound to accumulate at a cell or tissue site associated with the disease; and iii) imaging the cell or tissue with an imaging technique.

12. The method of claim 11, wherein the disease or disorder associated with abnormal myeloperoxidase activity is selected from a cancer, a rheumatic disease, an infectious disease, a disease of the central nervous system, a cardiovascular disorder, an autoimmune disorder, and inflammation associated with one or more of a cancer, a rheumatic disease, an infectious disease, disease of the central nervous system, cardiovascular disorder, and autoimmune disorder.

13. The method of claim 12, wherein:

the disease of the central nervous system is selected from the group consisting of Alzheimer's disease, stroke, epilepsy, Parkinson's disease, and inflammation associated with one or more of Alzheimer's disease, stroke, epilepsy, and Parkinson's disease;

the cardiovascular disorder is selected from atherosclerosis, myocardial infarction, atrial fibrillation, vasculitis, and inflammation associated with one or more of atherosclerosis, myocardial infarction, atrial fibrillation, and vasculitis;

the autoimmune disorder is selected from the group consisting of multiple sclerosis, meningitis, encephalitis, and inflammation associated with one or more of multiple sclerosis, meningitis, and encephalitis;

the cancer is selected from bladder cancer, breast cancer, carcinoma, cervical cancer, colorectal cancer, endometrial cancer, glioma, cancer of the head and neck, liver cancer, lung cancer, melanoma, ovarian cancer, pancreatic cancer, prostate cancer, renal cancer, skin cancer, stomach cancer, testicular cancer, leukemia, and thyroid cancer;

the rheumatic disease is selected from rheumatoid arthritis, osteoarthritis, and inflammatory arthritis; and the infectious disease is selected from a fungal disease and a bacterial disease.

14. The method of claim 11, wherein the sufficient time is from about 5 minutes to about 6 hours.

15. The method of claim 11, wherein the imaging technique is selected from fluorescence imaging and positron emission tomography.

16. The method of claim 11, wherein:

$L^1$ is selected from the group consisting of a bond, —C(O)—, —C(O)($C_{1-6}$ alkylene)-, and —C(O)($C_{1-6}$ alkyleneoxy)-;

$R^1$ is selected from the group consisting of H, $C_{3-10}$ cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl.

17. The method of claim 11, wherein:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by 1, 2, 3, or 4 substituents independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl, and 5-10 membered heteroaryl, wherein each $C_{1-6}$ haloalkyl, and 5-10 membered heteroaryl is optionally substituted by 1, 2, 3, or 4 substituents independently selected from OH, halo, and $C_{1-6}$ haloalkyl.

18. The method of claim 11, wherein:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by one substituent independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by one substituent independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl and 5-10 membered heteroaryl, wherein each $C_{1-6}$ haloalkyl and 5-10 membered heteroaryl is optionally substituted by one substituent independently selected from OH, halo, and $C_{1-6}$ haloalkyl.

19. The method of claim 11, wherein the compound of Formula I is selected from any one of the following compounds, of a pharmaceutically acceptable salt thereof:

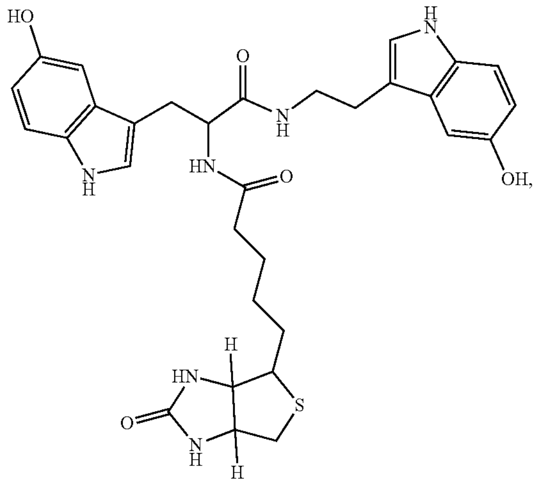

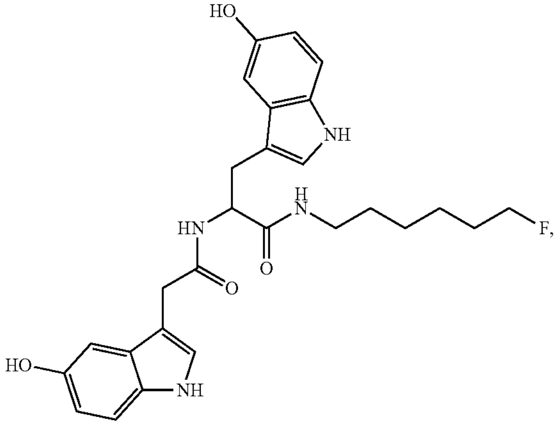

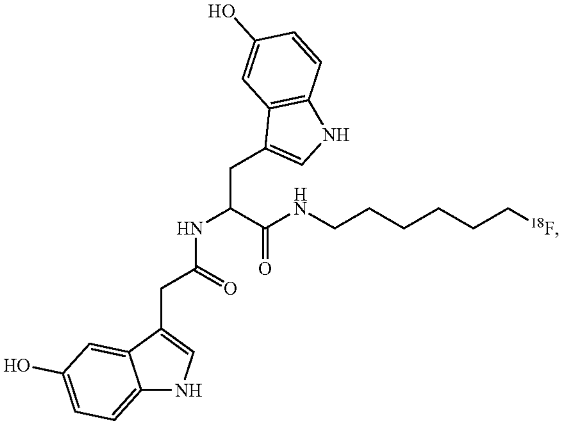

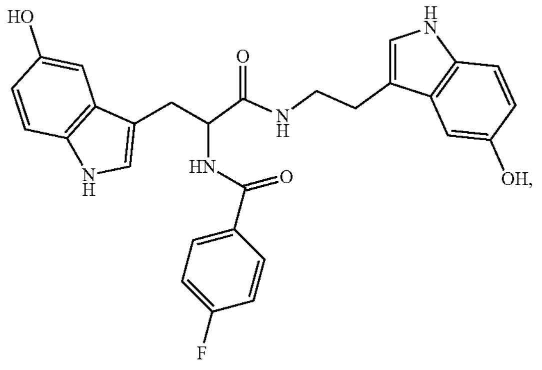

-continued

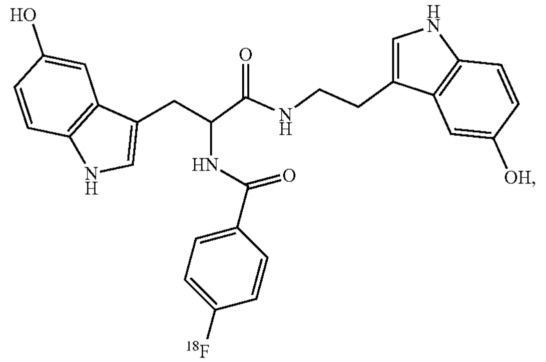

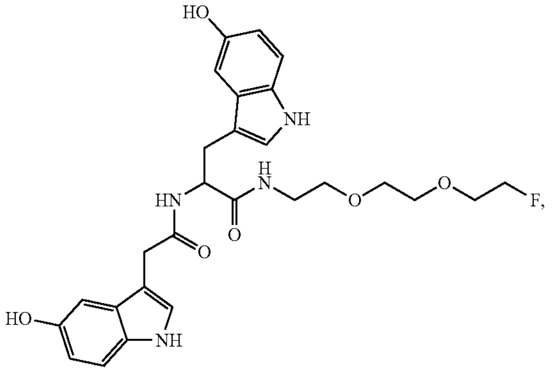

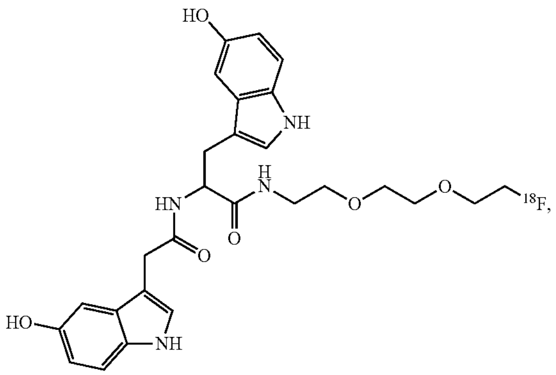

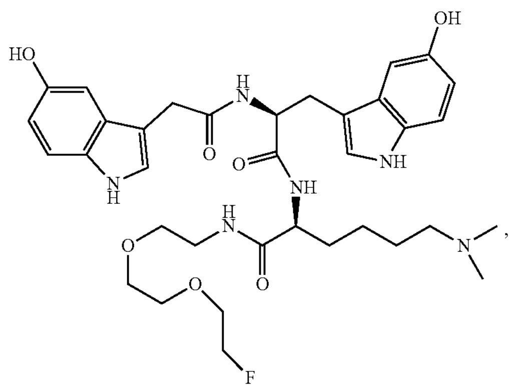

or

-continued

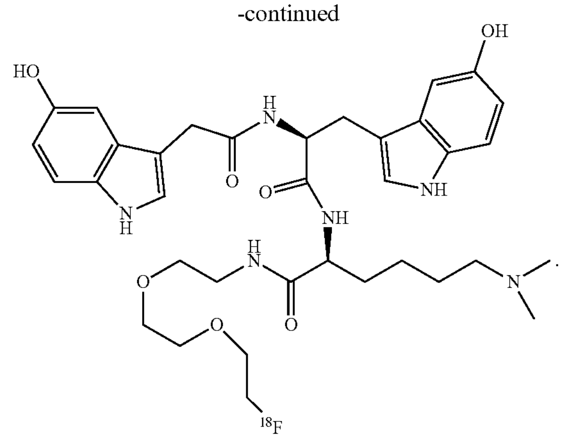

20. The method of claim 11, wherein the compound has formula:

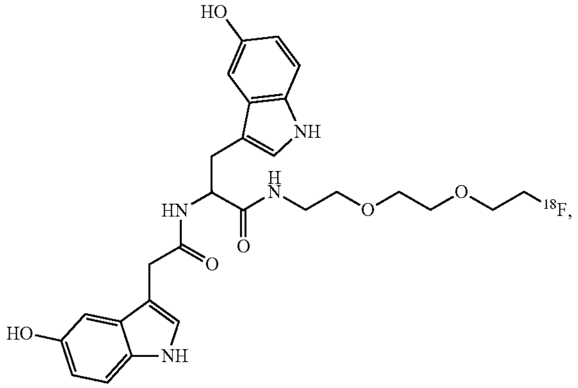 [SMILES: O=C(Cc1c[nH]c2ccc(O)cc12)NC(Cc1c[nH]c2ccc(O)cc12)C(=O)NCCOCCOCC[18F]]

or a pharmaceutically acceptable salt thereof.

21. A method of detecting myeloperoxidase activity in a subject, the method comprising:

i) administering to the subject a compound of Formula I:

I

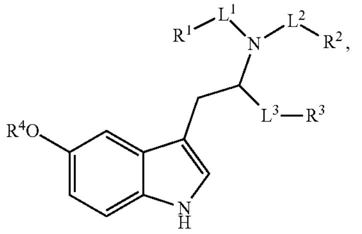

or a pharmaceutically acceptable salt thereof, wherein:

$L^1$ is selected from the group consisting of a bond, —C(O)—, —C(O)O—, —C(O) $NR^{a1}$—, —C(O)($C_{1-6}$ alkylene)-, and —C(O)($C_{1-6}$ alkyleneoxy)-;

$R^1$ is selected from the group consisting of H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, —C(O)O—, —C(O)NR$^{a2}$—, —C(O)($C_{1-6}$ alkylene)-, and —C(O)($C_{1-6}$ alkyleneoxy)-;

$R^2$ is selected from the group consisting of $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkoxy, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^3$ is selected from the group consisting of a bond, —C(O)—, —C(O)O—, —C(O)($C_{1-6}$ alkylene)-, —C(O)($C_{1-6}$ alkyleneoxy)-, —C(O)N($R^{a3}$) ($C_{1-6}$ alkylene)-, —C(O)N($R^{a3}$) ($C_{1-6}$ alkylene)-di($C_{1-6}$ alkyl) amino, and —C(O)N($R^{a3}$) ($C_{1-6}$ alkyleneoxy)-;

$R^3$ is selected from the group consisting of $C_{1-6}$ haloalkyl, $C_{3-10}$ cycloalkyl, $C_{6-10}$ aryl, 4-10 membered heterocycloalkyl, 5-10 membered heteroaryl, and —C(O)N($R^{a3}$) ($C_{1-6}$ haloalkoxy), wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$R^4$ is H; and each $R^{a1}$, $R^{a2}$, and $R^{a3}$ is independently selected from the group consisting of H, $C_{1-6}$ alkyl, $C_{2-6}$ alkenyl, $C_{2-6}$ alkynyl, and $C_{1-6}$ haloalkyl;

ii) imaging the subject with an imaging technique.

22. The method of claim 21, wherein the imaging technique is selected from fluorescence imaging and positron emission tomography.

23. The method of claim 21, wherein:

$L^1$ is selected from the group consisting of a bond, —C(O)—, —C(O)($C_{1-6}$ alkylene)-, and —C(O)($C_{1-6}$ alkyleneoxy)-;

$R^1$ is selected from the group consisting of H, $C_{3-10}$ cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl.

24. The method of claim 21, wherein:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by 1, 2, 3, or 4 substituents independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl, and 5-10 membered heteroaryl, wherein each $C_{1-6}$ haloalkyl, and 5-10 membered heteroaryl is optionally substituted by 1, 2, 3, or 4 substituents independently selected from OH, halo, and $C_{1-6}$ haloalkyl.

25. The method of claim 21, wherein:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by one substituent independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by one substituent independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl and 5-10 membered heteroaryl, wherein each $C_{1-6}$ haloalkyl and 5-10 membered heteroaryl is optionally substituted by one substituent independently selected from OH, halo, and $C_{1-6}$ haloalkyl.

26. The method of claim 21, wherein the compound of Formula I is selected from any one of the following compounds, of a pharmaceutically acceptable salt thereof:

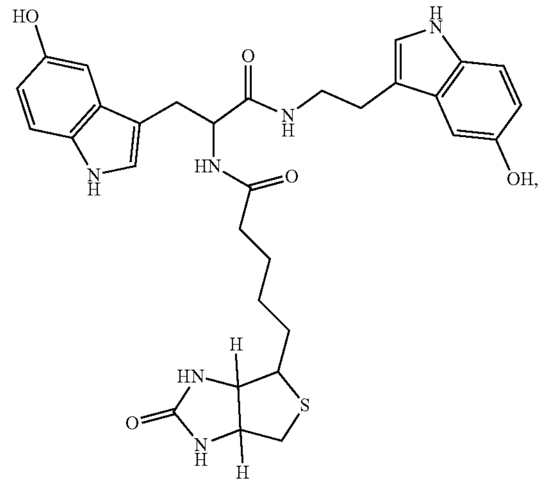
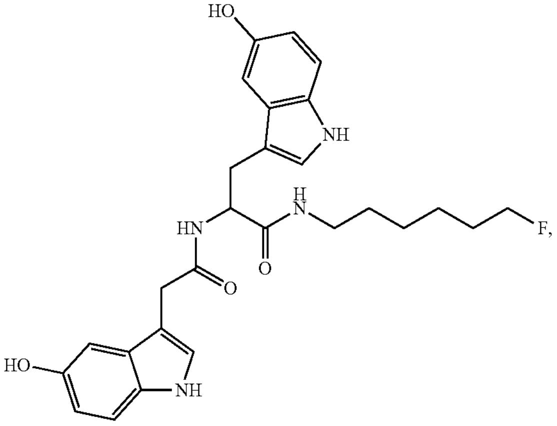
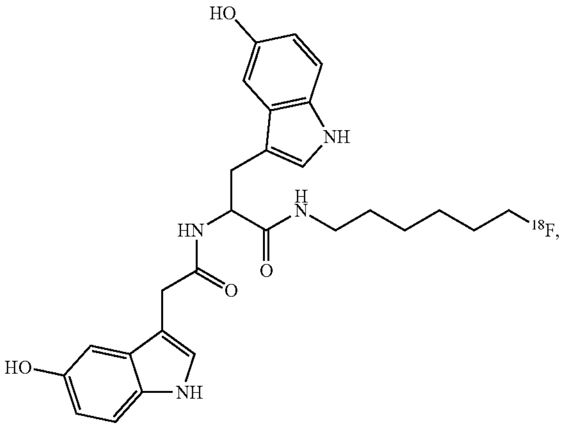
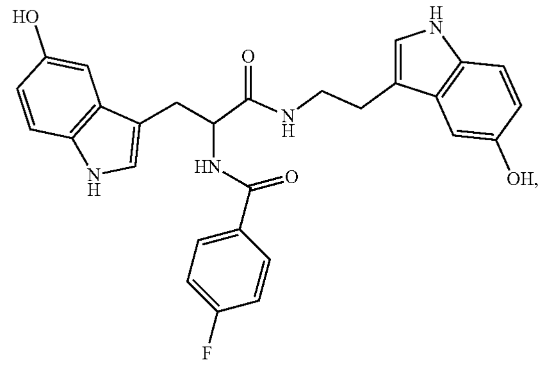
-continued
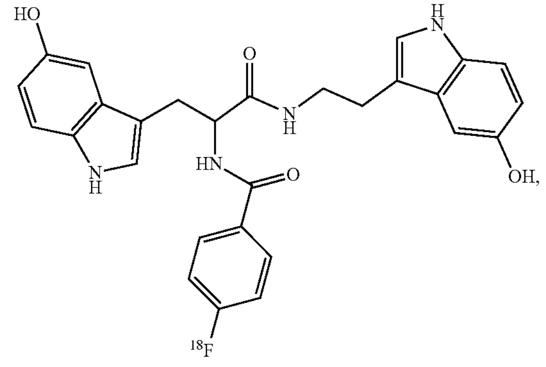
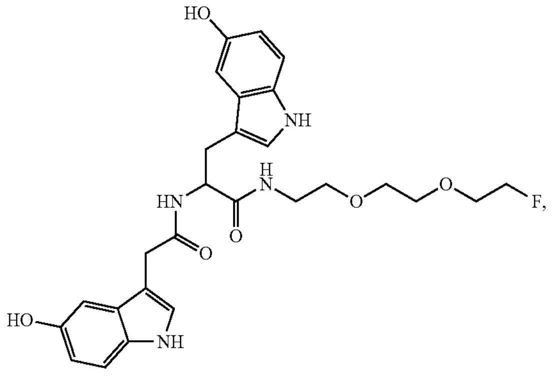
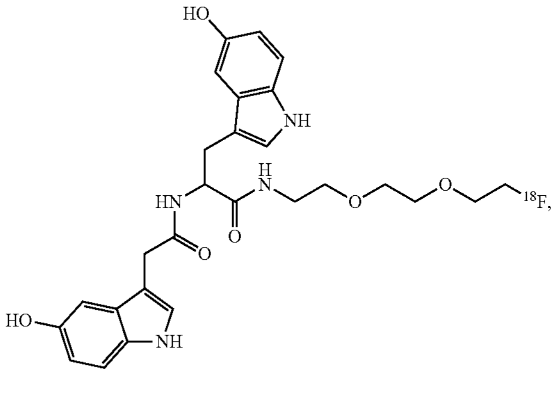
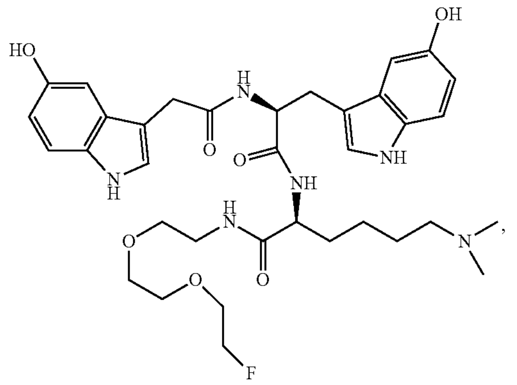
or -continued

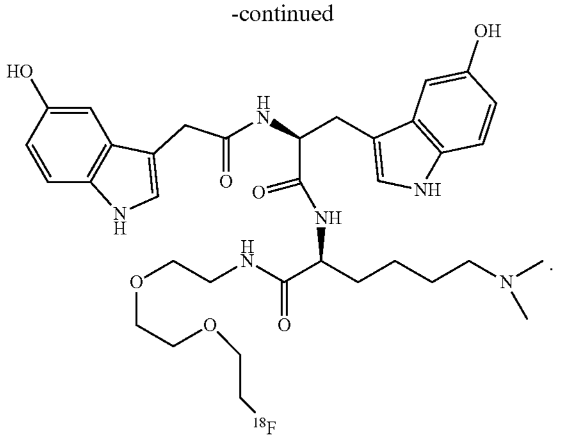

27. The method of claim 21, wherein the compound has formula:

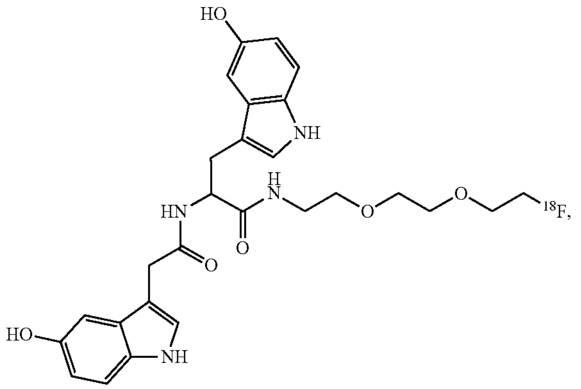 [SMILES: O=C(Cc1c[nH]c2ccc(O)cc12)NC(Cc1c[nH]c2ccc(O)cc12)C(=O)NCCOCCOCC[18F]]

or a pharmaceutically acceptable salt thereof.

28. A method of monitoring treatment of a disease or disorder associated with abnormal myeloperoxidase activity in a subject, the method comprising:

i) administering to the subject a compound of Formula I:

I

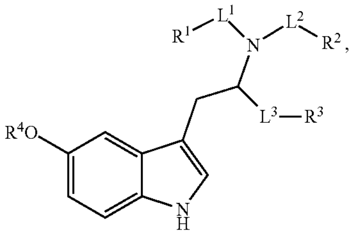

or a pharmaceutically acceptable salt thereof, wherein:

$L^1$ is selected from the group consisting of a bond, —C(O)—, —C(O)O—, —C(O) $NR^{a1}$—, —C(O)($C_{1-6}$ alkylene)-, and —C(O)($C_{1-6}$ alkyleneoxy)-;

$R^1$ is selected from the group consisting of H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, —C(O)O—, —C(O) $NR^{a2}$—, —C(O)($C_{1-6}$ alkylene)-, and —C(O)($C_{1-6}$ alkyleneoxy)-;

$R^2$ is selected from the group consisting of $C_{1-6}$ alkoxy, $C_{3-10}$ cycloalkyl, $C_{6-10}$ aryl, 4-10 membered heterocycloalkyl, and 5-10 membered heteroaryl, wherein each $C_{1-6}$ alkoxy, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, $C_{1-6}$ alkoxy, and $C_{1-6}$ haloalkyl;

$L^3$ is selected from the group consisting of a bond, —C(O)—, —C(O)O—, —C(O)($C_{1-6}$ alkylene)-, —C(O)($C_{1-6}$ alkyleneoxy)-, —C(O)N($R^{a3}$) ($C_{1-6}$ alkylene)-, —C(O)N($R^{a3}$) ($C_{1-6}$ alkylene)-di($C_{1-6}$ alkyl) amino, and —C(O)N($R^{a3}$) ($C_{1-6}$ alkyleneoxy)-;

$R^3$ is selected from the group consisting of $C_{1-6}$ haloalkyl, $C_{3-10}$ cycloalkyl, $C_{6-10}$ aryl, 4-10 membered heterocycloalkyl, 5-10 membered heteroaryl, and —C(O)N ($R^{a3}$) ($C_{1-6}$ haloalkoxy), wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$R^4$ is H; and each $R^{a1}$, $R^{a2}$, and $R^{a3}$ is independently selected from the group consisting of H, $C_{1-6}$ alkyl, $C_{2-6}$ alkenyl, $C_{2-6}$ alkynyl, and $C_{1-6}$ haloalkyl;

ii) imaging the subject with an imaging technique;

iii) administering to the subject a therapeutically effective amount of a therapeutic compound to treat the disease or disorder;

iv) imaging the cell or tissue in the subject with an imaging technique; and v) comparing the image of step i) and the image of step iv).

29. The method of claim 28, wherein the method further comprises administering to the subject the compound of Formula I, or a pharmaceutically acceptable salt thereof, after the administering of step iii) and prior to the imaging of step iv).

30. The method of claim 28, wherein the imaging technique is selected from fluorescence imaging and positron emission tomography.

31. The method of claim 28, wherein the disease or disorder associated with abnormal myeloperoxidase activity is selected from a cancer, a rheumatic disease, an infectious disease, a disease of the central nervous system, a cardiovascular disorder, an autoimmune disorder, and inflammation associated with one or more of a cancer, a rheumatic disease, an infectious disease, disease of the central nervous system, cardiovascular disorder, and autoimmune disorder.

32. The method of claim 31, wherein:

the disease of the central nervous system is selected from the group consisting of Alzheimer's disease, stroke, epilepsy, Parkinson's disease, and inflammation associated with one or more of Alzheimer's disease, stroke, epilepsy, and Parkinson's disease;

the cardiovascular disorder is selected from atherosclerosis, myocardial infarction, atrial fibrillation, vasculitis, and inflammation associated with one or more of atherosclerosis, myocardial infarction, atrial fibrillation, and vasculitis;

the autoimmune disorder is selected from the group consisting of multiple sclerosis, meningitis, encephalitis, and inflammation associated with one or more of multiple sclerosis, meningitis, and encephalitis;

the cancer is selected from bladder cancer, breast cancer, carcinoma, cervical cancer, colorectal cancer, endometrial cancer, glioma, cancer of the head and neck, liver cancer, lung cancer, melanoma, ovarian cancer, pancreatic cancer, prostate cancer, renal cancer, skin cancer, stomach cancer, testicular cancer, leukemia, and thyroid cancer;

the rheumatic disease is selected from rheumatoid arthritis, osteoarthritis, and inflammatory arthritis; and the infectious disease is selected from a fungal disease and a bacterial disease.

33. The method of claim 28, wherein:

$L^1$ is selected from the group consisting of a bond, —C(O)—, —C(O)($C_{1-6}$ alkylene)-, and —C(O)($C_{1-6}$ alkyleneoxy)-;

$R^1$ is selected from the group consisting of H, $C_{3-10}$ cycloalkyl, $C_{6-10}$ aryl, 4-10 membered heterocycloalkyl, and 5-10 membered heteroaryl, wherein each $C_{1-6}$ alkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^2$ is selected from the group consisting of —($C_{1-6}$ alkylene)-($C_{3-10}$ cycloalkylene)-, —($C_{1-6}$ alkylene)-($C_{6-10}$ arylene)-, —($C_{1-6}$ alkylene)-(4-10 membered heterocycloalkylene)-, —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl, $C_{3-10}$ cycloalkyl, $C_{6-10}$ aryl, 4-10 membered heterocycloalkyl, and 5-10 membered heteroaryl, wherein each $C_{1-6}$ haloalkyl, $C_{3-10}$ cycloalkyl, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl.

34. The method of claim 28, wherein:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by 1, 2, 3, or 4 substituents independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by 1, 2, 3, or 4 substituents independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl, and 5-10 membered heteroaryl, wherein each $C_{1-6}$ haloalkyl, and 5-10 membered heteroaryl is optionally substituted by 1, 2, 3, or 4 substituents independently selected from OH, halo, and $C_{1-6}$ haloalkyl.

35. The method of claim 28, wherein:

$L^1$ is selected from the group consisting of a bond and —C(O)($C_{1-6}$ alkylene)-;

$R^1$ is selected from the group consisting of H and 4-10 membered heterocycloalkyl, wherein the 4-10 membered heterocycloalkyl is optionally substituted by one substituent independently selected from OH, halo, and $C_{1-6}$ haloalkyl;

$L^2$ is selected from the group consisting of —($C_{1-6}$ alkylene)-(5-10 membered heteroarylene)-, —C(O)—, and —C(O)($C_{1-6}$ alkylene)-;

$R^2$ is selected from the group consisting of $C_{1-6}$ alkoxy, $C_{6-10}$ aryl, 4-10 membered heterocycloalkyl, and 5-10 membered heteroaryl, wherein each $C_{1-6}$ alkoxy, $C_{6-10}$ aryl, 4-10 membered heterocycloalkyl, and 5-10 membered heteroaryl is optionally substituted by one substituent independently selected from OH, halo, and $C_{1-6}$ haloalkyl;

$L^3$ is selected from the group consisting of a bond, —C(O)N($R^{a3}$) ($C_{1-6}$ alkylene)-, and —C(O)N($R^{a3}$) ($C_{1-6}$ alkyleneoxy)-; and $R^3$ is selected from the group consisting of $C_{1-6}$ haloalkyl and 5-10 membered heteroaryl, wherein each $C_{1-6}$ haloalkyl and 5-10 membered heteroaryl is optionally substituted by one substituent independently selected from OH, halo, and $C_{1-6}$ haloalkyl.

36. The method of claim 28, wherein the compound of Formula I is selected from any one of the following compounds, of a pharmaceutically acceptable salt thereof:

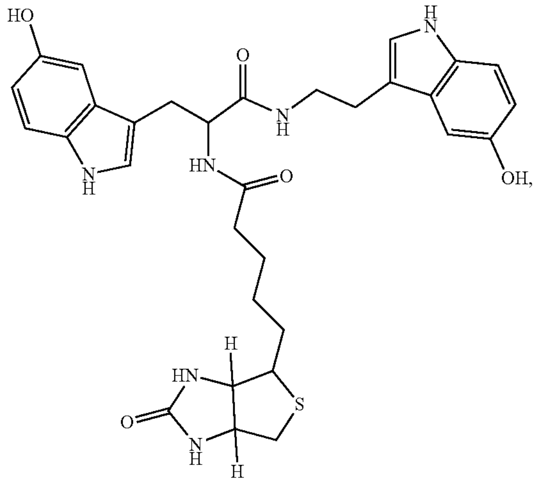

-continued
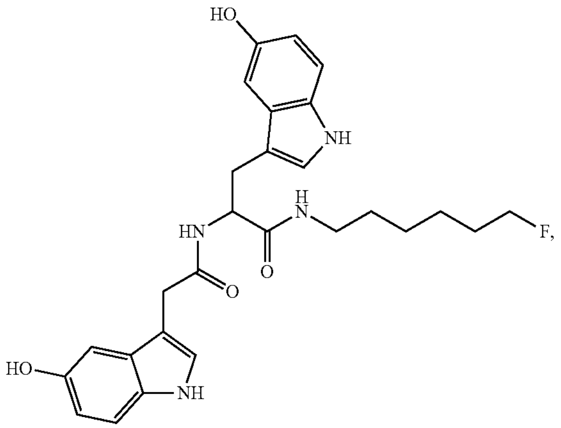
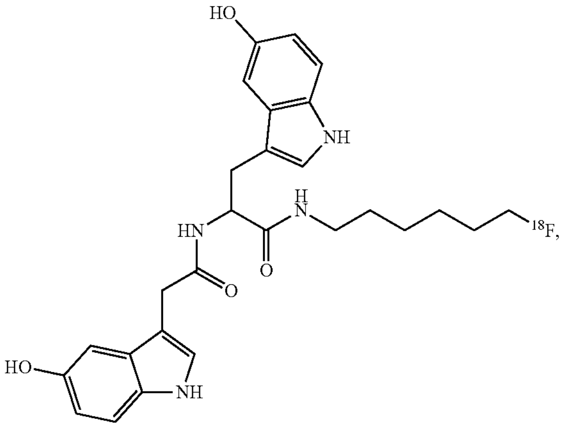
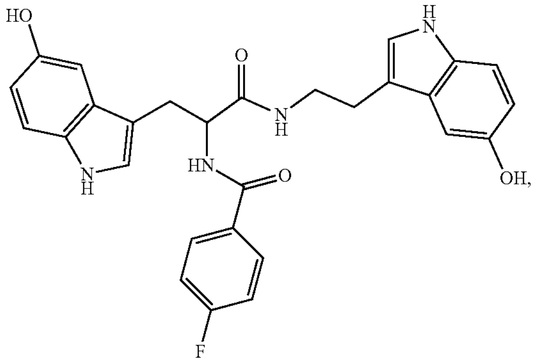
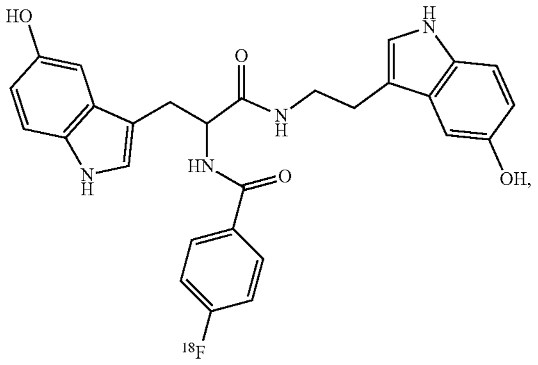
-continued
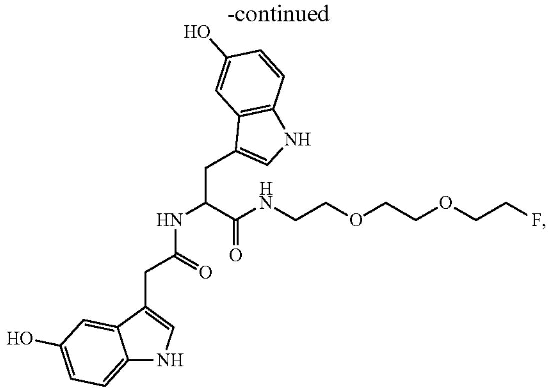
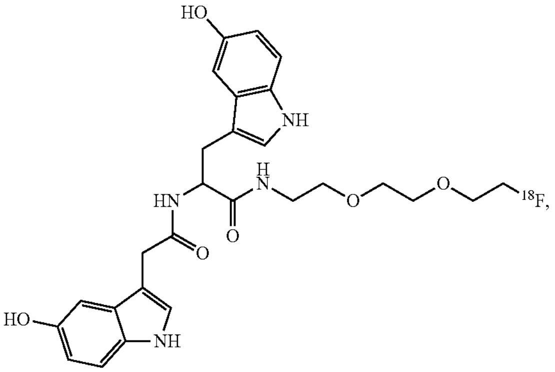
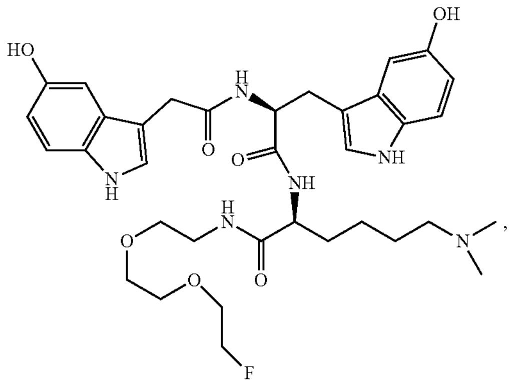
or
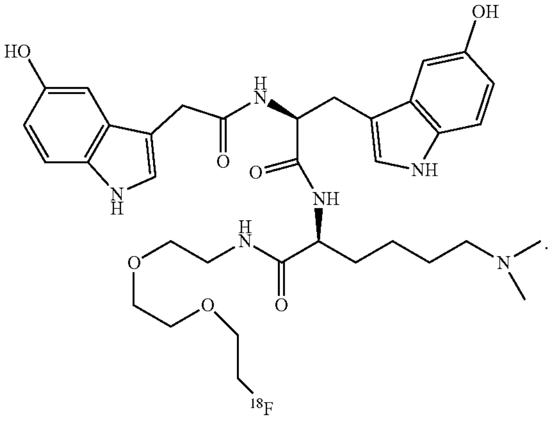

37. The method of claim 28, wherein the compound has formula:
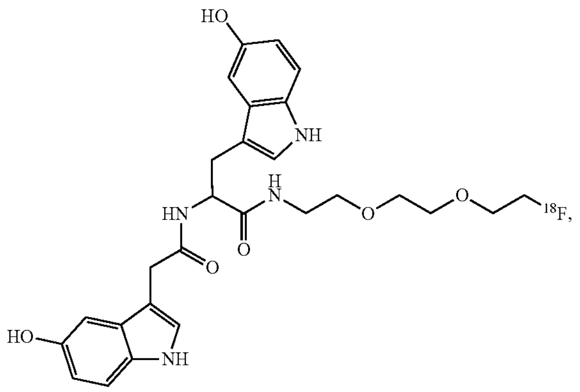 [SMILES: O=C(Cc1c[nH]c2ccc(O)cc12)NC(Cc1c[nH]c2ccc(O)cc12)C(=O)NCCOCCOCC[18F]]
or a pharmaceutically acceptable salt thereof.
* * * * *